(12) United States Patent
Gwaltney, II et al.

(10) Patent No.: US 6,228,868 B1
(45) Date of Patent: May 8, 2001

(54) OXAZOLINE ANTIPROLIFERATIVE AGENTS

(75) Inventors: Stephen L. Gwaltney, II, Lindenhurst; Hwan-Soo Jae, Glencoe; Douglas M. Kalvin, Buffalo Grove; Gang Liu, Gurnee; Hing L. Sham, Mundelein; Qun Li, Libertyville; Akiyo K. Claiborne; Le Wang, both of Mundelein, all of IL (US); Kenneth J. Barr, San Francisco, CA (US); Keith W. Woods, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/360,463

(22) Filed: Jul. 23, 1999

Related U.S. Application Data

(60) Provisional application No. 60/094,241, filed on Jul. 27, 1998.

(51) Int. Cl.⁷ .................. A61K 31/421; A61K 31/437; A61K 31/4709; C07D 263/08; C07D 413/04; A61P 35/00
(52) U.S. Cl. .................. 514/300; 514/314; 514/340; 514/374; 546/121; 546/166; 546/167; 546/209; 548/237; 548/239
(58) Field of Search .................. 546/121, 166, 546/167, 209; 548/237, 239; 514/300, 314, 340, 374

(56) References Cited

FOREIGN PATENT DOCUMENTS

| | | |
|---|---|---|
| 0359516 | 3/1990 | (EP) . |
| 0552880 | 7/1993 | (EP) . |
| 0596326 | 5/1994 | (EP) . |

OTHER PUBLICATIONS

Scientia Pharmaceutical, vol. 64 (1996), I.A. Shehata et al., pp. 133–143, "Synthesis and Biological Testing of Certain 1,3,4–Oxadiazole and 1,2,4–Triazole Derivatives as Potential Antimicrobial Agents".

Sof'ina et al. National Cancer Institute Monograph 55. NIH publication No. 80–1933, pp. 55, 77–78, 1980.*

Peet et al. J. Heterocyclic. Chem., 31, 419–423, Mar. 1994.*

Peet, et al., "Synthesis of a 2,5–Diaryloxazoline as a Potential Platelet–Activating Factor Antagonist", *Journal of Heterocyclic Chemistry*, vol. 31, pp. 419–423 (1994).

* cited by examiner

*Primary Examiner*—Evelyn Mei Huang
(74) *Attorney, Agent, or Firm*—Gregory W. Steele; B. Gregory Donner

(57) ABSTRACT

Compounds having Formula I

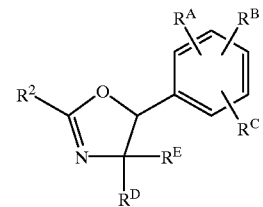

I are useful for treating cancer. Also disclosed are pharmaceutical compositions comprising compounds of Formula I, and methods of treating cancer in a mammal.

7 Claims, No Drawings

OXAZOLINE ANTIPROLIFERATIVE AGENTS

This application is a continuation-in-part of copending U.S. provisional application Ser. No. 60/094,241, filed Jul. 27, 1998, hereby incorporated by reference.

TECHNICAL FIELD

The present invention relates to substituted oxadiazolines which are useful for treating pathological states which arise from or are exacerbated by cell proliferation, to pharmaceutical compositions comprising these compounds, and to methods of inhibiting cell proliferation in a mammal.

BACKGROUND OF THE INVENTION

Neoplastic diseases are characterized by the proliferation of cells which are not subject to normal cell growth and are a major cause of death in humans and other mammals. Cancer chemotherapy has not only provided new and more effective drugs to treat these diseases but has also demonstrated that drugs which disrupt the microtubule system of the cytoskeleton are effective in inhibiting the proliferation of neoplastic cells.

The microtubule system of eucaryotic cells is a major component of the cytoskeleton and is a dynamic assembly and disassembly wherein heterodimers of tubulin are polymerized and form microtubule. Microtubules play a key role in the regulation of cell architecture, metabolism, and division and in their dynamic state are critical to normal cell function. With respect to cell division, tubulin is polymerized into microtubules that form the mitotic spindle. The microtubules are then depolymerized when the mitotic spindle's use has been fulfilled. Accordingly, agents which disrupt the polymerization or depolymerization of microtubules, and thereby inhibit mitosis, comprise some of the most effective cancer chemotherapeutic agents in clinical use. Thus agents which have the ability to disrupt the microtubule system are useful for cancer treatment.

Certain cryptophycin compounds are disclosed in U.S. Pat. Nos. 4,946,835, 4,845,085, 4,845,086, and 4,868,208; however, compounds having greater metabolic stability and longer duration of action are desired for most therapeutic uses. Thus there is still a need for compounds which inhibit mitosis.

SUMMARY OF THE INVENTION

In one embodiment of the invention is disclosed compounds having Formula I

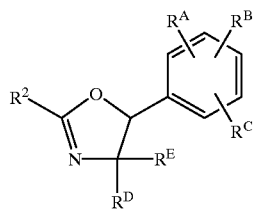

or a pharmaceutically acceptable salt or prodrug thereof, wherein $R^A$, $R^B$, and $R^C$ are independently selected from the group consisting of
(1) alkyl,
(2) alkoxy,
and
(3) thioalkoxy;

$R^D$ and $R^E$ are independently selected from the group consisting of
(1) hydrogen
and
(2) alkyl;

$R^2$ is selected from the group consisting of
(1) aryl,
(2) heterocycle,
wherein (1) and (2) can be optionally substituted with one, two, three, four, or five substituents independently selected from -L $R^6$ wherein $L^1$ is selected from the group consisting of
(a) a covalent bond,
(b) —C(X)—, wherein X is O or S,
(c) —S(O)$_t$—, wherein t is 0, 1, or 2,
(d) —NR$^3$—, wherein $R^3$ is selected from the group consisting of
(i) hydrogen,
(ii) carboxaldehyde,
(iii) alkanoyl,
(iv) alkoxycarbonyl,
(v) —C(O)OR$^{11}$, wherein $R^{11}$ is alkyl which can be optionally substituted with one or two aryl substituents,
(vi) cycloalkyl,
(vii) alkyl, wherein the alkyl can be optionally substituted with one or two substituents independently selected from the group consisting of
(1') alkoxy,
(2') cycloalkyl,
and
(3') aryl, wherein the aryl can be optionally substituted with one or two substituents independently selected from the group consisting of
(a') alkanoyloxy,
(b') hydroxy,
and
(c') alkoxy,
(viii) alkenyl,
(ix) alkynyl,
(x) —OR$^5$ wherein $R^5$ is selected from the group consisting of
(1') hydrogen, and
(2') alkyl, wherein the alkyl can be optionally substituted with one or two substituents independently selected from the group consisting of
(a') aryl,
(b') cycloalkyl,
and
(c') hydroxyl,
(xi) a nitrogen protecting group,
(xii) aryl,
and
(xiii) —C(O)R$^{13}$, wherein $R^{13}$ is perfluoroalkyl,
(e) —O—,
(f) —X'C(X)—, wherein X is defined previously and X' is O or S,
(g) —C(X)X'—,
(h) —N(R$^{3'}$)C(O)N(R$^{4'}$)— wherein $R^{3'}$ and $R^{4'}$ are independently selected from the
group consisting of
(i) hydrogen
and
(ii) alkyl, (i) -N(R$^{3'}$)C(X)—, wherein R$^{3'}$ is defined above,
(j) —C(X)N(R$^{3'}$)—, wherein R$^{3'}$ is defined above,
(k) —NR$^{3'}$S(O)$_t$—, wherein R$^{3'}$ is defined above, and
(l) —S(O)$_t$NR$^{3'}$— wherein t and R$^{3'}$ are defined above,
wherein (a)–(l) are drawn with their left ends attached to R$^2$ and their right ends attached to R., and R is selected from the group consisting of
  (a) -CO$_2$O$^5$, wherein R$^5$ is defined above,
  (b) —C(O)R$^5$, wherein R$^5$ is defined above,
  (c) —OC(O)R$^{10}$, wherein R$^{10}$ is alkyl which can be optionally substituted with one or two substituents selected from the group consisting of
    (i) alkoxy
    and
    (ii) hydroxy,
  (d) cyano,
  (e) nitro,
  (f) —XH,
  (g) halo,
  (h) —S(O)$_{t'}$NR$^3$R$^4$, wherein R$^3$ is defined above, t' is one or two, and R$^4$ is selected from the group consisting of
    (i) hydrogen,
    (ii) carboxaldehyde,
    (iii) alkanoyl,
    (iv) —C(O)OR$^{10}$, wherein R$^{10}$ is defined above,
    (v) —C(O)OR$^{11}$, wherein R$^{11}$ is defined above,
    (vi) cycloalkyl,
    (vii) alkyl, wherein the alkyl can be optionally substituted with one or two substituents independently selected from the group consisting of
      (1') —OR$^{10}$, wherein R$^{10}$ is defined above,
      (2') cycloalkyl,
      and
      (3') aryl, wherein the aryl can be optionally substituted with one or two substituents independently selected from the group consisting of
        (a') —OC(O)R , wherein R is defined above,
        (b') hydroxyl,
        and
        (c')—OR$^{10}$, wherein R$^{10}$ is defined above,
    (viii) alkenyl,
    (ix) alkynyl,
    and
    (x) —OR$^5$, wherein R$^5$ is defined above,
  (i) —NR$^3$R$^4$, wherein R$^3$ and R$^4$ are defined above,
  (j) perfluoroalkyl,
  (k) alkenyl,
  (l) alkynyl,
  (m) aryl,
  (n) heterocycle,
  (o) alkyl,
  (p) cycloalkyl,
  and
  (q) =X, wherein X is defined above,
  wherein (k)–(o) can be optionally substituted with one, two, three, four, or five substituents independently selected from the group consisting of
    (i) hydroxyl,
    (ii) halo,
    (iii) —OR$^{10}$, wherein R$^{10}$ is defined above,
    (iv) —SR$^{10}$, wherein R$^{10}$ is defined above,
    (v) —CO$_2$R , wherein R$^5$ is defined above,
    (vi) carboxaldehyde,
    (vii) =X, wherein X is defined above,
    (viii) azido,
    (ix) =C(H)NR$^3$R$^4$, wherein R$^3$ and R$^4$ are defined above,
    (x) cyano,
    (xi) =NOR$^3$, wherein R$^3$ is defined above,
    (xii) —NR$^3$R$^4$, wherein R$^3$ and R$^4$ are defined above,
    (xiii) —S(O)$_t$NR$^3$R$^4$, wherein R$^3$ and R$^4$ are defined above,
    (xiv) nitro,
    (xv) aryl,
    and
    (xvi) heterocycle,
(4) cycloalkyl,
and
(5) cycloalkenyl,
wherein (4) and (5) can be optionally substituted with one, two, three, or four substituents independently selected from the group consisting of
  (a) alkyl,
  (b) hydroxyl,
  and
  (c) aryl.

In another embodiment of the invention are disclosed methods of treating cancer comprising administering an effective amount of a compound having Formula I.

In yet another embodiment of the invention are disclosed pharmaceutical compositions containing compounds of Formula I.

Compounds of the invention include, but are not limited to, 2-(4-dimethylaminophenyl)-5-(3,4,5-trimethoxyphenyl)-Δ2,3-oxazoline,
2-(3-hydroxy-4-methoxyphenyl)-5-(3,4,5-trimethoxyphenyl)-Δ2,3-oxazoline,
2-(4-methoxyphenyl)-5-(3,4,5-trimethoxyphenyl)-Δ2,3-oxazoline,
2-(3,5-dimethoxyphenyl)-5-(3,4,5-trimethoxyphenyl)-Δ2,3-oxazoline,
2-(3-acetylindol-5-yl)-5-(3,4,5-trimethoxyphenyl)-Δ2,3-oxazoline,
2-(1-methylindol-5-yl)-5-(3,4,5-trimethoxyphenyl)-Δ2,3-oxazoline,
2-(indol-3-yl)-5-(3,4,5-trimethoxyphenyl)-Δ2,3-oxazoline,
2-(indol-2-yl)-5-(3,4,5-trimethoxyphenyl)-Δ2,3-oxazoline,
2-(1xindol-yl)-5-(3,4,5-trimethoxyphenyl)-Δ2,3-oxazoline,
2-(4-amino-3-methoxyphenyl)-5-(3,4,5-trimethoxyphenyl)-Δ2,3-oxazoline,
2-(indol-5-yl )-5-(3,4,5-trimethoxyphenyl)-Δ2,3-oxazoline,
2-(4-amino-3-methylphenyl)-5-(3,4,5-trimethoxyphenyl)-Δ2,3-oxazoline,
2-(3-hydroxy-4-methoxyphenyl)-4-dimethyl-5-(3,4,5-trimethoxyphenyl)-Δ2,3-oxazoline,
2-(N-methyl-tetrahydroquinol-6-yl)-5-(3,4,5-trimethoxyphenyl)-Δ2,3-oxazoline,
2-(2-methyl-cyclopropyl)-5-(3,4,5-trimethoxyphenyl)-Δ2,3-oxazoline,
2-(4-ethoxyphenyl)-5-(3,4,5-trimethoxyphenyl)-Δ2,3-oxazoline, 2-(3,4-dimethoxyphenyl)-5-(3,4,5-trimethoxyphenyl)-Δ2,3-oxazoline,
2-(4-benzyloxy-3-methoxyphenyl)-5-(3,4,5-trimethoxyphenyl)-Δ2,3-oxazoline,
2-(2,3-dihydro-5-bromo-7-benzofuranyl)-5-(3,4,5-trimethoxyphenyl)-Δ2,3-oxazoline,
2-(3-acetoxy-4-methoxyphenyl)-5-(3,4,5-trimethoxyphenyl)-Δ2,3-oxazoline,
2-(1-methyl-2,3-dihydro-indol-5-yl)-5-(3,4,5-trimethoxyphenyl)-(2,3-oxazoline,
2-(1-methylindol-5-yl)-5-(3,4,5-trimethoxyphenyl)-Δ2,3-oxazoline, hydrochloride,
(5S)-2-(1-methylindol-5-yl)-5-(3,4,5-trimethoxyphenyl)-Δ2,3-oxazoline,
(5R)-2-(1-methylindol-5-yl)-5-(3,4,5-trimethoxyphenyl)-Δ2,3-oxazoline,
2-(1-ethylindol -5-yl)-5-(3,4,5-trimethoxyphenyl)-Δ2,3-oxazoline,
2-(6-indolyl)-5-(3,4,5-trimethoxyphenyl)-Δ2,3-oxazoline,
2-(-methylindol-6-yl)-5-(3,4,5-trimethoxyphenyl)-Δ2,3-oxazoline,
2-(4-indolyl)-5-(3,4,5-trimethoxyphenyl)-Δ2,3-oxazoline,
2-(1-methylindol-4-yl)-5-(3,4,5-trimethoxyphenyl)-Δ2,3-oxazoline,
2-(7-indolyl)-5-(3,4,5-trimethoxyphenyl)-Δ2,3-oxazoline,
2-(1-methindolyl)-7-yl)-5-(3,4,5-trimethoxyphenyl)-Δ2,3-oxazoline,
2-(1-methylindol-3-yl)-5-(3,4,5-trimethoxyphenyl)-Δ2,3-oxazoline,
2-(1-methyl-indol-2-yl)-5-(3,4,5-trimethoxyphenyl)-Δ2,3-oxazoline,
2-(6-qu linol2yl)-5-(3,4,5-trimethoxyphenyl)-Δ2,3-oxazoline,
2-(3-quinolinyl)-5-(3,4,5-trimethoxyphenyl)-Δ2,3-oxazoline,
2-(4-quinolinyl)-5-(3,4,5-trimethoxyphenyl)-Δ2,3-oxazoline,
2-(4-quinolinyl)-5-(3,4,5-trimethoxyphenyl)-Δ2,3-oxazoline,
2-(1-isoqninolinyl)-5-(3,4,5-trimethoxyphenyl)-Δ2,3-oxazooine,
2-(3-amino-4-methoxyphenyl)-5-(3,4,5-trimethoxyphenyl)-Δ2,3-oxazoline,
2-(3-amino-4-methyphenyl)-5-(3,4,5-trimethoxyphenyl)-Δ2,3-oxazoline,
2-(3-(Ala-Ala-amino-4-methoxyphenyl)-5-(3,4,5-trimethoxyphenyl)-Δ2,3-oxazoline,
2-(3-(Ala-amino-4-methoxyphenyl)-5-(3,4,5-trimethoxyphenyl)-Δ2,3-oxazoline,
2-(3-((3-aminopropionoyl)amino-4-methoxyphenyl)-5-(3,4,5-trimethoxyphenyl)-Δ2,3-oxazoline,
2-(3-(Ser-amino-4-methoxyphenyl)-5-(3,4,5-trimethoxyphenyl)-Δ2,3-oxazoline,
2-(3-(Gly-amino-4-methoxyphenyl)-5-(3,4,5-trimethoxyphenyt)-Δ2,3-oxazoline,
2-(1-methyl-1H-pyridin-2-on-4-yl)-5-(3,4,5-trimethoxyphenyl)-Δ2,3-oxazoline,
2-(2-(2-hydroxyethyloxy)-4-pyridinyl)-5-(3,4,5-trimethoxyphenyl)-Δ2,3-oxazoline,
2-(imidazo[1,2-α]pyridin-6-yl)-5-(3,4,5-trimethoxyphenyl)-Δ2,3-oxazoline,
2-(imidazo[1,5-α]pyridin-6-yl)-5-(3,4,5-trimethoxyphenyl)-Δ2,3-oxazoline,
2-(2-methyl-6-indolizinyl)-5-(3,4,5-trimethoxyphenyl)-Δ2,3-oxazoline,
2-(3-fluoro-4-methoxyphenyl)-5-(3,4,5-trimethoxyphenyl)-Δ2,3-oxazoline,
2-((2S)-indolin-2-yl)-5-(3,4,5-trimethoxyphenyl)-Δ2,3-oxazoline,
2-(2-chloro-4-nitrophenyl)-5-(3,4,5-trimethoxyphenyl)-Δ2,3-oxazoline,
2-(2-fluoro-4-nitrophenyl)-5-(3,4,5-trimethoxyphenyl)-Δ2,3-oxazoline.
2-(1,4-dimethylindol-5-yl)-5-(3,4,5-trimethoxyphenyl)-Δ2,3-oxazoline,
(2-(1-methylthiothiocarbonylindol-5-yl)-5-(3,4,5-trimethoxyphenyl)-Δ2,3-oxazoline,
2-(1,3-dimethylindol-5-yl)-5-(3,4,5-trimethoxyphenyl)-Δ2,3-oxazoline,
2-(6-chloroindol-5-yl)-5-(3,4,5-trimethoxyphenyl)-Δ2,3-oxazoline,
2-(1-methyloxindol-5-yl)-5-(3,4,5-trimethoxyphenyl)-Δ2,3-oxazoline,
2-(1-methyl-6-chloroindol-5-yl)-5-(3,4,5-trimethoxyphenyl)-Δ2,3-oxazoline,
2-(1-difluoromethylindol-5-yl)-5-(3,4,5-trimethoxyphenyl)-Δ2,3-oxazoline,
2-(3-chloro-1-methylindol-5-yl)-5-(3,4,5-trimethoxyphenyl)-Δ2,3-oxazoline,
2-(7-fluoro-5-indolyl)-5-(3,4,5-trimethoxyphenyl)-Δ2,3-oxazoline,
2-(1-methyl-7-fluoro-5-indolyl)-5-(3,4,5-trimethoxyphenyl)-Δ2,3-oxazoline,
2-(7-chloro-5-indolyl)-5-(3,4,5-trimethoxyphenyl)-Δ2,3-oxazoline,
2-(1-methyl-7-chloro-5-indolyl)-5-(3,4,5-trimethoxyphenyl)-Δ2,3-oxazoline,
2-(3-fluoro-5-indolyl)-5-(3,4,5-trimethoxyphenyl)-Δ2,3-oxazoline,
(2-(1-methyl-3-fluoro-5-indolyl)-5-(3,4,5-trimethoxyphenyl)-Δ2,3-oxazoline,
2-(1-hydroxymethylindol-5-yl)-5-(3,4,5-trimethoxyphenyl)-Δ2,3-oxazoline,
2-(1-methoxymethyl-5-indolyl)-5-(3,4,5-trimethoxyphenyl)-Δ2,3-oxazoline,
2-(1,2-dimethyl-5-indolyl)-4,5-trimethoxyphenyl)-Δ2,3-oxazoline,
2-(7-methyl-5-indolyl)-5-(3,4,5-trimethoxyphenyl)-Δ2,3-oxazoline,
2-(1,7-dimethyl-5-indolyl)-5-(3,4,5-trimethoxyphenyl)-Δ2,3-oxazoline,
2-(1,2,7-timethylindol-5-yl)-5-(3,4,5-trimethoxyphenyl)-Δ2,3-oxazoline,
2-(1,2-dimethylbenzimidazol-5-yl)-5-(3,4,5-trimethoxyphenyl)-Δ2,3-oxazoline,
2-(3-trifluoroacetyl-5-indolyl)-S-(3,4,5-trimethoxyphenyl)-Δ2,3-oxazoline,
(2-(1-methyl-3-trifluoroacetylindol-5-yl)-5-(3,4,5-trimethoxyphenyl)-Δ2,3-oxazoline,
2-(1-(2,2,2-trifluoroethyl)indol-5-yl)-5-(3,4,5-trimethoxyphenyl)-Δ2,3-oxazoline, and 2-(1-cyclopropyl-5-indolyl)-5-(3,4,5-trimethoxyphenyl)-Δ2,3-oxazoline.

DETAILED DESCRIPTION OF THE INVENTION

Definition of Terms

The term "alkanoyl," as used herein, refers to an alkyl group attached to the parent molecular group through a carbonyl group.

The term "alkanoyloxy," as used herein, refers to an alkanoyl group attached to the parent molecular group through an oxygen atom. The alkanoyloxy groups of this invention can be optionally substituted.

The term "alkenyl," as used herein, refers to a monovalent straight or branched chain group of 2–6 carbon atoms containing at least one carbon—carbon double bond.

The term "alkoxy," as used herein, refers to an alkyl group attached to the parent molecular group through an oxygen atom.

The term "alkoxycarbonyl," as used herein, refers to an alkoxy group attached to the parent molecular group through a carbonyl group.

The term "alkyl," as used herein, refers to a saturated straight or branched chain group of 1–6 carbon atoms derived from an alkane by the removal of one hydrogen atom. The alkyl groups of this invention can be optionally substituted.

The term "alkynyl," as used herein, refers to a monovalent straight or branched chain group of 2–6 carbons containing at least one carbon—carbon triple bond. The alkynyl groups of this invention can be optionally substituted.

The term "aryl," as used herein, refers to a mono- or bicyclic carbocyclic ring system having 1 or 2 aromatic rings. The aryl group can also be fused to a cyclohexane, cyclohexene, cyclopentane or cyclopentene ring. The aryl groups of this invention can be optionally substituted.

The term "azido," as used herein, refers to —N$_3$.

The term "carboxaldehyde," as used herein, refers to —CHO.

The term "carbony," as used herein, refers to —C(O)—.

The term "cyano," as used herein, refers to —CN.

The term "cycloalkenyl," as used herein, refers to a monovalent group derived from a cyclic or bicyclic hydrocarbon of 3–12 carbons that has at least one carbon—carbon double bond.

The term "cycloalkyl," as used herein, refers to a monovalent group 3–12 carbons derived from a saturated cyclic or bicyclic hydrocarbon.

The term "halo," as used herein, refers to —F, —Cl, —Br, or —I.

The term "heterocycle," as used herein, represents a represents a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, imidazo[1,2-α]pyridinyl, 1,2-dihydropyridinyl, imidazo[1,5-α]pyridine, indolizine, 2,3,3a,7a-tetrahydro-1H-indole, and the like.

Heterocyclics also include bridged bicyclic groups where a monocyclic heterocyclic group is bridged by an alkylene group such as

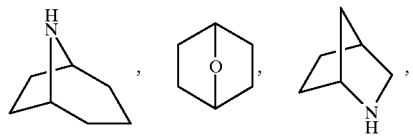

and the like.

Heterocyclics also include compounds of the formula

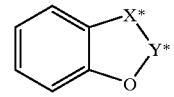

where X* is selected from —CH$_2$—, —CH$_2$O— and —O—, and Y* is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, and the like. The heterocycle groups of this invention can be optionally substituted.

The term "hydroxyl," as used herein, refers to —OH.

The term "nitro," as used herein, refers to —NO$_2$.

The term "nitrogen protecting group," as used herein, as used herein refers to groups intended to protect an amino group against undesirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "perfluoroalkyl," as used herein, refers to an alkyl group in which all of the hydrogen atoms have been replaced by fluoride atoms.

The term "pharmaceutically acceptable prodrugs," as used herein, represents those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to parent compounds having formula I, for example, by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are hereby incorporated by reference. Particularly preferred prodrugs of the invention include compounds having formula I, wherein a nitrogen, hydroxy, or thiol group has attached thereto an aminoacyl, bisaminoacyl (2-mer), or trisaminoacyl (3-mer) group optionally capped with a carboxyl protecting group. The term "aminoacyl," as used herein, refers to a group derived from naturally or unnaturally occuring amino acids. Representative aminoacyl groups include those derived from glycine, alanine, β-alanine, valine, leucine, iso-leucine, methionine, serine, threonine, cysteine, phenylalanine, and tyrosine in the racemic, D or L configurations. The terms "bisaminoacyl" and "trisaminoacyl," as used herein, refer to di- and tri-aminoacyl groups, respectively. Representative examples of bisaminoacyl and trisaminoacyl groups include 2-mers and 3-mers derived from glycine, alanine, β-alanine, valine, leucine, iso-leucine, methionine, serine, threonine, cysteine, phenylalanine, and tyrosine in the racemic, D or L configurations.

The term "pharmaceutically acceptable salt" as used herein refers to salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences, 1977, 66:1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Determination of Biological Activity

Compounds of this invention were tested in a 48-hour cellular proliferation assay that uses human colon adenocarcinoma, MDR positive (HCT-15) cells, and human lung large cell carcinoma, MDR negative (NCI-H460) cells, in the 96-well microtitre format described in Skehan P., et al. New Colorimetric Cytotoxicity Assay for Anticancer Drug Screening. 1990, J. Natl. Cancer Inst. 82:1107–1112, hereby incorporated by reference. Briefly, the wells of a microtitre plate were charged sequentially with cultured cells and compounds of the invention ($1.0 \times 10^{-4}$ to $1.0 \times 10^{-11}$ M in 10% DMSO prepared by dissolving compounds of the invention in DMSO and adding 11 $\mu$L of the DMSO solution to 100 $\mu$L of culture medium for a final DMSO concentration of 10%). Two of the following controls were also present in each microtitre plate: a solvent (DMSO) control without drug that yielded a 0% inhibition level and a trichloroacetic acid-treated well that yielded a 100% inhibition level. The cells were grown in culture (37° C., 5% $CO_2$ atmosphere) for 48 hours then fixed by the addition of trichloroacetic acid. The wells were stained with sulforhodamine, washed with 1% acetic acid, and treated with 0.01 M tris buffer (100 $\mu$L) to solubilize the adherent dye. The absorbance of the dye solution was measured with a Molecular Devices Spectra-Max340 plate reader. Percent inhibition and Inhibitory Concentrations ($IC_{50}$) values were obtained by calculating the proportional response of the experimental values to the absorbance values of the controls. These data are shown in Tables 1 and 2.

TABLE 1

Inhibitory Potency of Representative Compounds

| Example Number | NCI-460 (% Inhibition at $10^{-4}$ M) | HCT-15 (% Inhibition at $10^{-4}$ M) |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 100 |
| 15 | 50 | 50 |
| 16 | 90.68 | 96.22 |
| 17 | 85.77 | 91.05 |
| 18 | 92.18 | 95.95 |
| 19 | 100 | 98.89 |
| 20 | 100 | 90.97 |
| 21 | 92.41 | 100 |
| 22 | 100 | 100 |

TABLE 2

Inhibitory Potency of Representative Compounds

| | IC$_{50}$ (HCT-15) | IC$_{50}$ (NCI-H460) |
|---|---|---|
| 27 | 83 nM | 170 nM |
| 28 | 210 nM | 390 nM |
| 29 | 39 nM | 60 nM |
| 30 | 24 nM | 28 nM |
| 31 | 580 nM | 470 nM |
| 32 | 16 μM | 350 μM |
| 33 | 32 nM | 120 nM |
| 34 | 650 nM | 1500 nM |
| 35 | 2.4 μM | 3.2 μM |
| 36 | 160 μM | 270 μM |
| 37 | 44 μM | 37 μM |
| 38 | 63 μM | 78 μM |
| 39 | 33 nM | 68 nM |
| 40 | 62 nM | 82 nM |
| 41 | 520 nM | 590 nM |
| 44 | 6.6 μM | 3.8 μM |
| 46 | 440 nM | 470 nM |
| 56 | 12 μM | 6 μM |
| 60 | 280 nM | 410 nM |
| 61 | 1.9 nM | 1.8 nM |
| 62 | 23 nM | 37 nM |
| 63 | 20 nM | 43 nM |
| 64 | 3.96 nM | 2.9 nM |
| 65 | 37 nM | 51 nM |
| 66 | 46 nM | 100 nM |
| 67 | 23 nM | 38 nM |
| 68 | 47 nM | 150 nM |
| 69 | 450 nM | 680 nM |
| 70 | 170 nM | 210 nM |
| 71 | 5 nM | 17 nM |
| 72 | 11 nM | 36 nM |
| 73 | 34 nM | 41 nM |
| 74 | 1.3 μM | 1.2 μM |
| 75 | 1.9 μM | 3.8 μM |
| 76 | 1.30 μM | 540 μM |
| 77 | 3.8 μM | 4.2 μM |
| 78 | 1.9 μM | 3.5 μM |

As shown by the data in Table 1 and Table 2, the compounds of the invention, including but not limited to those specified in the examples, are useful for the treatment of diseased caused or exasercbated by cell proliferation. As cell proliferation inhibitors, these compounds are useful in the treatment of both primary and metastatic solid tumors and carcinomas of the breast, colon, rectum, lung, oropharynx, hypopharynx, esophagus, stomach, pancreas, liver, gallbladder, bile ducts, small intestine, urinary tract including kidney, bladder and urothelium, female genital tract including cervix, uterus, ovaries, choriocarcinoma, and gestational trophoblastic disease, male genital tract including prostate, seminal vesicles, testes, and germ cell tumors, endocrine glands including thyroid, adrenal, and pituitary, skin including hemangiomas, melanomas, sarcomas arising from bone or soft tissues including Kaposi's sarcoma, tumors of the brain, nerves, and eyes, meninges including astrocytomas, gliomas, glioblastomas, retinoblastomas, neuromas, neuroblastomas, Schwannomas and meningiomas, solid tumors arising from hematopoietic malignancies including leukemias and chloromas, plasmacytomas, plaques, tumors of mycosis fungoides, cutaneous T-cell lymphomaaleukemia, lymphomas including Hodgkin's and non-Hodgkin's lymphomas, prophylaxis of autoimmune diseases including rheumatoid, immune and degenerative arthritis, ocular diseases including diabetic retinopathy, retinopathy of prematurity, corneal graft rejection, retrolental fibroplasia, neovascular glaucoma, rubeosis, retinal neovascularization due to macular degeneration, hypoxia, abnormal neovascularization conditions of the eye, skin diseases including psoriasis, blood vessel diseases including hemagiomas and capillary proliferation within atherosclerotic plaques, Osler-Webber Syndrome, myocardial angiogenesis, plaque neovascularization, telangiectasia, hemophiliac joints, angiofibroma, and wound granulation.

The compounds of the present invention may also be useful for the prevention of metastases from the tumors described above either when used alone or in combination with radiotherapy and/or other chemotherapeutic treatments conventionally administered to patients for treating cancer. For example, when used in the treatment of solid tumors, compounds of the present invention may be administered with chemotherapeutic agents such as alpha inteferon, COMP (cyclophosphamide, vincristine, methotrexate, and prednisone), etoposide, MBACOD (methortrexate, bleomycin, doxorubicin, cyclophosphamide, vincristine, and dexamethasone), PRO-MACE/MOPP (prednisone, methotrexate (w/leucovin rescue), doxorubicin, cyclophosphamide, taxol, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. Other chemotherapeutic agents include alkylating agents such as nitrogen mustards (mechloethamine, melphan, chlorambucil, cyclophosphamide and ifosfamide), nitrosoureas including carmustine, lomustine, semustine and streptozocin, alkyl sulfonates including busulfan, triazines including dacarbazine, ethyenimines including thiotepa and hexamethylmelamine, folic acid analogs including methotrexate, pyrimidine analogues including 5-fluorouracil and cytosine arabinoside, purine analogs including 6-mercaptopurine and 6-thioguanine, antitumor antibiotics including actinomycin D, anthracyclines including doxorubicin, bleomycin, mitomycin C and methramycin, hormones and hormone antagonists including tamoxifen, cortiosteroids and miscellaneous agents including cisplatin and brequinar. For example, a tumor may be treated conventionally with surgery, radiation or chemotherapy and compound of Formula I administration with subsequent compound of Formula I adminsteration to extend the dormancy of micrometastases and to stabilize and inhibit the growth of any residual primary tumor.

Methods of Treatment

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally , intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Synthetic Methods

The compounds and processes of the present invention will be better understood in connection with the following synthetic schemes which illustrate the methods by which the compounds of the invention may be prepared. The compounds of this invention may be prepared by a variety of synthetic routes. Representative procedures are outlined in Scheme I where $R^A$, $R^B$, $R^C$, $R^D$, $R^E$, and $R^2$, are defined previously unless indicated otherwise. Depending on the nature of $R^A$, $R^B$, $R^C$, $R^D$, $R^E$, and $R^2$, protection and subsequent deprotection of other reactive groups can be required to successfully complete the described synthetic sequences. Commonly used protecting groups are disclosed in Greene, "Protective Groups In Organic Synthesis," (John Wiley & Sons, New York (1981)), which is incorporated herein by reference. It will be readily apparent to one of ordinary skill in the art reviewing the synthetic route depicted below that other compounds within Formula I can be synthesized by the substitution of appropriate reactants and agents in the synthesis shown below.

Abbreviations

Abbreviations which have been used in the descriptions of the schemes and the examples that follow are: THF for tetrahydrofuran; DMF for N,N-dimethylformamide; EDC for 1-(3-dimethylaminopropyl)-3-ethylcarbodiimide hydrochloride; LDA for lithium diisopropylamnide; TFA for trifluoroacetic acid; DMSO for dimethylsulfoxide; DMAP for 4-(N,N-dimethylamino)pyridine; HBTU for O-(azabenzotriazole-1-yl)-N,N,N',N'-tetramethyluroniumhexafluorophosphate; Boc for tert-butylcarbonyloxy; DPPA for diphenylphosphoryl azide; DCC for dicyclohexylcarbodiimide; EDC for 1-(3-dimethylaminopropyl)-3-ethylcarbodiimide hydrochloride. Starting materials, reagents and solvents were purchased from Aldrich Chemical Company (Milwaukee, Wis.).

Scheme 1

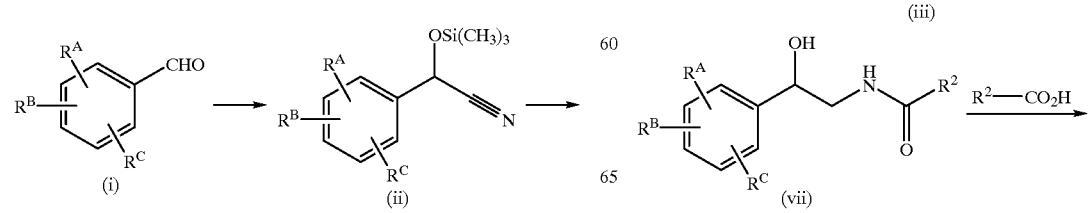

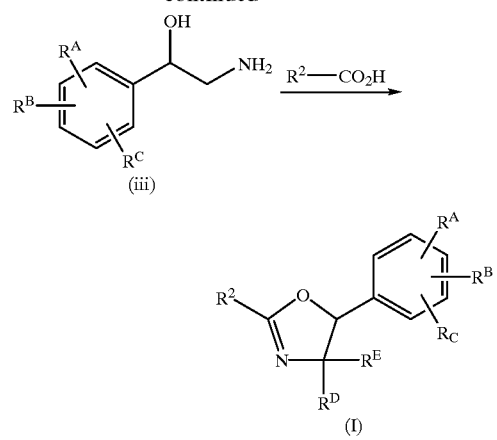

As shown in Scheme 1, the aldehyde (i) can be treated with trimethylsilylnitrile to provide silyloxynitrile intermediate (ii) which can be treated with reducing agents such as lithium aluminum hydride to provide amino alcohol (iii). Treatment of (iii) with carboxylic acids in the presence of a dehydrating agents such as trifluoromethane sulfonic anhydride and base provides compounds of Formula 1. Although the solvents used in these reactions is not particularly limited, a solvent which is little reactive with the starting materials and in which the starting materials are soluble is generally used. Examples of such solvents include pyridine, diisopropylethylamine, triethylamine, THF, dioxane, benzene, toluene, diethyl ether, chloroform, dichloromethane, ethyl acetate, DMF, DMSO, or mixtures thereof The reactions can be run at room temperature, or at lower or elevated temperatures, as needed. The reaction times are generally 30 minutes to 18 hours and can be arbitrarily selected depending on the types of starting materials and the reaction temperature.

Scheme 2

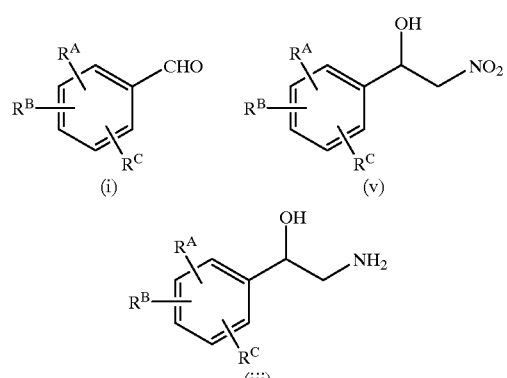

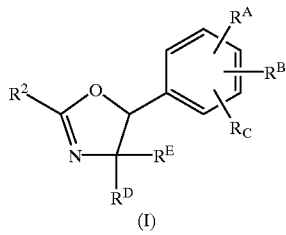

(I)

As shown in Scheme 2, treatment of (i) with nitromethane in the presence of base, such sodium or potassium hydroxide, provided hydroxy nitro intermediate (v) which, upon treatment with a reducing agent such as palladium on carbon, provided aminol (iii). Treatment of (iii) with a carboxylic acid in the presence of a dehydrating agent such as EDCI provided amide (vii) which was dehydrated in the presence of methoxycarbonylsulfamoyl)triethylammonium hydroxide to provide compounds of Formula I. Although the solvents used in these reactions is not particularly limited, a solvent which is little reactive with the starting materials and in which the starting materials are soluble is generally used. Examples of such solvents include THF, dioxane, benzene, toluene, diethyl ether, chloroform, dichloromethane, ethyl acetate, or mixtures thereof The reactions can be run at room temperature, or at lower or elevated temperatures, as needed. The reaction times are generally 30 minutes to 18 hours and can be arbitrarily selected depending on the types of starting materials and the reaction temperature.

The compounds and processes of the present invention will be better understood in connection with the following examples, which are intended as an illustration of and not a limitation upon the scope of the invention.

EXAMPLE 1

2-(4-dimethylaminophenyl)-5-(3,4,5-trimethoxyphenyl)-Δ2,3-oxazoline

EXAMPLE 1A 1-(1-hydroxy-2-aminoethyl)-3,4,5-trimethoxy benzene

A solution of 3,4,5-trimethoxybenzaldehyde (10 g, 51 mmol) and nitromethane (10 mL) in ethanol at 0° C. was treated with 10% sodium hydroxide (21.4 mL, 53.5 mmol), stirred for 45 sesonds, treated with 2% acetic acid (162 mL), stirred for 1 hour in the ice bath, and filtered. The solid was washed with water and dried under vacuum to provide 9.0 g of the desired product as an off-white solid.

EXAMPLE 1B 2-amino-1-(3,4,5-trimethoxyphenyl)ethanol

Example 1A was reduced with 10% Pd/C in acetic acid under 4 atmospheres for 3 hours to provide the desired product as the acetic acid salt.

mp 103–104° C.;

MS (CDI/NH$_3$) m/z 228 (M+H)$^+$;

$^1$H NMR (300 MHz, CDCl$_3$) δ 2.08 (s, 3H), 2.82-2.90 (m, 1H), 3.03–3.08 (m, 1H), 3.83 (s, 3H), 3.88 (s, 6H), 4.62–4.67 (m, 1H), 6.60 (s, 2H).

EXAMPLE 1C 1-((1-hydroxy-2-((4-dimethylamino)bezoylamino) ethyl)-3,4,5-trimethoxy benzene A solution of Example 1B (287 mg) and diisopropylethylamine (2 mL) in dichloromethane (15 mL) at 0° C. was treated slowly with a solution of 4-dimethylamino benzoylchloride (219 mg) in dichloromethane (10 mL), stirred for 18 hours warming to room temperature, and concentrated to near dryness. The concentrate was purified by column chromatography on silica gel with 1:1 hexanes/ethyl acetate to provide 340 mg of the desired product as a white solid.

mp 155–157° C.;

MS (CDI/NH$_3$) m/z 375 (M+H)$^+$;

$^1$H NMR (300 MHz, CDCl$_3$) δ 3.03 (s, 6H), 3.44–3.57 (m, 1H), 3.83 (s, 9H), 4.02 (bs, 1H), 4.88–4.95 (m, 1H), 6.62 (s, 2H), 6.64 (d, J=7 Hz, 2H), 7.66 (d, J=7 Hz, 2H).

EXAMPLE 1D 2-(4-dimethylaminophenyl)-5-(3,4,5-trimethoxyphenyl)-Δ2,3-oxazoline A solution of Example 1C (320 mg, 0.86 mmol) in chloroform (15 mL) at cooled to −20° C. was treated sequentially with pyridine (0.2 mL) and by triflic anhydride (0.2 mL), stirred for 30 minutes, washed with saturated NaHCO$_3$ and brine, dried (Na$_2$SO$_4$), filtered, and concentrated. The concentrate was purified by flash chromotography on silica gel with 1:1 hexanes/ethyl acetate to provide 220 mg of the desired product as an off-white solid.

MS (DCI/NH$_3$) m/z 357 (M+H)$^+$;

$^1$H NMR (300 MHz, CDCl$_3$) δ 3.05 (s, 6H), 3.85 (s, 9H), 3.96 (dd, 1H, J=7 Hz), 4.43 (dd, 1H, J=9 Hz), 5.57 (t, 1H, J=7 Hz), 6.58 (s, 2H), 6.70 (d, 2H, J=8 Hz), 7.93 (d, 2H, J=8 Hz).

EXAMPLE 2

2-(3-hydroxy-4-methoxyphenyl)-5-(3,4,5-trimethoxyphenyl)-Δ2,3-oxazoline

Example 20 was hydrolyzed to provide the desired product.

MS (DCI/NH$_3$) m/z 360 (M+H)$^+$;

$^1$H NMR (CDCl$_3$) δ 7.61–7.59 (m, 2H), 6.89 (d, 1 H, J=8.5 Hz), 6.56 (s, 2H), 5.77 (bs, 1H), 5.59–5.54 (m, 1H), 4.48–4.39 (m, 1H), 4.02–3.95 (m, 1H), 3.95 (s, 3H), 3.86 (s, 6H), 3.84 (s, 3 H).

EXAMPLE 3

2-(4-methoxyphenyl)-5-(3,4,5-trimethoxyphenyl)-Δ2,3-oxazoline 3, 5-Dimethoxybenzoic acid was processed as described in Example 4 to provide the desired product.

MS (DCI/$_3$) m/z 344 (M+H)$^+$;

$^1$H NMR (CDCl$_3$) δ 8.06–7.99 (m, 2H), 6.98–6.92 (m, 2H), 6.57 (s, 2H), 5.59 (dd, 1 H, J=9.8, 8.5 Hz), 4.46 (dd, 1 H, J=14.6, 10.2 Hz), 4.00 (dd, 1 H, J=14.6, 8.5 Hz), 3.87 (s, 3H), 3.85 (s, 9 H).

EXAMPLE 4

2-(3,5-dimethoxyphenyl)-5-(3,4,5-trimethoxyphenyl)-Δ2,3-oxazoline

EXAMPLE 4A

N-(2-hydroxy-2-phenylethyl)-3,5-dimethoxybenzamide

A suspension of 3,5-dimethoxybenzoic acid (1.00 g, 5.49 mmol) in dichloromethane (50 mL) at 0° C. was treated with HOBt hydrate (0.742 g, 5.49 mmol), stirred for 15 minutes, treated with EDCI (1.05 g, 5.49 mmol) in one portion, stirred for an additional 25 minutes, treated with triethylamine (1.84 g; 2.53 mL, 1.9 mmol) and the acetate salt of 2-amino-1-(3,4,5-trimethoxyphenyl)ethanol (1.58 g, 005.49 mmol), stirred for 18 hours while warming to room temperature, and concentrated. The concentrate was partitioned between ethyl acetate (400 mL) and water (200 mL), and the organic extract was washed sequentially with 10% $KHSO_4$ (200 mL), water (100 mL), $NaHCO_3$ (200 mL), and water (100 mL), dried ($MgSO_4$), filtered, and concentrated to provide 1.56 g of the desired product as a white foamy semi-solid.

MS (ESI(+)) m/z 392 (M+H)$^+$ and 374 (M+H−18) +;

$^1$H NMR; (CDCl$_3$) δ 3.50 (m, 1H), 3.70–3.80 (overlapping s's; 15H), 3.90 (m, 1H), 4.90 (d of d, J=7.0; 12.0 Hz; 1H), 6.55–6.65 (t, m; and s; J=7.0 Hz; 4H), 6.90 (d, J=3.0 Hz; 2H).

EXAMPLE 4B 2-(3,5-dimethoxyphenyl)-5-(3,4,5-trimethoxyphenyl)-Δ2,3-oxazoline A solution of Example 4A (50 mg, 0.128 mmol) in CHCl$_3$ (0.50 mL) was treated sequentially with triethylamine (89.5 μL, 65 mg, 0.64 mmol) and methanesulfonyl chloride (15.6 mg., 10.7 μL, 0.138 mmol), heated at reflux for 48 hours, cooled to room temperature, treated with CHCl$_3$ (1.0 mL) and water (0.200 mL), heated to reflux for 1 hour, cooled to room temperature; diluted with CHCl$_3$ (3.0 mL), washed sequentially with water (2×3 mL), 10% NaHCO$_3$ (3 mL), water (3 mL), and brine (3 mL), dried (Na$_2$SO$_4$), filtered and concentrated. The concentrate was purified by elution with a solution of 9:1 hexanes/acetone from a 2.00 g silica gel Analtech Sep-pak® cartridge to provide 10 mg of the desired product.

MS (APCI(+)) m/z 374 (M+H)$^+$ and (APCI(−)) m/z 372 (M−H)$^−$;

$^1$H NMR (CDCl$_3$) δ 3.80–3.90 (overlapping s; 15H), 4.01 (dd, J=8.4, 14.9 Hz; 1H), 4.47 (dd, J=8.4, 14.9 Hz.; 1H), 5.59 (ps t, J=10.1 Hz; 1H), 6.55 (s, 2H), 6.62 (t, J=7.0 Hz; 1H), 7.35 (d, J=3.0 Hz.; 2H). $^1$H NMR purity was greater than oe equal to 95%.

EXAMPLE 5

2-(3-acetylindol-5-yl)-5-(3,4,5-trimethoxyphenyl)-Δ2,3-oxazoline

A solution of Example 11 (50 mg, 0.142 mmol) in dichloromethane at room temperature was treated sequentially with triethylamine (0.5 mL), DMAP (5 mg), and acetic anhydride (0.5 mL, excess), stirred at room temperature for 3 hour, and concentrated. The concentrate was purified by flash on silica gel with 1:1 hexanes/ethyl acetate to provide 25 mg of the desired product as an off-white solid.

MS (DCI/NH$_3$) m/z 395 (M+H)$^+$;

$^1$H NMR (300 MHz, CDCl$_3$) δ 2.68 (s, 3H), 3.86 (s, 9H), 4.15 (brm, 1H), 4.55 (brm, 1H), 5.77 (brn, 1H), 6.60 (s, 2H), 6.76 (d, J=4.2 Hz, 1H), 7.52 (d, J=4.2 Hz, 1H), 8.12 (d, J=9.0 Hz, 1H), 8.55 (d, J=9.0 Hz, 1H).

EXAMPLE 6

2-(1-methylindol-5-yl)-5-(3,4,5-trimethoxyphenyl)-Δ2,3-oxazoline

A mixture of crushed KOH (64 mg, 1.14 mmol) in DMSO (1 mL) was stirred at room temperature for 5 minutes then treated with Example 11 (40 mg, 0.114 mmol), stirred for 45 minutes, treated with methyl iodide, (14.4 μL, 0.23 mmol), stirred for 24 hours, treated with water, and extracted with ethyl acetate (2×10 mL). The extract was washed with water and brine, dried (Na$_2$SO$_4$), and concentrated. The concentrate was purified by flash column chromatography on silica gel to provide 20 mg of the desired product.

MS (DCI/NH$_3$) m/z 367 (M+H)$^+$;

$^1$H NMR (300 MHz, DMSO-d$_6$) δ 3.65 (s, 3H), 3.75 (s, 6H), 3.83 (s, 3H), 3.86 (dd, J=8.4, 15.0 Hz, 1H), 4.37 (dd, J=9.9, 15.0 Hz, 1H), 5.67 (dd, J=8.4, 9.9 Hz, 1H), 6.55 (d, J=3.3 Hz, 1H), 6.69 (s, 2H), 7.42 (d, J=3.3 Hz, 1H), 7.53 (d, J=8.7 Hz, 1H), 7.78 (dd, J=1.5, 9.0 Hz, 1H), 8.16 (s, 1H).

EXAMPLE 7

2-(indol-3-yl)-5-(3,4,5-trimethoxyphenyl)-Δ2,3-oxazoline

3-Indolecarboxylic acid was processed as described in Example 11 to provide the desired product.

MS (DCVN$_3$) m/z 353 (M+H)$^+$;

$^1$H NMR (300 MHz, CDCl$_3$) δ 3.85 (s, 6H), 3.86 (s, 3H), 4.04 (dd, J=8.4, 15.0 Hz, 1H), 4.51 (dd, J=9.9, 15.0 Hz, 1H), 5.56 (dd, J=8.4, 9.9 Hz, 1H), 6.62 (s, 2H), 7.24–7.33 (m, 2H), 7.45 (m, 1H), 7.92 (brs, 1H), 8.26 (m, 1H), 8.70 (brs, 1H).

EXAMPLE 8

2-(indol-2-yl)-5-(3,4,5-trimethoxyphenyl)-Δ2,3-oxazoline

2-Indolecarboxylic acid was processed as described in Example 11 to provide the desired product.

MS (DCI/NH$_3$) m/z 353 (M+H)$^+$;

$^1$H NMR (300 MHz, CDCl$_3$) δ 3.86 (s, 9H), 4.03 (dd, J=8.4, 15.0 Hz, 1H), 4.49 (dd, J=9.9, 15.0 Hz, 1H), 5.65 (dd, J=8.4, 9.9 Hz, 1H), 6.58 (s, 2H), 7.12–7.18 (m, 2H), 7.29 (td, J=0.9, 7.5 Hz, 1H), 7.40 (d, J=7.5 Hz, 1H), 7.68 (d, J=7.5 Hz, 1H), 9.33 (brs, 1H).

EXAMPLE 9

2-(1-methoxymethylindol-5-yl)-5-(3,4,5-trimethoxyphenyl)-Δ2,3-oxazoline

Example 11 was processed as described in Example 6 (substituting chloromethyl methyl ether for methyl iodide)to provide the desired product.

MS (DCI/NH$_3$) m/z 397 (M+H)$^+$;

$^1$H NMR (300 MHz, CDCl$_3$) δ 3.26 (s, 3H), 3.86 (s, 9H), 4.08 (brm, 1H), 4.52 (brm, 1H), 5.47 (s, 2H), 5.68 (brm, 1H), 6.57–6.67 (m, 3H), 7.24 (m, 1H), 7.54 (brm, 1H), 8.02 (brm, 1H), 8.41 (brm, 1H).

EXAMPLE 10

2-(4-amino-3-methoxyphenyl)-5-(3,4,5-trimethoxyphenyl)-Δ2,3-oxazoline

EXAMPLE 10A 2-(4-nitro-3-methoxyphenyl)-5-(3,4,5-trimethoxyphenyl)-Δ2,3-oxazoline 4-Nitro-3-methoxybenzoic acid was processed as described for 5-indolecarboxylic acid in Example 11 to provide the desired product.

EXAMPLE 10B 2-(4-amino-3-methoxyphenyl)-5-(3,4,5-trimethoxyphenyl)-Δ2,3-oxazoline A solution of Example IOA (90 mg, 0.23 mmol) in a mixture of 1:1 THF/H$_2$O (2 mL) was treated with excess KCO$_3$ and Na$_2$S$_2$O$_4$, stirred at room temperature for 18 hours, treated with water, and extracted with ethyl acetate. The extract was washed with brine and dried (Na$_2$SO$_4$), filtered, and concantrated. The concentrate was purified by prepative thin layer chromatography to provide 12 mg of the desired product.

MS (DCI/NH$_3$) m/z 359 (M+H)$^+$;

$^1$H NMR (300 MHz, CDCl$_3$) δ 3.84 (s, 3H), 3.86 (s, 6H), 3.94 (s, 3H), 4.00 (dd, J=8.7, 15.0 Hz, 1H), 4.45 (dd, J=9.6, 15.0 Hz, 1H), 5.59 (dd, J=8.7, 9.6 Hz, 1H), 6.58 (s, 2H), 6.70 (d, J=8.1 Hz, 1H), 7.51 (d, J=9.0 Hz, 1H), 7.58 (brs, 1H).

EXAMPLE 11

2-(indol-5-yl)-5-(3,4,5-trimethoxyphenyl)-Δ2,3-oxazoline

EXAMPLE 11A

N-(hydroxy(3,4,5-trimethoxyphenyl)methyl)-1H-indole-5-carboxamide

A solution of 5-indolecarboxylic acid (2.0 g, 12.4 mmol) in DMF (25 mL) at room temperature was treated portionwise with 1,1'-carbonyldiimidazole (2.1 g, 13.0 mmol). In a separate reaction, a suspension of β-hydroxyamine acetic acid salt (3.92 g, 13.7 mmol) in DMF (20 mL) was treated with diisopropylethylamine (5.0 mL, 28.7 mmol) and DMAP (30.3 mg, 0.25 mmol). When the suspension of β-hydroxyamine vanished, the imidazolide solution was transferred dropwise to the β-hydroxyamine solution. The pink solution was stirred at room temperature for 3 hours, treated with water (100 mL), and adjusted to pH 5.5 with 3N HCl to cause precipitation of white solid. The solid was filtered, washed with cold water and dried in a vacuum oven to provide 3.7 g of the desired product as a white solid.

EXAMPLE 11B (5R) 2-(indol-5-yl)-5-(3,4,5-trimethoxyphenyl)-Δ2,3-oxazoline

A solution of Example 11A (200 mg, 0.54 mmol) in THF (10 mL) was treated with Burgess Reagent (142 mg, 0.60 mmol), refluxed 1 hour, cooled, and partitioned between ethyl acetate and brine. The organic layer was dried (Na$_2$SO$_4$), filtered, and concentrated. The concentrate was purified by flash column chromatography on silica gel with 1:1 hexanes/ethyl acetate to provide 120 mg of the desired product as a light yellow solid.

MS (DCI/NH$_3$) mlz 353 (M+H)$^+$;

$^1$H NMR (300 MHz, CDCl$_3$) δ 3.86 (s, 9H), 4.04 (dd, J=8.7, 15.0 Hz, 1H), 4.50 (dd, J=9.9, 15.0 Hz, 1H), 5.63 (dd, J=8.7, 9.9 Hz, 1H), 6.61 (s, 2H), 6.64 (m, 1H), 7.28 (t, J=3.0 Hz, 1H), 7.46 (d, J=9.7 Hz, 1H), 7.95 (dd, J=1.8, 9.7 Hz, 1H), 8.37 (s, 1H), 8.43 (brs, 1H).

EXAMPLE 12

2-(4-amino-3-methylphenyl)-5-(3,4,5-trimethoxyphenyl)-Δ2,3-oxazoline 4-amino-3-methylbenzoic acid was processed as described for 5-indolecarboxylic acid in Example 11 to provide the desired product.

MS (DCI/NH$_3$) m/z 343 (M+H)$^+$;

$^1$H NMR (300 MHz, CDCl$_3$) δ 2.19 (s, 3H), 3.84 (s, 9H), 3.95 (dd, J=8.7, 15.0 Hz, 1H), 4.41 (dd, J=9.9, 15.0 Hz, 1H), 5.53 (dd, J=8.7, 9.9 Hz, 1H), 6.57 (s, 2H), 6.68 (d, J=8.7 Hz, 1H), 7.69–7.77 (m, 2H);

Anal. calcd for C$_{19}$H$_{22}$N$_2$O$_4$ 0.10 CH$_3$C(O)OCH$_2$CH$_3$:C, 66.35; H, 6.54; N, 7.98. Found: C, 66.56; H, 6.57; N, 7.70.

Using the procedures described herein, Examples 13–15 were prepared.

EXAMPLE 13

2-(3-hydroxy-4-methovphenyl)-4-dimethyl-5-(3,4,5-trimethoxyphenyl)-Δ2,3-oxazoline MS (DCI/NH$_3$) m/z 372 (M+H)$^+$;

$^1$H NMR (CDCl$_3$) δ 7.91–7.88 (m, 2H), 6.71–6.67 (m, 2H), 6.52 (s, 2H), 5.16 (s, 1H), 3.85 (s, 3H), 3.84 (s, 6H), 3.03 (s, 6H), 1.53 (s, 3H), 0.88 (s, 3 H).

EXAMPLE 14

2-(N-methyl-tetrahydroquinol-6-yl)-5-(3,4,5-trimethoxyphenyl)-Δ2,3-oxazoline

MS (DCI/NH$_3$) m/z 383 (M+H)$^+$;

$^1$H NMR (CDCl$_3$) δ 7.87–7.83 (in, 1H), 7.73–7.69 (m, 1H), 6.57–6.53 (in, 3H), 5.63–5.58 (in, 1H), 4.48–4.40 (in, 1H), 4.04–3.97 (in, 1H), 3.85 (s, 9H), 3.37–3.33 (in, 2H), 2.98 (s, 3H), 2.81–2.77 (in, 2H), 2.01–1.94 (in, 2 H).

EXAMPLE 15

2-(2-methyl-cvclopropyl)-5-(3,4,5-trimethoxyphenyl)-Δ2,3-oxazoline MS (DCI/NH$_3$) m/z 292 (M+H)$^+$;

$^1$H NMR (CDCl$_3$) δ 6.62 (s, 2H), 5.93–5.90 (in, 1H), 4.99–4.94 (in, 1H), 3.87 (s, 6H), 3.85 (s, 3H), 3.64–3.50 (in, 1H), 1.61 (bs, 1H), 1.42–1, 05 (in, 5H), 0.63–0.58 (in, 1 H).

EXAMPLE 16

2-(4-ethoxyphenyl)-5-(3,4,5-trimethoxyphenyl)-Δ2,3-oxazoline

EXAMPLE 16A 4-ethoxy-N-[2-hydroxy-2-(3,4,5-trimethoxyphenyl)ethyl]benzamide

4-Ethoxybenzoic acid was processed as described in Example 4 to provide the desired product. HPLC retention time: 4.3 minutes with 1:4 acetonitrile/aqueous ammonium acetate and 10 minutes with 95:5 acetonitrile/aqueous ammonium acetate. (APCI(+)) m/z 376 (M+H)$^+$ and 358 (M+H–18)$^+$.

EXAMPLE 16B 2-(4-ethoxyphenyl)-5-(3,4,5-trimethoxyphenyl)-Δ2,3-oxazoline

A solution of Example 16A in THF was treated with treated with (methoxycarbonylsulfamoyl) triethylammonium hydroxide (Burgess Reagent, 1.1 equivalents) in THF, heated at 70° C. for three days, cooled, and concentrated. The residue was purified by preparative reverse phase HPLC to provide the desired product. HPLC retention time: 6.57 minutes using the HPLC gradient system described in Example 16A.

MS (APCI(+)) mn/z 358 (M+H)$^+$.

EXAMPLE 17

2-(3,4-dimethoxyphenyl)-5-(3,4,5-trimethoxyphenyl)-Δ2,3-oxazoline

EXAMPLE 17A

N-(2-hydroxy-2-(3,4,5-trimethoxyphenyl)ethyl)-3.4-dimethoxybenzamide 3,4-Dimethoxybenzoic acid was processed as described in Example 4 to provide the desired product. HPLC retention time: 3.5 minutes using the conditions described in Example 16A.

MS (APCI(+)) m/z 392 (M+H)$^+$ and 374 (M+H–18)$^+$.

EXAMPLE 17B 2-(3.4-dimethoxyphenyl)-5-(3,4,5-trimethoxyphenyl)-Δ2,3-oxazoline Example 17A was processed as described in Example 16 to provide the desired product. HPLC retention time: 5.72 minutes using conditions as described in Example 16A.

MS (APCI(+)) m/z 374 (M+H)$^+$.

EXAMPLE 18

2-(4-benzyloxy-3-methoxyphenyl)-5-(3,4,5-trimethoxyphenyl)-Δ2,3-oxazoline

EXAMPLE 18A 4-(benzyloxy)-N-[2-hydroxy-2-(3,4,5-trimethoxyphenyl)ethyl]-3-methoxybenzamide 4-Benzyloxy-3-methoxybenzoic acid was processed as described in Example 4 to provide the desired product. HPLC retention time: 4.6 minutes using the conditions described in Example 16A.

MS (APCI(+)) 468 (M+H)$^+$ and 450 (M+H–18).

EXAMPLE 18B 2-(4-benzyloxy-3-methoxyphenyl)-5-(3,4,5-trimethoxyphenyl)-Δ2,3-oxazoline Example 18A was processed as described in Example 16 to provide the desired product. HPLC retention time: 7.07 minutes using conditions as described in described in Example 16A.

MS (APCI(+)) 450 (M+H)$^+$.

EXAMPLE 19

2-(2,3-dihydro-5-bromo-7-benzofuranyl)-5-(3,4,5-trimethoxyphenyl)-Δ2,3-oxazoline

EXAMPLE 19A 5-bromo-N-(2-hydroxy-2-(3,4,5-trimethoxyphenyl)ethyl)-2,3-dihydro-1-benzofuran-7-

2,3-Dihydrobenzofuran-5-bromo-7-carboxylic acid was processed as described in Example 4 to provide the desired product. HPLC retention time: 4.5 minutes using the conditions described in Example 16A.

MS (APCI(+)) m/z 454 (M+H)$^+$ and 436 (M+H–18)$^+$.

EXAMPLE 19B 2-(2,3-dihydro-5-bromo-7-benzofuranyl)-5-(3,4,5-trimethoxyphenyl)-Δ2,3-oxazoline Example 19A was processed as described in Example 16 to provide the desired product. HPLC retention time: 6.65 minutes using the conditions described in Example 16A.

MS (APCI(+)) m/z 436 (M+H)$^+$.

EXAMPLE 20

2-(3-acetoxy-4-methoxyphenyl)-5-(3,4,5-trimethoxyphenyl)-Δ2,3-oxazoline

EXAMPLE 20A 5-(((2-hydroxy-2-(3,4,5-trimethoxyphenyl)ethyl)amino))carbonyl)-2-methoxyphenl A solution of 3-acetoxy-4-methoxybenzoic acid 392 mg, 1.86 mmol) in dichloromethane (10 mL) and DMF (1 drop) at 0° C. was treated with oxalyl chloride (0.33 mL), warmed to room temperature, stirred for 1 hour, and concentrated. The concentrate was dissolved in toluene and concentrated to provide a yellow solid. This concentrate was dissolved in pyridine (5 mL), cooled to 0° C. and treated with 2-amino-1-(3,4,5-trimethoxyphenyl)ethanol, acetic acid salt (536 mg, 1.86 mmol), stirred for 18 hours while warming to room temperature, diluted with ethyl acetate, and washed sequentially with 1M sodium bisulfate (2×), water (1×), 10% NaHCO$_3$, and brine, dried (MgSO4), filtered, and concentrated to provide 297 mg of the desired product.

MS (ESI(+)) m/z 420 (M+H)$^+$;

$^1$H NMR (300 MHz, CDCl$_3$) δ 7.66 (dd, J=2.2, 8.5, 1H), 7.49 (d, J=2.2, 1H), 7.00 (d, J=8.5, 1H), 6.63 (s, 2H), 6.45 (m, 1H), 4.90 (m, 1H), 3.9 (m, 1H), 3.89 (s, 3H), 3.86 (s, 6H), 3.84 (s, 3H), 3.51 (m, 1H), 2.33 (s, 3H).

EXAMPLE 20B 2-(3-acetoxy-4-methoxyphenyl)-5-(3,4,5-trimethoxyphenyl)-Δ2,3-oxazoline A solution of Example 20A (290 mg, 0.69 mmol) in chloroform (10 mL) at 0° C. was treated with thionyl chloride (0.1 mL, 1.38 mmol), stirred for 40 minutes, warmed to room temperature, stirred for 1 hour, poured into 10% NaHCO$_3$, and extracted with dichloromethane (2×). The extracts were dried (MgSO$_4$), filtered, and concentrated. The concentrate was purified by flash chromatography on silica gel with 1:1 hexanes/ethyl acetate to provide 137 mg of the desired product as an off-white solid.

MS (DCI/NH$_3$) m/z 402 (M+H)$^+$;

$^1$H NMR (300 MHz, CDCl$_3$) δ 7.64 (dd, J=2.0, 8.5, 1H), 7.47 (d, J=2.0, 1H), 7.00 (d, J=8.5, 1H), 6.65 (s, 2H), 6.37 (m, 1H), 5.07 (dd, J=5.4, 8.8, 1H), 4.07 (m, 1H), 3.88 (s, 3H), 3.86 (s, 6H), 3.85 (s, 3H), 3.76 (m, 1H), 2.33 (s, 3H).

EXAMPLE 21

2-(1-methyl-2,3-dihydro-indol-5-yl)-5-(3,4,5-trimethoxyphenyl)-Δ2,3-oxazoline

EXAMPLE 21A 1-methyl-2,3-dihydro-indole-5-carboxylic acid (N-[2-hydroxy-2-(3,4,5-trimethoxyphenyl) ethyl])amide A suspension of indole-5-carboxylic acid, (N-[2-hydroxy-2-(3,4,5-trimethoxyphenyl)ethyl]) amide (207 mg, 0.56 mmol) and paraformaldehyde (168 mg, 5.6 mmol) in acetic acid (5 mL) was treated with sodium cyanoborohydride (176 mg, 2.79 mmol), stirred for 18 hours, and concentrated. The concentrate was partitioned between ethyl acetate and 10% NaHCO$_3$, washed sequentially with 10% NaHCO$_3$ and brine, dried (MgSO$_4$), filtered, and concentrated to provide 218 mg of the desired product. MS (ESI(+)) m/z 387 (M+H)$^+$;

$^1$H NMR (300 MHz, CDCl$_3$) δ 7.51 (m, 2H), 6.63 (s, 2H), 6.38 (d, J=8.1, 1H), 4.90 (m, 1H), 3.85 (m, 10H), 3.5 (m, 1H), 3.45 (t, J=8.5, 2H), 3.14 (s, 1H), 2.99 (t, J=8.5, 2H), 2.82 (s, 3H).

EXAMPLE 21B 2-(1-methyl-2,3-dihydro-indol-5-yl)-5-(3,4,5-triethoxyphenyl)-Δ2,3-oxazoline A solution of Example 21A (151 mg, 0.39 mmol) in THF (5 mL) was treated with Burgess' Reagent (102 mg, 0.43 mmol), heated to reflux for 1.5 hours, cooled, poured into 10% NaHCO$_3$ and extracted twice with dichloromethane. The extracts were dried (MgSO$_4$), filtered, and concentrated. The concentrate was purified by flash column chromatography on silica gel with 1:1 ethyl acetate/hexanes to provide 25 mg of the desired product.

MS (DCI/NH$_3$) m/z 369 (M+H)$^+$;

$^1$H NMR (300 MHz, CDCl$_3$) δ 7.92 (dd, J=1.7, 8.5, 1H), 7.73 (d, J=1.4, 1H), 6.58 (s, 2H), 6.38 (d, J=8.5, 2H), 5.70 (app t, J=9.2, 1H), 4.53 (dd, J=10.2, 13.2, 1H), 4.22 (dd, J=8.5, 12.9, lH), 3.88 (s, 6H), 3.86 (s, 3H), 3.59 (t, J=8.5, 2H), 3.06 (t, J=8.5, 2H), 2.90 (s, 3H).

EXAMPLE 22

2-(1-methylindol-5-yl)-5-(3,4,5-trimethoxyphenyl)-Δ2,3-oxazoline, hydrochloride

A solution of Example 6 (848 mg, 2.31 mmol) in a mixture of dioxane (15 mL), ether (15 mL), and dichloromethane (5 mL) was treated with 4M HCl in dioxane (0.6 mL, 2.4 mmol) to form a precipitate. The suspension was diluted with hexanes, cooled to 5° C., and filtered to provide 635 mg of the desired product.

$^1$H NMR (300 MHz, CD OD) 6 8.48 (d, J=1.4, lH), 7.90 (dd, J=1.7, 8.8, lH), 7.69 (d, J=8.8, 1 H), 7.46 (d, J=3.4, 1H), 6.93 (s, 2H), 6.74 (dd, J=0. 7, 3. 1, i H), 6.40 (dd, J=9.8, 10.2, 1H), 4.67 (dd, J=10.2, 11.9, 1H), 4.31 (dd, J=9.8, 11.9, 1H), 3.91 (s, 3H), 3.87 (s, 6H), 3.79 (s, 3H);

Anal. calcd for C$_{21}$H$_{23}$ClN$_2$O$_4$:C, 62.61 H, 5.75; N, 6.95. Found: C, 62.86; H, 5.76; N, 6.95.

EXAMPLE 23

(5S)-2-(1-methylindol-5-yl)-5-(3,4,5-trimethoxyphenyl)-Δ2,3-oxazoline

EXAMPLE 23A 3,4,5-trimethoxystyrne

A suspension of methyltriphenylphosphonium bromide (86 g, 241 mmol) in THF (250 mL) was treated with 2.5M n-butyllithium in hexanes (96 mL, 240 mmol), stirred for 30 minutes, treated with 3,4,5-trimethoxybenzaldehyde (43 g, 219 mmol) stirred at room temperature for 1 hour, treated with water, and extracted with diethyl ether. The extract was washed with brine, dried (MgSO$_4$), filtered, and concentrated. The concentrate was purified by Kugelrohr distillation (130° C. at 1 mm Hg) to provide 27.2 g (64%) of the desired product as a colorless oil.

EXAMPLE 23B (1S)-2-hydroxy-1-(3,4,5-trimethoxyphenyl)ethanol

A mechanically stirred solution of AD-mix-α (50 g) in 1:1 tert-butanol:water (60 mL) at 0° C. was treated dropwise with 3,4,5-trimethoxystyrene (7.5 g, 38.6 mmol), stirred at 0° C. for 3 hours and at room temperature for 18 hours, treated with Na$_2$SO$_3$ (50 g), stirred for 30 minutes, diluted with water, and extracted with ethyl acetate (3×). The combined extracts were washed with water (1×) and brine (1×), dried (MgSO$_4$), filtered, and concentrated. The concentrate was purified by flash column chromatography on silica gel with 40:60:4 hexanelethyl acetate/methanol to provide 5.7 g (65%) of the desired product as a colorless oil that solidified upon standing.

$[α]_D^{24}$=+34.9° (c 2.09, CHCl$_3$);

Lit. $[α]_D$=+36.920 (c 2.13, CHCl$_3$). (Tet. Asym.,1996, 7(4) 1101–1104).

EXAMPLE 23C (1 S)-2-(4-methylbenzenesulfonyloxy)-1-(3,4,5-trimethoxyphenyl)ethanol A solution of Example 23B (460 mg, 2.0 mmol) in pyridine (2 mL) at 0° C. was treated with para-toluenesulfonyl chloride (384 mg; 2.0 mmol), stirred at 0° C. for 2 hours, treated with 10% HCl, and extracted with diethyl ether. The extract was washed with water (2×) and brine (1×), dried (MgSO$_4$), filtered, and concentrated to provide 470 mg (61%) of the desired product as a colorless oil which was used in the next step without further purification.

EXAMPLE 23D (1S)-2-azido-1-(3,4,5-trimethoxyphenyl)ethanol

A solution/slurry of Example 23C (450 mg; 1.2 mmol) and sodium azide (153 mg; 2.4 mmol) in DMF (5 mL) was heated at 80–90° C. for 2 hours, treated with brine, and extracted with ethyl acetate. The extract was washed with brine (2×), dried (MgSO$_4$), filtered, and concentrated. The concentrate was purified by flash chromatography on silica gel with 30% ethyl acetate/hexane) to provide 223 mg (75%).the desired product as a nearly colorless oil.

EXAMPLE 23E (1S)-2-amino-1-(3,4,5-trimethoxyphenyl)ethanol

A mixture of Example 23D (253 mg; 1.0 mmol) and 10% Pd/C (50 mg) in ethanol (7 mL) was stirred for 18 hours under hydrogen (balloon), filtered through diatomaceous earth (Celite®), and concentrated. The concentrate was redissolved in ethanol, filtered again through diatomaceous earth, and concentrated to provide 216 mg (95%) of the desired product as an off-white solid which was used in the next step without further purification.

$[α]_D^{24}$=+38.0° (c 1.51, CHCl$_3$).

EXAMPLE 23F (5S)-2-(1-methylindol-5-yl)-5-(3,4,5-trimethoxyphenyl)-Δ2,3-oxazoline A suspension of Example 23E (3.41 g, 15.0 mmol), N-methyl-5-cyanoindole (3.75 g, 24.0 mmol) K$_2$CO$_3$ (320 mg, 2.3 mmol) in mixture of ethylene glycol (4.8 mL) and glycerol (2.6 mL) was heated to 140° C. under nitrogen for 40 hours, cooled to room temperature, treated with dichloromethane, washed sequentially with water and brine, dried (MgSO$_4$), filtered, and concentrated. The concentrate was purified by flash column chromatography on silica gel with 60:40 ethyl acetate/hexane to provide 3.72 g (68%) of the desired product as white solid.

$[\alpha]_D^{24}$=+195.70 (c 1.04, CH$_2$Cl$_2$);

MS (DCI/NH$_3$) m/z 367 (M+H)$^+$;

$^1$H NMR (CDCl$_3$) δ 8.34 (d, J=3.0 Hz, 1H), 7.94 (dd, J=3.0, 12.0 Hz, 1H), 7.38 (d, J=9.0 Hz, 1H), 7.12 (d, J=6.0 Hz, 1H), 6.62 (s, 2H), 6.57 (d, J=3.0 Hz, 1H), 5.62 (dd, J=9.0, 12.0 Hz, 1H), 4.48 (dd, J=9.0, 12.0, 1H), 4.02 (m, 1H), 3.86 (s, 6H), 3.85 (s, 3H).

EXAMPLE 24

(5S)-2-(1-methylindol-5-yl)-5-(3,4,5-trimethoxyphenyl)-Δ2,3-oxazoline hydrochloride A solution of of Example 23 (3.73 g, 10.2 mmol) in dichloromethane (67 mL) and diethyl ether (67 mL) was treated with 4M HCl in dioxane (2.8 mL), stirred for 30 minutes, treated with diethyl ether (200 mL), and cooled in a refrigerator for 20 minutes.

The resulting precipitate was filtered, washed with ether, and dried under vacuum to provide 3.8 g (93%) of the desired compound as a white solid. $[\alpha]_D^{24}$=+42.70 (c 0.995, CH$_3$OH).

EXAMPLE 25

(5R)-2-(1-methylindol-5-yl)-5-(3,4,5-trimethoxyphenyl)-Δ2,3-oxazoline

Example 23A and AD-mixβ, were processed as described in Example 23B to provide the desired product as white solid.

$[\alpha]_D^{24}$=184.5° (c 1.04, CH$_2$Cl$_2$);

MS (DCI/NH$_3$) m/z 367 (M+H)$^+$;

$^1$H NMR (CDCl$_3$) δ 8.32 (d, J=3.0 Hz, 1H), 7.93 (dd, J=3.0, 12.0 Hz, 1H), 7.38 (d, J=9.0 Hz, 1H), 7.12 (d, J=6.0 Hz, 1H), 6.62 (s, 2H), 6.57 (d, J=3.0 Hz, 1H), 5.59 (dd, J=9.0, 12.0 Hz, 1H), 4.48 (dd, J=9.0, 12.0, 1H), 4.00 (m, 1H), 3.86 (s, 6H), 3.85 (s, 3H).

The appropriately substituted acids or nitriles were processed as described in Example 6, Example 11, or Example 23, to prepare the following compounds:

EXAMPLE 26

2-(1-ethylindol-5-yl)-5-(3,4,5-trimethoxyphenyl)-Δ2,3-oxazoline

MS (ESI(+)) m/z 381 (M+H)$^+$;

$^1$H NMR (CDCl$_3$) δ 8.35 (s, 1H), 7.97 (m, 1H), 7.45 (dd, J=12. 1H), 7.18 (d, J=3.0 Hz, 1H), 6.61 (s, 2H), 6.58 (d, J=3.0 Hz, 1H), 5.65 (br s, 1H), 4.50 (br s, 1H), 4.20 (q, J=7.0 Hz, 2H), 4.05 (br s, 1H), 3.85 (s, 9H), 1.5 (t, J=7 Hz, 3H).

EXAMPLE 27

2-(6-indolyl)-5-(3,4,5-trimethoxyphenyl)-Δ2,3-oxazoline

MS (ESI(+)) m/z 353 (M+H)$^+$;

$^1$H NMR (CDCl$_3$) δ 8.53 (br s, 1H), 8.3 (br s, 1H), 7.8 (m, 1H), 7.7 (m, 1H), 7.38 (d, J=3.0 Hz, 1H), 6.60 (m, 1H), 5.66 (br s, 1H), 4.5 (br s, 1H), 4.05 (br s, 1H), 4.10 (br s, 1H), 3.85 (s, 9H).

EXAMPLE 28

2-(1-methylindol-6-yl)-5-(3 4.5-trimethoxyphenyl)-Δ2,3-oxazoline MS (ESI(+)) m/z 367 (M+H)$^+$;

$^1$H NMR (CDCl$_3$) δ 8.18 (br s, 1H), 7.79 (d, J=9.0 Hz, 1H), 7.65 (d, J=9.0 Hz, 1H), 7.18(d, J=4.0 Hz, 1H), 6.60 (s, 2H), 6.52 (d, J=4.0 Hz, 1H), 5.65 (br s, 1H), 4.50 (br s, 1H), 4.05 (br s, 1H), 4.10 (br s, 1H), 3.85 (s, 9H).

EXAMPLE 29

2-(4-indolyl)-5-(3,4,5-trimethoxyphenyl)-Δ2,3-oxazoline

MS (ESI(+)) m/z 353 (M+H)$^+$;

$^1$H NMR (CDCl$_3$) δ 8.38 (br s, 1H), 7.88 (d, J=9.0 Hz, 1H), 7.55 (d, J=9.0 Hz, 1H), 7.25–7.35 (m, 2H), 6.62 (s, 2H), 5.62 (m, 1H), 4.55 (m, 1H), 4.15 (m, 1H), 3.86 (s, 3H), 3.84 (s, 6H).

EXAMPLE 30

2-(1-methylindol-4-yl)-5-(3,4,5-trimethoxyphenyl)-Δ2,3-oxazoline MS (ESI(+)) m/z 367 (M+H)$^+$;

$^1$H NMR (CDCl$_3$) δ 7.84 (d, J=9.0 Hz, 1H), 7.50 (d, J=9.0 Hz, 1H), 7.28 (m, 1H), 7.18 (m, 2H), 6.62 (s, 2H), 5.62 (dd, J=9.0, 12.0 Hz, 1H), 4.55 (dd, J=12.0, 15.0 Hz, 1H), 4.08 (dd, J=9.0,15.0 Hz, 1H), 3.85 (s, 3H), 3.83 (s, 6H).

EXAMPLE 31

2-(7-indolyl)-5-(3,4,5-trimethoxyphenyl)-Δ2,3-oxazoline MS (ESI(+)) m/z 353 (M+H)$^+$;

$^1$H NMR (CDCl$_3$) δ 10.38 (br, 1H), 7.79 (dd, J=9.0, 15.0 Hz, 1H), 7.32 (t, J=3.0 Hz, 1H), 7.15 (t, J=9.0 Hz, 1H), 6.61 (m, 1H), 6.60 (s, 2H), 5.62 (dd, J=9.0, 12.0 Hz, 1H), 4.55 (dd, J=12.0, 15.0 Hz, 1H), 4.05 (dd, J=9.0, 15.0 Hz, 1H), 3.85 (s, 9H).

EXAMPLE 32

2-(1-methylindol-7-yl)-5-(3,4,5-trimethoxyphenyl)-Δ2,3-oxazoline

MS (ESI(+)) m/z 367 (M+H)$^+$;

$^1$H NMR (CDCl$_3$) δ 7.73 (d, J=9.0 Hz, 1H), 7.61 (d, J=3.0 Hz, 1H), 7.11 (t, J=7.0 Hz, 1H), 7.05 (d, J=6.0 Hz, 1H), 6.60 (s, 2H), 6.55 (d, J=3.0, 1H), 5.65 (m, 1H), 4.50 (m, 1H), 4.09 (m, 1H), 3.93 (s, 3H), 3.86 (s, 6H), 3.85 (s, 3H).

EXAMPLE 33

2-(1-methylindol-3-yl)-5-(3,4,5-trimethoxyphenyl)-Δ2,3-oxazoline

MS (ESI(+)) m/z 367 (M+H)$^+$;

$^1$H NMR (CDCl$_3$) δ 8.24 (m, 1H), 7.8 (m, 1H), 7.40–7.25 (m, 3H), 6.61 (s, 2H), 5.58–5.52 (m, 1H), 4.50 (dd, J=9.8, 14.2 Hz, 1H), 4.03 (dd, J=8.1, 14.2 Hz, 1H), 3.86 (s, 3H), 3.85 (s, 3H), 3.84 (s, 6H);

Anal. calcd for C$_{21}$H$_{22}$N$_2$O$_4$: C, 68.84; H, 6.05; N, 7.65. Found: C, 68.56; H, 6.07; N, 7.68.

EXAMPLE 34

2-(1-methyl-indol-2-yl)-5-(3,4,5-trimethoxyphenyl)-Δ2,3-oxazoline $^1$H NMR (CDCl$_3$) δ 7.69 (d, J=8.1 Hz, 1H), 7.42–7.31 (m, 3H), 6.59 (s, 2H), 5.60 (m, 1H), 4.54 (m, 1H), 4.16 (s, 3H), 4.13–4.06 (m, 1H), 3.86 (s, 6H), 3.85 (s, 3H); HRMS (FAB) Calc. (M+H)$^+$ for C$_{21}$H$_{23}$N$_2$O$_4$: 367.1658. Found: 367.1663.

EXAMPLE 35

2-(6-guinolinvl)-5-(3,4,5-trimethoxyphenyl)-Δ2,3-oxazoline

MS (ESI(+)) m/z 365 (M+H)$^+$;
$^1$H NMR (CDCl$_3$) δ 9.10 (br s, 1H), 8.55 (br s, 1H), 8.20–8.53 (m, 3H), 7.50 (br s, 1H), 6.60 (d, J=3.0 Hz, 1H), 7.11 (t, 1H), 7.50 (d, J=6.0 Hz, 1H), 6.60 (s, 2H), 5.68 (br s, 1H), 4.85 (br s, 1H), 4.10 (br s, 1H), 3.86 (s, 9H).

EXAMPLE 36

2-(3-quinolinyl)-5-(3,4,5-trimethoxyphenyl)-Δ2,3-oxazoline

MS (ESI(+)) m/z 365 (M+H)$^+$;
$^1$H NMR (CDCl$_3$) δ 9.52 (br s, 1H), 8.78 (br s, 1H), 8.20 (br d, J=9.0 Hz, 3H), 7.92 (d, J=9.0 Hz, 1H), 7.85 (t, J=7.0 Hz, 1H), 7.62 (t, J=7.0 Hz, 1H), 6.60 (s, 2H), 5.65 (m, 1H), 4.55 (m, 1H), 4.10 (m, 1H), 3.87 (s, 9H).

EXAMPLE 37

2-(4-guinolinyl)-5-(3,4,5-trimethoxyphenyl)-Δ2,3-oxazoline

MS (ESI(+)) m/z 365 (M+H)$^+$;
$^1$H NMR (CDCl$_3$) δ 9.25 (br s, 1H), 9.05 (br s, 1H), 8.05 (br s, 1H), 8.70–7.90 (m, 2H), 6.60 (s, 2H), 5.67 (m, 1H), 4.70 (m, 1H), 4.23 (m, 1H), 3.88 (s, 9H).

EXAMPLE 38

2-(1-isoquinolinyl)-5-(3,4,5-trimethoxyphenyl)-Δ2,3-oxazoline

MS (ESI(+)) m/z 365 (M+H)$^+$;
$^1$H NMR (CDCl$_3$) δ 9.21 (d, J=9.0 Hz, 1H), 8.68 (d, J=6.0 Hz, 1H), 7.68–7.92 (m, 4H), 6.68 (s, 2H), 5.73 (m, 1H), 4.68 (m, 1H), 4.28 (dd, J=9.0, 15.0 Hz, 1H), 3.86 (s, 6H), 3.84 (s, 3H).

EXAMPLE 39

2-(3-amino-4-methoxyphenyl)-5-(3,4,5-trimethoxyphenyl)-Δ2,3-oxazoline

EXAMPLE 39A 3-(9-fluorenylmethoxycarbonyl)amino-4-methoxybenzoic acid

A suspension of 3-amino-4-methoxybenzoic acid (1.00 g, 6.0 mmol) in acetone (15 mL) was treated portionwise and alternately with Fmoc-succinimide (2.63 g, 7.8 mmol) in acetone (15 mL) and saturated aqueous NaHCO$_3$ to keep the pH of the solution between 8–9, stirred at room temperature for 18 hours, treated with 3M HCl, and filtered. The solid was washed sequentially with water and dichloromethane and dried under vacuum to provide 1.54 g (66%) of the desired product.

$^1$H NMR (DMSO-d$_6$) δ 8.91 (s, 1H), 8.23 (br s, 1H), 7.93 (d, J=9.0 Hz, 2H), 7.7 (m, 3H), 7.45 (t, J=7.0 Hz, 2H), 7.35 (t, J=7.0 Hz, 2H), 7.14 (d, J=9.0 Hz, 1H), 4.25–4.42 (m, 3H), 3.91 (s, 3H).

EXAMPLE 39B

N-(3-(9-fluorenylmethoxycarbonyl)amino-4-methoxybenzoyl)-1-(3,4,5-trimethoxyphenyl)-2-aminoethanol A suspension of Example 39A (765 mg, 1.96 mmol) and ethanoamine (446 mg, 1.96 mmol) in THF (20 mL) and DMF (1.5 mL) at room temperature was treated sequentially with HATU (747 mg, 1.96 mmol) and N-methylmorpholine (0.22 mL), stirred at room temperature for 18 hours, and concentrated. The concentrate was dissolved in dichloromethane, washed with water, dried (MgSO$_4$), filtered, and concentrated to provide 981 mg (84%) of the desired product.

MS (ESI(+)) m/z 621 (M+Na)$^+$;
$^1$H NMR (CDCl$_3$) δ 8.46 (br s, 1H), 7.80 (d, J=9.0 Hz, 2H), 7.63 (m, 3H), 7.30–7.48 (m, 4H), 6.95 (d, J=9.0 Hz, 1H), 6.63 (s, 3H), 6.60 (m, 1H), 4.90 (m, 1H), 4.51 (d, J=9.0 Hz, 2H), 4.30 (t, J=6.0 Hz, 1H), 3.84 (s, 9H), 3.82 (s, 3H).

EXAMPLE 39C 2-(3-(9-fluorenylmethoxycarbonyl)amino-4-methoxyphenyl)-5-(3,4,5-trimethoxyphenyl)-Δ2,3-oxazoline Example 39B (980 mg, 1.63 mmol) was processed as described in Example 1C to provide 920 mg of the desired product.

EXAMPLE 39D 2-(3-amino-4-methoxyphenyl)-5-(3,4,5-trimethoxyphenyl)-Δ2,3-oxazoline A solution of Example 39C (500 mg, 0.86 mmol) in acetonitrile (5 mL) was treated with diethylamine, stirred at room temperature for 20 minutes, and concentrated. The concentrate was purified by flash column chromatography on silica gel with 95:6:0.5 cdichloromethane/methanol/ammonium hydroxide to provide 227 mg (74%) of the desired product.

MS (ESI(+)) m/z 359 (M+H)$^+$;
$^1$H NMR (CDCl$_3$) δ 7.4 (m, 2H), 6.81 (d, J=9.0 Hz, 1H), 6.58 (s, 2H), 5.55 (m, 1H), 4.42 (m, 1H), 3.95 (m, 1H), 3.90 (s, 3H), 3.83 (s, 9H).

EXAMPLE 40

2-(3-amino-4-methyphenyl)-5-(3,4,5-trimethoxyphenyl)-Δ2,3-oxazoline

3-Amino-4-methylbenzoic acid (910 mg, 6.0 mmol) was processed as described in Example 39 to provide 438 mg of the desired product.

MS (ESI(+)) m/z 343 (M+H)$^+$;
$^1$H NMR (CDCl$_3$) δ 7.35 (m, 2H), 7.12 (d, J=9.0 Hz, 1H), 6.55 (s, 2H), 5.53 (dd, J=9.0, 12.0 Hz, 1H), 4.42 (dd, J=12.0, 15.0 Hz, 1H), 3.95 (dd, J=9.0, 15.0 Hz, 1H), 3.84 (s, 9H), 3.17 (br s, 2H).

EXAMPLE 41

2-(3-(Ala-Ala-amino-4-methoxyphenyl)-5-(3,4,5-trimethoxyphenyl)-Δ2,3-oxazoline

EXAMPLE 41A

A suspension of compound of Example 39 (492 mg, 1.37 mmol) and Fmoc-Ala-Ala-OH (500 mg, 1.31 mmol) in THF (35 mL) was treated sequentially with HATU (547 mg, 1.43 mmol) and N-methylmorpholine (0.16 mL, 1.45 mmol), stirred at room temperature for 18 hours, and concentrated. The concentrate was dissolved in ethyl acetate, and the solution was washed sequentially with water, 1M NaHSO$_4$, saturated aqeous NaHCO$_3$, water, and brine, dried (MgSO$_4$), filtered, and concentrated. The concentrate was purified by by flash column chromatography on silica gel with 7:3 ethyl acetate/dichloromethane to provide 500 mg of the desited product.

EXAMPLE 41B 2-(3-(Ala-Ala-amino-4-methoxyphenyl)-5-(3,4,5-trimethoxyphenyl)-Δ2,3-oxazoline A solution of Example 41A (500 mg, 6.9 mmol) in acetonitrile (30 mL) was treated with diethylamine (6.0 mL), stirred for 20 minutes, and concentrated. The concentrate was purified by flash column chromatography with with 93:7:1 dichloromethane/methanol/ammonium hydroxide to provide 200 mg of the desired product.

MS (ESI(+)) m/z 501 (M+H)$^+$;
$^1$H NMR (CDC1) 6 8.93 (s, 1H), 8.46 (d, J=6.0 Hz, 1H), 7.76 (dd, J=3.0, 9.0 Hz, 1H), 7.15–7.25 (m, 2H), 6.91 (d, J=9.0 Hz, 1H), 6.56 (s, 2H), 5.53 (m, 1H), 4.62 (m, 1H), 4.43 (dd, J=9.0, 14.0 Hz, 1H), 3.98 (m, 1H), 3.94 (s, 3H), 3.84 (s, 6H0, 3.83 (s, 3H), 3.54 (m, 1H), 2.38 (s, 1H), 1.46 (d, J=9 Hz, 3H), 1.36 (d, J=9 Hz, 3H).

EXAMPLE 42

2-(3-(Ala-amino-4-methoxyphenyl)-5-(3,4,5-trimethoxyphenyl)-Δ2,3-oxazoline

Example 39 (302 mg, 0.842 mmol) and Fmoc-Ala—OH (250 mg, 0.803 mmol) were proceeded as described in Example 41 to provide 225 mg of the desired product.

MS (ESI(+)) m/z 430 (M+H)$^+$;
$^1$H NMR (CDCl$_3$) δ 9.84 (s, 1H), 9.03 (dd, J=3.0 9 Hz, 1H), 7.75 (dd, J=3.0, 9.0 Hz, 1H), 6.92 (d, J=9.0 Hz, 1H), 6.58 (d, J=3.0 Hz, 2H), 5.52 (dd, J=9.0, 12.0 Hz, 1H), 4.42 (dd, J=12, 15 Hz, 1H), 4.0 (m, 1H), 3.95 (s, 3H), 3.85 (s, 9H), 3.62 (m, 1H), 1.52 (d, J=6.0 Hz, 3H).

EXAMPLE 43

2-(3-((3-aminopfopionoyl)amino-4-methoxyphenyl)-5-(3,4,5-trimethoxyphenyl)-Δ2,3-oxazoline Example 39 (302 mg, 0.842 mmol) and Fmoc-β-Ala-OH (250 mg, 0.803 mmol) were processed as described in in Examples 41 to provide 176 mg of the desired product.

MS (ESI(+)) m/z 430 (M+H)$^+$;
$^1$H NMR (CDCl$_3$) δ 9.08 (s, 1H), 8.95 (s, 1H), 7.73 (dd, J=3.0, 6.0 Hz, 1H), 6.56 (s, 2H), 5.53 (m, 1H), 4.42 (m, 1H), 3.95 (m, 1H), 3.92 (s, 3H), 3.84 (s, 9H), 3.12 (t, J=3.0 Hz, 2H), 2.56 (t, J=3.0 Hz, 2H), 2.03 (br s, 2H).

EXAMPLE 44

2-(3-(Ser-amino-4-methoxyphenyl)-5-(3,4,5-trimethoxyphenyl)-Δ2,3-oxazoline

Example 39 (287 mg, 0.800 mmol) and Fmoc-Ser-OH (250 mg, 0.763 mmol) were processed as described in in Example 41 to provide 133 mg of the desired product.

MS (ESI(+)) m/z 446 (M+H)$^+$;
$^1$H NMR (CDCl$_3$) δ 9.90 (br d, 1H), 9.00 (m, 1H), 7.76 (dd, J=3.0, 9.0 Hz, 1H), 6.92 (dd, J=3.0, 9.0 Hz, 1H), 6.56 (d, J=3.0 Hz, 2H), 5.52 (m, 1H), 4.42 (m, 1H), 4.00 (m, 1H), 3.95 (s, 3H), 3.82 (s, 3H), 3.83 (s, 6H), 3.60 (m, 1H), 1.25 (br d, 1H).

EXAMPLE 45

2-(3-(Gly-amino-4-methoxyphenyl)-5-(3,4,5-trimethoxyphenyl)-Δ2,3-oxazoline

Example 39 and Fmoc-Gly-OH were processed as described in in Example 41 to provide the desired product.

MS (ESI(+)) m/z 416 (M+H)$^+$;
$^1$H NMR (CDCl$_3$) δ 9.78 (br s, 1H), 9.02 (d, J=3.0 Hz, 1H), 7.77 (dd, J=3.0, 9.0 Hz, 1H), 6.94 (d, J=9.0 Hz, 1H), 6.58 (s, 2H), 5.56 (dd, J=9.0, 12.0 Hz, 1H), 4.43 (dd, J=12.0, 15.0 Hz, 1H), 3.98 (dd, J=9.0, 15.0 Hz, 1H), 4.97 (s, 3H), 3.86 (s, 6H), 3.85 (s, 3H), 3.51 (s, 3H).

EXAMPLE 46

2-(1-Methyl-1H-pvridin-2-on-4-yl)-5-(3,4,5-trimethoxyphenyl)-Δ2,3-oxazoline

EXAMPLE 46A 1-methyl-1H-pyridin-2-one-4-carboxylic acid

A solution of N-methyl-4-methoxycarbonylpyridinium iodide (2.00 g, 7.16 mmol) in water (10 mL) at room temperature was treated sequentially with 14M sodium hydroxide (1.0 mL) and 1.8M K$_3$Fe(CN)$_6$ (1.5 mL), stirred for 4 hours, treated again with 1.8M K3Fe(CN)$_6$ once per hour for 4 hours, heated at 55° C. for one hour, cooled to room temperature, and treated with 6M HCl to pH 3. The precipitate was collected, washed with ether and dried under vacuum to provide 1.00 g of the desired product.

MS (ESI(+)) m/z 154 (M+H)$^+$;
$^1$H NMR (DMSO-d$_6$) δ 7.81 (d, J=7.0 Hz, 1H), 6.83 (d, J=3.0 Hz, 1H), 6.54 (dd, J=3.0, 7.0 Hz, 1H), 3.45 (s, 3H).

EXAMPLE 46B 2-(1-methyl-1H-pyridin-2-on-4-yl)-5-(3,4,5-trimethoxyphenyl)-Δ2,3-oxazoline Example 46A (363 mg, 2.37 mmol) was processed as described in Example 4 to provide 493 mg of the desired product.

MS (ESI(+)) m/z 345 (M+H)$^+$;
$^1$H NMR (CDCl$_3$) δ 7.34 (d, J=9.0 Hz, 1H), 7.13 (d, J=3 Hz, 1H), 6.73 (dd, J=3.0, 9.0 Hz, 1H), 5.62 (dd, J=9.0, 12.0 Hz, 1H), 4.48 (dd, J=12.0, 15.0 Hz, 1H), 4.10 (dd, J=9.0, 15.0 Hz, 1H), 3.86 (s, 6H), 3.84 (s, 3H), 3.58 (s, 3H).

EXAMPLE 47

2-(2-(2-hydroxyethyloxy)-4-pyridinyl)-5-(3,4,5-trimethoxyphenyl)-Δ2,3-oxazoline 2-(2-Hydroxyethoxy)isonicotinonitrile (350 mg, 2.6 mmol) was processed as described in Example 23F to provide 250 mg (28%) of the desired product.

MS (ESI(+)) m/z 375 (M+H)$^+$;
$^1$H NMR (CDCl$_3$) δ 8.73 (d, J=3.0 Hz, 1H), 8.20 (dd, J=3.0, 9.0 Hz, 1H), 6.86 (d, J=9.0 Hz, 1H), 6.53 (s, 2H), 5.58 (dd, J=9.0, 10.0 Hz,. 1H), 4.53 (m, 2H), 4.45 (dd, J=10.0, 15.0 Hz, 1H), 3.98 (m, 2H), 3.09 (t, J=6.0 Hz, 1H).

EXAMPLE 48

2-(imidazo[1,2-α]pyridin-6-yl)-5-(3,4,5-trimethoxyphenyl)-Δ2,3-oxazoline

EXAMPLE 48A methyl imidazo[1,2-α]pyridin-6-carboxylate

A solution of bromoacetaldehyde diethyl acetal (3.2 mL, 21.3 mmol) in 12M HCl (0.5 mL) and water (23 mL) was heated at 90° C. for 1 hour, cooled to room temperature, treated sequentially with NaHCO$_3$, (1.67 g, 20 mmol) and methyl 6-aminonicotinate (1.10 g, 7.0 mmol), heated at 60° C. for 30 minutes, cooled to room temperature, adjusted to pH 9, and extracted with ethyl acetate. The extract was washed with water, dried (MgSO$_4$), filtered, and concentrated. The concentrate was purified by flash column chromatography with 97.5:2.5 dichloromethane/methanol to provide 1.02 g (88%) of the desired product.

MS (DCI/NH$_3$) m/z 177 (M+H)$^+$;

$^1$H NMR (CDCl$_3$) δ 8.93 (s, 1H), 7.60–7.74 (m, 4H), 3.96 (s, 3H).

EXAMPLE 48B imidazo[1,2-α]pyridin-6-carboxylic acid

A mixture of Example 48A (100 mg, 0.56 mmol) and 1M lithium hydroxide (0.62 mL) in THF (2 mL) was stirred at room temperature for 30 minutes, treated with 1M HCl (0.62 mL), and concentrated. The concentrate was purified by a flash column chromatography with 85:10:5 dichloromethane/methanol/ammonium hydroxide to provide 68.4 mg (74%) of the tiltle compound.

MS (DCI/NH$_3$) m/z 163 (M+H)$^+$;

$^1$H NMR (D$_2$O) 6 9.15 (br s, 1H), 8.25 (d, J=12.0 Hz, 1H), 8.16 (br s, 1H), 7.92 (br s, 1H), 7.83 (d, J=12.0 Hz, 1H).

EXAMPLE 48C 2-(imidazo[1,2-α]pyridin-6-yl)-5-(3,4,5-trimethoxyphenyl)-Δ2,3-oxazoline Example 48B (550 mg, 0.34 mmol) was processed as described in Example 4 to provide 261 mg of the desired product.

MS (ESI(+)) m/z 354 (M+H)$^+$;

$^1$H NMR (CDCl$_3$) δ 8.83 (s, 1H), 7.65–7.95 (m, 4H), 6.55 (s, 2H), 5.62 (m, 1H), 4.50 (dd, J=9.0, 15.0 Hz, 1H), 4.05 (dd, J=9.0, 15.0 Hz, 1H), 3.88 (s, 6H), 3.86 (s, 3H), 3.65 (s, 3H).

EXAMPLE 49

2-(imidazo[1,5-α]pyridin-6-yl)-5-(3,4,5-trimethoxyphenyl)-Δ2,3-oxazoline

EXAMPLE 49A ethyl 6-hydroxymethylnicotinate

A slurry of dry calcium chloride (22.7 g, 0.205 mol) in ethanol (300 mL) and THF (300 mL) at 0° C. was treated portionwise with sodium borohydride (15.5 g, 0.41 mol), stirred for 2.5 hours, treated with dimethyl 2,5-pyridinedicarboxylate (20.0 g, 0.103 mol), stirred for 20 minutes, treated with saturated ammonium chloride solution (100 mL), and concentrated. The concentrate was dissolved in dichloromethane, and the solution was washed sequentially with saturated ammonium chloride solution, water, and brine, dried (MgSO$_4$), filtered, and concentrated to provide the desired product containing approximately 10% methyl 6-hydroxymethylnicotinate. This mixture was used directly in the next step without further purification.

MS (ESI(+)) m/z 182 (M+H)$^+$;

$^1$H NMR (CDCl$_3$) δ 8.99 (m, 1H), 8.30 (dd, J=3.0, 9.0 Hz, 1H), 7.62 (d, J=9.0 Hz, 1H), 5.60 (t, J=3.0 Hz, 1H), 4.73 (d, J=3.0 Hz, 2H), 4.35 (q, J=7.0 Hz, 2H), 1.35 (t, J=7.0 Hz, 3H).

EXAMPLE 49B ethyl 6-formylnicotinate

A solution/slurry of Example 49 (5.00 g, 27.9 mmol) and manganese dioxide (24.3 g, 279 mmol) in dioxane (100 mL) was heated at 90° C. for 30 minutes and filtered while hot. The filtrate was concentrated to provide 2.95 g (60%) of the desired product, which was used in the next step without further purification.

MS (DCI/NH$_3$) m/z 180 (M+H)$^+$ and 197 (M+NH$_4$)$^+$;

$^1$H NMR (DMSO-d$_6$) δ 10.05 (s, 1H), 9.27 (d, J=3.0 Hz, 1H), 8.50 (dd, J=3.0, 9.0 Hz, 1H), 8.05 (d, J=9.0 Hz, 1H), 4.4 (q, J=7.0 Hz, 2H), 1.45 (t, J=7.0 Hz, 3H).

EXAMPLE 49C ethyl 6-formylnicotinate oxime

A mixture of sodium acetate (8.68 g, 106 mmol), and hydroxyamine hydrochloride (7.35 g, 106 mmol) in methanol (70 mL) was stirred at room temperature for 30 minutes. The precipitate which formed was removed by filtration, and the filtrate was poured into a solution of Example 49B (6.33 g, 35.3 mmol) in methanol (20 mL), stirred at room temperature for 18 hours, and concentrated. The concentrate was dissolved in 3:1 dichloromethane/isopropanol, and this solution was washed sequentially with 1M K$_2$CO$_3$ and water, dried (MgSO$_4$), filtered, and concentrated to provide 6.38 g (93%) of the desired product.

EXAMPLE 49D ethyl 6-aminomethylnicotinate

A solution of Example 49C (3.40 g, 17.5 mmol) in water (40 mL) and acetic acid (53 mL) at 0° C. was treated slowly with zinc dust (5.72 g, 87.5 mmol), stirred for 20 minutes, filtered, and concentrated. The concentrate was dissolved in 3:1 dichloromethane/isopropanol, and this solution was washed sequentially with 1M Na$_2$CO$_3$ and water, dried (MgSO$_4$), filtered, and concentrated to provide 3.68 g (66%) of the desired product.

MS (DCI/NH$_3$) m/z 181 (M+H)$^+$;

$^1$H NMR (DMSO-d$_6$) δ 9.04 (d, J=3.0 Hz, 1H), 8.43 (dd, J=3.0, 9.0 Hz, 1H), 7.69 (d, J=9.0 Hz, 1H), 4.36 (q, J=7.0 Hz, 2H), 1.85 (s, 2H), 1.35 (t, J=7.0 Hz, 2H), 1.02 (d, J=3.0 Hz, 1H).

EXAMPLE 49E ethyl 6-(formylamino)methylnicotinate

A solution of Example 49D (6.49 g, 36.0 mmol) in formic acid (75 mL) was refluxed for 18 hours and concentrated. The concentrate was dissolved in dichloromethane, and this solution was washed sequentially with 10% NaHCO$_3$ and water, dried (MgSO$_4$), filtered, and concentrated. The concentrate was purified by a flash column chromatography on silica gel with 96:4 dichloromethane/methanol to provide 2.83 g (38%) of the desired product.

MS (DCI/NH$_3$) m/z 209 (M+H)$^+$;

$^1$H NMR (CDCl$_3$) δ 9.14 (d, J=3.0 Hz, 1H), 8.35 (s, 1H), 8.28 (dd, J=3.0, 9.0 Hz, 1H), 7.35 (d, J=9.0 Hz, 1H), 4.67 (d, J=6.0 Hz, 2H), 4.42 (q, J=7.0 Hz, 3H), 1.41 (t, J=7.0 Hz, 3H).

EXAMPLE 49F methyl imidazo[1,5-α]pyridine-6-carboxylate

A solution of Example 49E (2.83 g, 13.6 mmol) in dichloromethane (30 mL) was treated with POCl$_3$ (2.8 mL, 30.0 mmol), stirred at 60° C. for 3 hours, and concentrated. The concentrate was treated with 1M Na$_2$CO$_3$ and extracted with dichloromethane. The extract was washed with water, dried (MgSO$_4$), filtered, and concentrated. The concentrate was purified by flash column chromatography with 98:2 dichloromethane/methanol to provide 2.64 g (93%) of the desired product.

MS (DCI/NH$_3$) mz 191 (M+H)$^+$;

$^1$H NMR (CDCl$_3$) δ 8.73 (s, 1H), 8.21 (s, 1H), 7.46 (s, 1H), 7.45 (d, J=9.0 Hz, 1H), 7.24 (dd, J=3.0 Hz, 9.0 Hz, 1H), 4.40 (q, J=7.0 Hz, 2H), 1.41 (t, J=7.0 Hz, 3H).

EXAMPLE 49G imidazo[1,5-α]pyridine-6-carboxylic acid

A solution of Example 49F (2.60 g, 13.7 mmol) in 1M LiOH (41 mL) and THF (50 mL) was stirred at room temperature for 1 hour, treated with 1M HCl (42 mL), and extracted with dichloromethane. The extract was washed with water, dried (MgSO$_4$), filtered, and concentrated to provide 1.92 g (86%) of the desired compound, which was used in the next step without further purification.

MS (DCI/NH$_3$) m/z 163 (M+H)$^+$;

$^1$H NMR (DMSO-d$_6$) δ 13.28 (br s, 1H), 9.08 (s, 1H), 8.65 (br s, 1H), 7.57 (d, J=9.0 Hz, 1H), 7.42 (br s, 1H), 7.12 (dd, J=2.0, 9.0 Hz, 1H).

EXAMPLE 49H 2-(imidazo [1,5-α]pyridin-6-yl)-5-(3,4,5-trimethoxyphenyl)-Δ2,3-oxazoline Example 49G (1.92 g, 11.9 mmol) was processed as described in Example 4 to provide 337 mg (8%) of the desired product.

MS (ESI(+)) m/z 354 (M+H)$^+$;

$^1$H NMR (CDCl$_3$) δ 8.58 (s, 1H), 8.15 (s, 1H), 7.48 (d, J=9.0 Hz, 2H), 7.31 (dd, J=3.0, 9.0 Hz, 1H), 6.56 (s, 2H), 5.58 (dd, J=9.0, 12.0 Hz, 1H), 4.46 (dd, J=12.0, 15.0 Hz, 1H), 4.02 (dd, J=9.0, 15.0 Hz, 1H), 3.85 (s, 6H), 3.83 (s, 3H).

EXAMPLE 50

2-(2-methyl-6-indolizinyl)-5-(3,4,5-trimethoxyphenyl)-Δ2,3-oxazoline

EXAMPLE 50A

N-(2-oxo-1-propyl)-2-methyl-5-methoxycarbonylpyridinium bromide

A solution of methyl 6-methylnicotinate (1.00 g, 6.60 mmol) and bromoacetone (1.00 g, 7.30 mmol) in acetone (3 mL) was refluxed overnight, cooled to room temperature, and decanted. The resulting solid was dried under vacuum to provide approximately1.47 g the desired product as a solid, which was used directly in the next step without further purification.

EXAMPLE 50B methyl 2-methyl-indolizine-6-carboxylate

A mixture of Example 50A (570 mg, 2.32 mmol) and sodium carbonate (400 mg, 5.0 mmol) in ethanol (10 mL) was refluxed for 3 hours and concentrated. The concentrate was dissolved in dichloromethane, and this solution was washed with water, dried (MgSO$_4$), filtered, and concentrated. The concentrate was purified by flash column chromatography on silica gel with 2:1 hexanes/dichloromethane to provide 407 mg (93%) of the desired product.

MS (DCI/NH$_3$) m/z 190 (M+H)$^+$;

$^1$H NMR (DMSO-d$_6$) δ 8.98 (s, 1H), 7.54 (s, 1H), 7.33 (d, J=9.0 Hz, 1H), 7.11 (d, J=9.0 Hz, 1H), 6.32 (s, 1H), 3.82 (s, 3H), 2.24 (s, 3H).

EXAMPLE 50C 2-methyl-indolizine-6-carboxylic acid

A solution of Examplr 50A (200 mg, 1.06 mmol) in 6M HCl (20 mL) was refluxed for 3 hours and was concentrated to provide 200 mg of the desired product.

MS (DCI/NH$_3$) m/z 176 (M+H)$^+$;

$^1$H NMR (DMSO-d$_6$) δ 8.91 (s, 1H), 7.52 (s, 1H), 7.31 (d, J=12.0 Hz, 1H), 7.10 (dd, J=3.0, 9.0 Hz, 1H), 6.31 (s, 1H), 2.25 (s, 3H).

EXAMPLE 50D 2-(2-methyl-6-indolizinyl)-5-(3,4,5-trimethoxyphenyl)-Δ2,3-oxazoline Example 50C (210 mg, 0.99 mmol) was processed as described in Example 4 to provide 75.2 mg (21%) of the desired product.

MS (ESI(+)) m/z 367 (M+H)$^+$;

$^1$H NMR (CDCl$_3$) δ 8.57 (br s, 1H), 7.13–7.30 (m, 3H), 6.58 (s, 2H), 6.30 (s, 1H), 5.56 (br s, 1H), 4.45 (br s, 1H), 4.00 (br s, 1H), 3.86 (s, 3H), 3.84 (s, 6H), 2.32 (s, 3H).

EXAMPLE 51

2-(3-fluoro-4-methoxyphenyl)-5-(3 4,5-trimethoxyphenyl)-Δ2,3-oxazoline

EXAMPLE 51A

3-Fluoro-4-methoxybenzoic acid (1.00 g, 5.88 mmol) was processed as described in Example 4 to provide 1.37 g of the desired product.

MS (ESI(+)) m/z 380 (M+H)$^+$;

$^1$H NMR (CDCl$_3$) δ 7.56–7.51 (m, 2H), 6.98 (app t, J=8.1 Hz, 1H), 6.63 (s, 2H), 6.47 (m, 1H), 4.92–4.88 (m, 1H), 3.94 (s, 3H), 3.95–3.85 (m, 1H), 3.85 (s, 6H), 3.84 (s, 3H), 3.53-3.49 (m, 1H).

EXAMPLE 51B 2-(3-fluoro-4-methoxyphenyl)-5-(3,4,5-trimethoxyphenyl)-Δ2,3-oxazoline Example 51A (530 mg, 1.4 mmol) was processed as described in Example 4 to provide 415 mg of the desired product.

MS (ESI(+)) m/z 362 (M+H)$^+$;

$^1$H NMR (CDCl$_3$) δ 7.92 (m, 1H), 7.80–7.76 (m, 1H), 7.06–7.03 (m, 1H), 6.56 (s, 2H), 5.65 (m, 1H), 4.50 (m, 1H), 4.05 (m, 1H), 3.96 (s, 3H), 3.86 (s, 3H), 3.86 (s, 6H);

Anal. calcd for C$_{19}$H$_{20}$FNO$_5$: C, 63.15; H, 5.58; N, 3.88. Found: C, 63.22; H, 5.68; N, 3.82.

EXAMPLE 52

2-((2S)-indolin-2-yl)-5-(3,4,5-trimethoxyphenyl)-Δ2,3-oxazoline

EXAMPLE 52A 1-(tert-butoxycarbonyl)-1H-indole-2-carboxylic acid (S)-(–)-Indoline-2-carboxylic acid (1.88 g, 11.5 mmol) was processed as described in Example 4 to provide 2.89 g of the desired product.

MS (ESI(+)) m/z 281 (M+NH$_4$)$^+$;
$^1$H NMR (CDCl$_3$) δ 12.88 (br s, 1H), 8.72 (m, 1H), 7.19–7.14 (m, 2H), 6.96–6.90 (m, 1H), 4.76 (dd, J=4.1, 11.5 Hz, 1H), 3.52 (dd, J=11.5, 17.0 Hz, 1H), 3.05–2.98 (m, 1H), 2.50 (s, 9H).

EXAMPLE 52B tert-butyl 2-(((2-hydroxy-2-(3,4,5-trimethoxyphenyl)ethyl)amino)carbonyl)-1H-indole-1-carboxylate Example 52A (1.02 g, 3.88 mmol) was processed as described in Example 4 to provide 1.08 g of the desired product as a 1:1 mixture of diastereomers. MS (ESI(+)) m/z 473 (M+H)$^+$;
$^1$H NMR (CDCl$_3$) δ 7.65 (br s, 1H), 7.23–7.15 (m, 2H), 7.03–6.98 (m, 1H), 6.57 (m, 1H), 4.90–4.84 (m, 1H), 4.79–4.78 (m, 1H), 3.83 (s, 3H), 3.82 (s, 6H), 3.70–3.65 (m, 1H), 3.51–3.47 (m, 1H), 3.33–3.30 (m, 2H), 1.56 (s, 9H).

EXAMPLE 52C tert-butyl 2-(5-(3,4,5-trimethoxyphenyl)-4,5-dihydro-1,3-oxazol-2-yl)-1H-indole-1-carboxylate A solution of Example 52C (146 mg, 0.31 mmol) in chloroform (3 mL) and pyridine (0.125 mL) at 0° C. was treated with thionyl chloride (70 mL, 0.93 mmol), stirred for 20 minutes, treated with dichloromethane, washed with 10% NaHCO$_3$, dried (MgSO$_4$), filtered, and concentrated. The concentrate was purified on silica gel with 30:70 ethyl acetate/hexanes to provide 99 mg of the desired product as a mixture of diastereomers.
$^1$H NMR (CDCl$_3$) δ 7.61 (m, 1H), 7.22–7.14 (m, 2H), 7.02–6.97 (m, 1H), 6.57 (m, 2H), 4.95 (m, 1H), 4.91–4.86 (m, 1H), 3.97–3.86 (m, 1H), 3.84–3.82 (m, 9H), 3.60–3.42 (m, 3H), 1.55 (m, 9H);
HRMS (FAB): Calc. (M+H)$^+$ for C$_{25}$H$_{31}$N$_2$O$_6$: 455.2182. Found: 455.2166.

EXAMPLE 52D 2-((2S)-indolin-2-yl)-5-(3,4,5-trimethoxyphenyl)-Δ2,3-oxazoline 2-((2S)-1-Tert-butyloxycarbonylindolin-2-yl)-5-(3,4,5-trimethoxyphenyl)-Δ2,3-oxazoline (86 mg, 0.19 mmol) was treated with 4M HCl in dioxane (2 mL), stirred for three hours, and concentrated. The concentrate was dissolved in dichloromethane and extracted with saturated NaHCO$_3$. The extract was separated, and the aqueous layer was extracted with dichloromethane. The combined extracts were dried (MgSO$_4$), filtered, and concentrated. The concentrate was chromatographed on silica gel with a gradient of from 30 to 50% ethyl acetate/hexanes to provide 44 mg of the desired product as a mixture of diastereomers.
MS (ESI(+)) m/z 355 (M+H)$^+$;
$^1$H NMR (CDCl$_3$) δ 7.53–7.43 (m, 1H), 7.11–7.06 (m, 2H), 6.86–6.80 (m, 1H), 6.74 (m, 1H), 6.60 (m, 2H), 4.95 (m, 1H), 4.47–4.39 (m, 1H), 4.01–3.86 (m, 1H), 3.85–3.81 (m, 9H), 3.68–3.52 (m, 2H), 3.10$^{-2.97}$ (m, 1H).

EXAMPLE 53

2-(2-chloro-4-nitrophenyl)-5-(3,4,5-trimethoxyphenyl)-Δ2,3-oxazoline

EXAMPLE 53A 2-chloro-N-(2-hydroxy-2-(3,4,5-trimethoxyphenyl)ethyl)-4-nitrobenzamide 2-Chloro-4-nitrobenzoic acid (765 mg, 3.79 mmol) was processed as described in Example 4 to provide 735 mg of the desired product.

MS (ESI(+)) m/z 428 (M+NH$_4$)$^+$;
$^1$H NMR (CDCl$_3$) δ 8.30 (d, J=2.4 Hz, 1H), 8.17 (dd, J=2.4, 8.5 Hz, 1H), 7.80 (d, J=8.5 Hz, 1H), 6.64 (s, 2H), 4.95–4.91 (m, 1H), 4.02–3.94 (m, 1H), 3.87 (s, 6H), 3.84 (s, 3H), 3.56–3.47 (m, 1H), 2.70 (d, J=3.1 Hz, 1H).

EXAMPLE 53B 2-(2-chloro-4-nitrophenyl)-5-(3,4,5-trimethoxyphenyl)-Δ2,3-oxazoline Example 53A (706 mg, 1.72 mmol) was processed as described in Example 4 to provide 570 mg of the desired product.

MS (ESI(+)) m/z 393 (M+H)$^+$;
$^1$H NMR (CDCl$_3$) δ 8.37 (d, J=2.4 Hz, 1H), 8.18 (dd, J=2.4, 8.8 Hz, 1H), 8.05 (d, J=8.5 Hz, 1H), 6.60 (s, 2H), 5.65 (dd, J=8.5, 10.5 Hz, 1H), 4.57 (dd, J=10.2, 15.3 Hz, 1H), 4.13 (dd, J=8.5, 15.6 Hz, 1H), 3.87 (s, 6H), 3.86 (s, 3H).

EXAMPLE 54

2-(2-fluoro-4-nitrophenyl)-5-(3,4,5-trimethoxyphenyl)-Δ2,3-oxazoline

EXAMPLE 54A 2-fluoro-N-(2-hydroxy-2-(3 4.5-trimethoxyphenyl)ethyl)-4-nitrobenzamide 2-Fluoro-4-nitrobenzoic acid (702 mg, 3.79 mmol), was processed as described in Example 4 to provide 767 mg (51%) of the desired product.

MS (ESI(+)) m/z 412 (M+NH$_4$)$^+$;
$^1$H NMR (CDCl$_3$) δ 8.30 (dd, J=7.8, 8.5 Hz, 1H), 8.14 (dd, J=2.4, 8.8 Hz, 1H), 8.04 (dd, J=2.4, 11.2 Hz, 1H), 7.2–7.1 (m, 1H), 6.65 (s, 2H), 4.94–4.91 (m, 1H), 3.95 (m, 1H), 3.87 (s, 6H), 3.85 (s, 3H), 3.60–3.55 (m, 1H), 2.69 (d, J=3.1 Hz, 1H).

EXAMPLE 54B 2-(2-fluoro-4-nitrophenyl)-5-(3,4,5-trimethoxyphenyl)-Δ2,3-oxazoline Example 54A (760 mg, 1.93 mmol) was processed as described in Example 4 to provide 640 mg (88%) of the desired product.

MS (ESI(+)) m/z 377 (M+H)$^+$;
$^1$H NMR (CDCl$_3$) δ 8.18–8.05 (m, 3H), 6.58 (s, 2H), 5.64 (dd, J=8.1, 9.9 Hz, 1H), 4.57 (dd, J=10.3, 15.5 Hz, 1H), 4.13 (dd, J=8.5, 15.8 Hz, 1H), 3.87 (s, 6H), 3.86 (s, 3H).

EXAMPLE 55

2-(1.4-dimethylindol-5-yl)-5-(3,4,5-trimethoxyphenyl)-Δ2,3-oxazoline

A solution of Example 6 (187 mg, 0.51 mmol) in THF (5 mL) at 0° C. was treated dropwise with 2.5 M n-butyllithium in hexane (0.22 mL, 0.56 mmol), stirred for 15 minutes, treated with methyl iodide (70 mL, 1.02 mmol), stirred for 18 hours while warming to room temperature, poured into water, and extracted with dichloromethane (2x). The combined extracts were dried (MgSO$_4$), filtered, and concentrated. The concentrate was purified on silica gel with a gradient of from 30% to 60% ethyl acetate/hexanes to provide 15 mg of the desired product.

$^1$H NMR (CDCl$_3$) δ 7.81 (d, J=8.5 Hz, 1H), 7.20 (d, J=8.5 Hz, 2H), 7.10 (d, J=3.3 Hz, 1H), 6.63 (d, J=2.9 Hz, 1H), 6.62

(s, 2H), 5.56 (dd, J=8.1, 10.3 Hz, 1H), 4.52 (dd, J=10.3, 14.7 Hz, 1H), 4.04 (dd, J=8.1, 14.7 Hz, 1H), 3.86 (s, 9H), 3.81 (s, 3H), 2.88 (s, 3H); HRMS (FAB) Calc.(M+H)$^+$ for $C_{22}H_{25}N_2O_4$: 381.1830. Found, 381.1830.

EXAMPLE 56

2-(1-methlthiothiocarbonylindol-5-yl)-5-(3,4,5-trimethoxyphenyl)-Δ2,3-oxazoline

A solution of Example 11 (179 mg, 0.51 mmol) in THF (4 mL) at 0° C. was treated with sodium hydride (15 mg, 0.61 mmol), stirred for ten minutes, treated with carbon disulfide (61 mL, 1.02 mmol), stirred for 18 hours while warming to room temperature, cooled to 0° C., treated with methyl iodide (0.1 mL, 1.53 mmol, stirred for thirty minutes at room temperature, poured into water, and extracted with ethyl acetate The extract was dried (MgSO$_4$), filtered, and concentrated. The concentrate was purified on silica gel with a gradient of from 40% to 50% ethyl acetate/hexanes to provide 200 mg of the desired product.

MS (ESI(+)) m/z 443 (M+H)$^+$;

$^1$H NMR (CDCl$_3$) δ 9.00 (d, J=8.8 Hz, 1H), 8.24 (d, J=1.4 Hz, 1H), 8.16 (d, J=3.7 Hz, 1H), 8.03 (dd, J=1.7, 8.8 Hz, 1H), 6.73 (dd, J=0.7, 3. Hz, 1H), 6.59 (s, 2H), 5.62 (dd, J=8.1, 10.2 Hz, 1H), 4.49 (dd, J=9.8, 14.6 Hz, 1H), 4.03 (dd, J=8.1, 14.6 Hz, 1H), 3.85 (s, 9H), 2.82 (s, 3H);

Anal. calcd for $C_{22}H_{22}N_2O_4S_2$: C, 59.71; H, 5.01; N, 6.33. Found: C, 59.58; H, 5.11; N, 6.15.

EXAMPLE 57

2-(1,3-dimethylindol-5-yl)-5-(3,4,5-trimethoxyphenyl)-Δ2,3-oxazoline

EXAMPLE 57A

N-(2-hydroxy-2-(3,4,5-trimethoxyphenyl)ethyl)-1,2-dimethyl-1H-indole-5-carboxamide 1,3-Dimethylindole-5-carboxylic acid (400 mg, 2.12 mmol) was processed as described in Example 4 to provide the desired product, which was used in the next step without further purification.

MS (ESI(+)) m/z 399 (M+H)$^+$;

EXAMPLE 57B 2-(1.3-dimethylindol-5-yl)-5-(3,4,5-trimethoxyphenyl)-Δ2,3-oxazoline Example 57A was processed as described in Example 4 to provide 490 mg of the desired product.

MS (ESI(+)) m/z 381 (M+H)$^+$;

$^1$H NMR (CDCl$_3$) δ 8.27 (d, J=1.5 Hz, 1H), 7.92 (dd, J=1.5, 8.5 Hz, 1H), 7.31 (d, J=8.8 Hz, 1H), 6.87 (d, J=0.7 Hz, 1H), 6.62 (s, 2H), 5.60 (dd, J=8.1, 10.3 Hz, 1H), 4.49 (dd, J=9.9, 14.3 Hz, 1H), 4.02 (dd, J=7.7, 14.3 Hz, 1H), 3.85 (s, 9H), 3.76 (s, 3H), 2.33 (d, J=0.7 Hz, 1H);

Anal. calcd for $C_{22}H_{24}N_2O_4$: C, 69.46; H, 6.36; N, 7.36. Found: C, 69.21; H, 6.27; N, 6.96.

EXAMPLE 58

2-(6-chloroindol-5-yl)-5-(3,4,5-trimethoxyphenyl)-Δ2,3-oxazoline

EXAMPLE 58A methyl 4-amino-2-chloro-5-iodo-benzoate

A solution of methyl 4-amino-2-chloro-benzoate (1.14 g, 6.16 mmol) in dichloromethane (30 mL) and methanol (15 mL) was treated sequentially with calcium carbonate (1.85 g, 18.5 mmol) and benzyl trimethylammonium dichloroiodate (3.22 g, 9.24 mmol), stirred for 18 hours, treated with additional benzyl trimethylammonium dichloroiodate (2 g, 5.75 mmol), stirred for 3 days, filtered into a separatory funnel, washed with saturated NaHSO$_3$, dried (MgSO$_4$), filtered, and concentrated. The concentrate was recrystallized from ethyl acetate to provide the majority of the desired product. The filtrate was concentrated, and the concentrate was purified on silica gel with a gradient of from 10% to 20% ethyl acetate/hexanes to provide a total of 1.3 g of the desired product.

MS (ESI(−)) m/z 310 (M−H)$^-$;

$^1$H NMR (CDCl$_3$) d 8.25 (d, J=2.0 Hz, 1H), 6.75 (d, J=2.0 Hz, 1H), 4.52 (br s, 2H), 3.87 (s, 3H). Characterization for the minor product: $^1$H NMR (300 MHz, CDCl$_3$) 7.72 (d, J=8.8 Hz 1H), 6.63 (d, J=8.5 Hz, 1H), 4.71 (br s, 2H), 3.88 (s, 3H).

EXAMPLE 58B methyl 6-chloro-5-indolecarboxylate

A 50% solution of ethyl ethynyl ether in hexanes (2.1 mL, 10.8 mmol) at 0° C. was slowly treated with 1M catechol borane in THF (9.7 mL, 9.7 mmol), warmed to room temperature, stirred for 2 hours, heated at 70° C. for 2 hours, cooled to room temperature, treated sequentially with Example 58A (1.77 g, 5.69 mmol) in THF (30 mL), tetrakis (triphenylphosphine)-palladium(0) (329 mg, 0.28 mmol), and powdered sodium hydroxide (683 mg, 17.1 mmol), heated to reflux, stirred for 18 hours, cooled to room temperature, treated with 2M HCl (30 mL), stirred for 18 hours, treated with ethyl acetate, washed sequentially with water, 2M Na$_2$CO$_3$, and brine, dried (MgSO$_4$), filtered, and concentrated. The concentrate was purified by flash column chromatography on silica gel to provide the impure desired product which was used in the next step without further purification.

EXAMPLE 58C 6-chloro-5-indolecarboxylic acid

A solution of Example 58B (1.17 g, approximately 5.6 mmol) in THF (50 mL) was treated with 1M LiOH (56 mL, 56 mmol), heated at 50° C., stirred for 18 hours, treated with 1M NaOH, washed with diethyl ether, acidified with HCl, and extracted with ethyl acetate. The extract was dried (MgSO$_4$), filtered, and concentrated. The concentrate was purified on silica gel with 50% ethyl acetate/hexanes to provide of 660 mg of the desired product.

$^1$H NMR (DMSO-d$_6$) δ 12.73 (br s, 1H), 11.45 (s, 1H), 8.13 (s, 1H), 7.49 (m, 2H), 6.57 (m, 1H).

EXAMPLE 58D 6-chloro-N-(2-hydroxy-2-(3,4,5-trimethoxyphenyl) ethyl)-1H-indole-5-carboxamide Example 58C (660 mg, 3.38 mmol) was processed as described in Example 4A to provide 128 mg of the desired product.

MS (ESI(+)) m/z 405 (M+H)$^+$;

$^1$H NMR (CDCl$_3$) δ 8.29 (br s, 1H), 8.00 (s, 1H), 7.44 (s, 1H), 7.28 (m, 1H), 6.68 (s, 2H), 6.66 (m, 1H), 6.59 (m, 1H), 4.99 (m, 1H), 4.00–3.92 (m, 1H), 3.88 (s, 6H), 3.85 (s, 3H), 3.63–3.55 (m, 1H), 3.45 (d, J=3.7 Hz, 1H).

EXAMPLE 58E 2-(6-chloroindol-5-yl)-5-(3,4,5-trimethoxyphenyl)-Δ2,3-oxazoline

Example 58D (63 mg, 0.156 mmol) was processed as described in Example 4B to provide 36 mg of the desired product.

$^1$H NMR (CDCl$_3$) δ 9.09 (br s, 1H), 8.11 (s, 1H), 7.38 (s, 1H), 7.16 (m, 1H), 6.59 (s, 2H), 6.45 (m, 1H), 5.66 (dd, J=8.1, 9.8 Hz, 1H), 4.51 (dd, J=10.5, 14.2 Hz, 1H), 4.07 (dd, J=8.5, 14.6 Hz, 1H), 3.80 (s, 6H), 3.79 (s, 3H);

HRMS (FAB) Calc. (M+H) for C$_{20}$H$_{20}$ClN$_2$O$_4$: 387.1112. Found: 387.1110.

EXAMPLE 59

2-(1-methyloxindol-5-yl)-5-(3,4,5-trimethoxyphenyl)-Δ2,3-oxazoline

EXAMPLE 59A benzyl 1-methyl-oxindole-5-carboxylate

A solution of 5-bromo-1-methyl oxindole (3.75 g, 16.6 mmol) and triethylamine (3.48 mL) in THF (40 mL) was treated with benzyl alcohol (2.58 mL) and PdCl$_2$(dppf) (300 mg), stirred under carbon monoxide (680 psi) at 130° C. for 16 hours, depressurized, filtered through diatomaceous earth (Celite®), and concentrated. The concentrate was purified on silica gel with 30% ethyl acetate/hexanes to provide 2.36 g of the desired product.

MS (ESI(+)) m/z 299 (M+NH$_4$)$^+$;

$^1$H NMR (CDCl$_3$) δ 8.10$^{-8.07}$ (m, 1H), 7.95 (s, 1H), 7.47–7.33 (m, 5H), 6.86 (d, J=8.1 Hz, 2H), 5.35 (s, 2H), 3.56 (s, 2H), 3.25 (s, 3H).

EXAMPLE 59B 1-methyl-oxindole-5-carboxylic acid

A solution of Example 59A (1.2 g, 4.27 mmol) in ethyl acetate (30 mL) and methanol (20 mL) was treated with 10% Pd/C (200 mg), stirred under hydrogen (balloon) for 18 hours, filtered through diatomaceous earth (Celite®) with 9:1 dichloromethane/methanol solution rinses, and concentrated to provide 460 mg of the desired product.

$^1$H NMR (DMSO-d$_6$) δ 7.92 (dd, J=1.1, 8.1 Hz, 1H), 7.80 (d, J=0.7 Hz, 1H), 7.07 (d, J=8.1 Hz, 1H), 3.62 (s, 2H), 3.15 (s, 3H).

EXAMPLE 59C

N-(2-hydroxy-2-(3,4,5-trimethoxyphenyl)ethyl)-1-methyl-2-oxo-5-indolinecarboxamide Example 59B (430 mg, 2.25 mmol) was processed as described in Example 4A to provide 340 mg of the desired product.

MS (ESI(+)) m/z 401 (M+H)$^+$;

$^1$H NMR (DMSO-d$_6$) δ 8.38 (app t, J=5.5 Hz, 1H), 7.83 (d, J=8. Hz, 1H), 7.77 (s, 1H), 7.05 (d, J=8.1 Hz, 1H), 6.65 (s, 2H), 5.52 (d, J=4.4 Hz, 1H), 4.74–4.68 (m, 1H), 3.74 (s, 6H), 3.63 (s, 3H), 3.61 (s, 2H), 3.48–3.37 (m, 1H), 3.15 (s, 3H).

EXAMPLE 59D 2-(1-methyloxindol-5-yl)-5-(3,4,5-trimethoxyphenyl)-Δ2,3-oxazoline Example 59C (110 mg, 0.275 mmol) was processed as described in Example 4B to provide 50 mg of the desired product.

$^1$H NMR (CDCl$_3$) δ 8.00 (m, 1H), 7.91 (s, 1H), 6.87 (d, J=8.0 Hz, 1H), 6.57 (s, 2H), 5.57 (dd, J=8.1, 9.7 Hz, 1H), 4.45 (dd, J=10.2, 14.8 Hz, 1H), 4.00 (dd, J=8.5, 14.8 Hz, 1H), 3.85 (s, 9H), 3.56 (s, 2H), 3.25 (s, 3H);

HRMS (FAB) Calc. (M+H)$^+$ for C$_2$ H$_{23}$N$_2$O$_5$: 383.1607; Found: 383.1607.

Anal. calcd for C$_{21}$H$_{23}$N$_2$O$_5$: C, 65.96; H, 5.80; N, 7.33. Found: C, 65.71; H, 5.85; N, 7.15.

EXAMPLE 60

2-(6-Chloro-1-methylindol-5-yl)-5-(3,4,5-trimethoxyphenyl)-Δ2,3-oxazoline

A solution of Example 58 (70 mg, 0.18 mmol) in THF (5 mL) at 0° C. was treated with sodium hydride (9 mg, 0.36 mmol), stirred for ten minutes, treated with methyl iodide (34 mL, 0.54 mmol), stirred for 1 hour at 0° C. and for 1.5 hours at room temperature, treated with additional sodium hydride (9 mg, 0.36 mmol) and methyl iodide (0.1 mL), stirred for 18 hours at room temperature, poured into water, and extracted with ethyl acetate. The extract was dried (MgSO$_4$), filtered, and concentrated. The concentrate was purified on silica gel with 1:1 ethyl acetate/hexanes to provide 55 mg of the desired product.

$^1$H NMR (CDCl$_3$) δ 8.15 (s, 1H), 7.43 (s, 1H), 7.10 (d, J=3.1 Hz, 1H), 6.66 (s, 2H), 6.51 (dd, J=0.7, 3.1 Hz, 1H), 5.60 (dd, J=8.1, 9.8 Hz, 1H), 4.55 (dd, J=10.2, 14.9 Hz, 1H), 4.08 (dd, J=8.1, 14.6 Hz, 1H), 3.87 (s, 6H), 3.85 (s, 3H), 3.79 (s, 3H);

HRMS (FAB) Calc. (M+H) for C$_{21}$H$_{22}$ClN$_2$O$_4$): 401.1268; Found: 401.1256;

Anal. calcd for C$_{21}$H$_{21}$CN$_2$O$_4$ 0.5 H$_2$O: C, 61.54; H, 5.41; N, 6.83. Found: C, 61.29; H, 5.47; N, 6.72.

EXAMPLE 61

2-(1-difluoromethylindol-5-yl)-5-(3,4,5-trimethoxyphenyl)-Δ2,3-oxazoline

A solution of Example 11 (427 mg, 1.21 mmol) in THF (5 mL) at 0° C. was treated with sodium hydride (35 mg, 1.46 mmol), stirred for 15 minutes, cooled to −78° C., treated with excess difluorochloromethane, stirred for 18 hours warming slowly to room temperature, poured into 5.5M NH$_4$Cl and extracted with ethyl acetate. The extract was dried (MgSO$_4$), filtered, and concentrated. The concentrate was purified on silica gel with s gradient of from 50% to 60% ethyl acetate/hexanes to provide 16.9 mg of the desired product.

$^1$H NMR (CDCl$_3$) δ 8.37 (s, 1H), 8.03 (m, 1H), 7.56 (d, J=8.5 Hz, 1H), 7.29 (d, J=3.7 Hz, 1H), 7.22 (t, J=60.7 Hz, 1H), 6.66 (d, J=3.4 Hz, 1H), 6.53 (s, 2H), 5.65 (dd, J=8.8, 9.5 Hz, 1H), 4.47 (dd, J=10.2, 14.2 Hz, 1H), 4.03 (dd, J=8.5, 14.2 Hz, 1H), 3.78 (s, 9H).

EXAMPLE 62

2-(3-chloro-1-methylindol-5-yl)-5-(3,4,5-trimethoxyphenyl)-Δ2,3-oxazoline

EXAMPLE 62A methyl 3-chloro-5-indolecarboxylate

A solution of methyl 5-indolecarboxylate (501.1 mg, 2.65 mmol) in methanol (15 mL) was treated with N-chlorosuccinimide (425.4 mg, 3.18 mmol), stirred for 18 hours, and concentrated. The concentrate was dissolved into ethyl acetate, and this solution was washed with 1M NaHCO$_3$ (2×), dried (MgSO$_4$), filtered, and concentrated. The concentrate was purified on silica gel with 15% ethyl acetate/hexanes to provide 368.8 mg of the desired product.

MS (ESI(+)) m/z 224 (M+H)$^+$;

$^1$H NMR (CDCl$_3$) δ 8.39 (s, 1H), 7.97 (dd, J=1.4, 10.2 Hz, 1H), 7.32 (dd, J=0.7, 9.5 Hz, 1H), 7.1 (s, 1H), 3.95 (s, 3H), 3.79 (s, 3H).

EXAMPLE 62B 3-chloro-5-indolecarboxylic acid

A solution of Example 62A (361 mg, 1.62 mmol) in THF (7 mL) and 1M LiOH (3.3 mL) was heated at 50° C. for 5 hours, treated with ethyl acetate and extracted with 10% NaHCO$_3$ (3×). The extract was treated with 6M HCl and extracted with ethyl acetate (2×40 mL). The organic layer was dried (MgSO$_4$), filtered, and concentrated to provide 253.2 mg of the desired compound.

MS (ESI(+)) m/z 211 (M+H)$^+$;

$^1$H NMR (CDCl$_3$) δ 12,71 (s, 1H), 8.14 (s, 1H), 7.84 (dd, J=2.2, 8.8 Hz, 1H), 7.69 (s, 1H) 7.6 (dd, J=2.2, 11.0 Hz, 1H), 3.83 (s, 3H), 3.35 (s, 3H).

EXAMPLE 62C 3-chloro-N-(2-hydroxy-2-(3,4,5-trimethoxyphenyl) ethyl)-1-methyl-1H-indole-5-carboxamide 3-Chloro-5-indolecarboxylic acid (182.3 mg, 0.870 mmol) was processed as described in Example 4A to provide 226.7 mg of the desired product.

MS (ESI(+)) m/z 419 (M+H)$^+$;

$_1$H NMR (CDCl$_3$) δ 8.01 (d, J=1.35 Hz, 1H), 7.76 (dd, J=1.7, 10.5 Hz, 1H), 7.31(d, J=8.5 Hz, 1H), 7.11 (s, 1H), 6.66 (s, 2H), 4.97–4.94 (m, 1H), 3.89 (s, 3H), 3.84 (s, 3H), 3.80 (s, 3H).

EXAMPLE 62D 2-(3-chloro-1-methylindol-5-yl)-5-(3,4,5-trimethoxyphenyl)-Δ2,3-oxazoline Example 62B (199.4 mg, 0.476 mmol) was processed as described in Example 4B to provide 78.4 mg of the desired product.

MS (ESI(+)) m/z 401 (M+H)$^+$;

$^1$H NMR (CDCl$_3$) δ 8.31 (d, J=1.5 Hz, 1H), 7.97 (dd, J=1.47 Hz, 10.3, 1H), 7.36 (d, J=8.8 Hz, 1H), 6.61 (s, 2H), 5.64–5.58 (m, 1H), 4.53–4. 45 (m, 1H), 3.85 (s, 6H), 3.81(s, 3H);

Anal. calcd for C$_{21}$H$_{21}$N$_2$O$_4$Cl: C, 62.92; H, 5.28; N, 6.99. Found: C, 62.63; H, 5.17; N, 6.70.

EXAMPLE 63

2-(7-fluoro-5-indolvl)-5-(3,4,5-trimethoxyphenyl)-Δ2,3-oxazoline

EXAMPLE 63A 3-fluoro-4-nitrophenyl triflate

To a mixture of 3-fluoro-4-nitrophenol (0.628 g, 4 mmol) and triethyl amine (1.62 g, 16 mmol) in 50 ml of anhydrous Dichloromethane was added trifluoromethanesulfonyl anhydride (2.27 g, 8 mmol) by syringe at 0° C. The solution was stirred at that temperature for another 4 hours or until the TLC indicated all starting material was consumed. The solution was poured in 100 ml of water, washed by 5% NaHCO$_3$, brine and , dried (MgSO$_4$), filtered, and concentrated. After filtration, the organic solution was concentrated in vacuo. The crude material was purified by flash chromatography on silica gel eluting with 2:8 Ethyl acetate/Hexanes to provide 1.10 g of the desired product (98%).

$^1$H NMR (CDCl$_3$) δ 8.25 (m, 1H), 7.30 (m, 2H).

EXAMPLE 63B 7-fluoro-5-indole-triflate

A solution of solution of Example 63A (1.10 g, 3.8 mmol) in THF (50 mL) at −40° C. was treated over 5 minutes with 1M vinylmagnesium bromide in THF (11.4 ml, 11.4 mmol), stirred for 1 hour, poured into saturated NH$_4$Cl, and extracted with-ethyl acetate. The extract was washed with brine, dried (MgSO$_4$), filtered, and concentrated. The concentrate was purified by flash chromatography on silica gel with 15:85 ethyl acetate/hexanes to provide 0.315 g of the desired product.

MS (DCIINH$_3$) m/z 283 (M+NH$_4$—H$_2$O)$^+$;

$^1$H NMR (CDCl$_3$) δ 8.65 (br s, 1H), 7.36 (m, 2H), 6.92 (dd, J=10.5, 2.3 Hz, 1H), 6.65 (m, 1H).

EXAMPLE 63C methyl-7-fluoro-5-indole-carboxylate

A mixture of Example 63B (1.188 g, 4.2 mmol), PdCl$_2$ (dppf)$_2$, and triethylamine (1.08 mL, 8.4 mmol) in methanol (40 mL) at 120° C. under carbon monoxide (450 psi) was stirred, for 15 hours, cooled to room temperature, filtered through diatomaceous earth (Celite®), and concentrated. The concentrate was purified by flash chromatography on silica gel with 15:85 ethyl acetate/hexanes to provide 0.63 g of the desired product.

MS (DCI/NH$_3$) m/z 194 (M+H)$^+$ and 21 1(M+NH$_4$)$^+$;

$^1$H NMR (CDCl$_3$) δ 8.65 (br s, 1H), 7.62 (dd, J=1.1, 11.7 Hz, 2H), 6.31 (m, 1H), 6.97 (dd, J=3.3, 5.5 Hz, 1H), 3.94 (s, 3H).

EXAMPLE 63D 7-fluoro-1H-indole-5-carboxylic acid

A mixture of Example 63C (0.22 g, 1.13 mmol) and LiOH (0.136 g, 5.7 mmol) in 1:1 methanol/water (20 ml) was heated at reflux for 2 hours, poured into water (1 mL), and extracted with ethyl acetate. The extract was washed with brine, dried (MgSO$_4$), filtered, and concentrated to provide the desired product which was used in the next step without further purification.

EXAMPLE 63E 7-fluoro-indole-5-carboxylic acid (N-[2-hydroxy-2-(3,4,5-trimethoxyphenyl) ethyl]) amide A solution of Example 63D in DMF (10 mL)was treated sequentially with 2-amino-1-(3,4,5-trimethoxyphenyl) ethanol hydrochloric acid salt (0.343 g, 1.30 mmol), EDC (0.325 g, 1.7 mmol), triethylamine, DMAP (catalytic), heated at 50° C. for 15 hours, cooled to room temperature, poured into water (100 ml), and extracted with ethyl acetate. The extract was washed with brine, dried (MgSO$_4$), filtered, and concentrated. The concentrate was purified by flash chromatography on silica gel with 8:2 ethyl acetate/hexanes to provide 0.24 g of the desired product.

MS (DCI/NH$_3$) m/z 371 (M+H)$^+$ and 389 (M+NH$_4$)$^+$;

$^1$H NMR (CDCl$_3$) δ 8.51 (br s, 1H), 7.75 (s, 1H), 7.41 (d, J=11.2 Hz, 1H), 7.32 (m, 11H), 6.65 (s, 2H), 6.55 (m, 1H), 4.95 (m, 1H), 3.6–4.0 (m, 11H).

EXAMPLE 63F 2-(7-fluoro-5-indolyl)-5-(3,4,5-trimethoxyphenyl)-Δ2,3-oxazoline A mixture of Example 63E (0.24 g, 0.62 mmol) and Burgess's agent (0.176 g, 0.74 mmol) in of anhydrous THF (10 mL) was heated at reflux for 1 hour, cooled to room temperature, poured into water (50 mL), and extracted with ethyl acetate. The extract was washed with brine, and, dried (MgSO$_4$), filtered, and concentrated. The solution was concentrated under vacuum. The concentrate was purified by flash column chromatography on silica gel to provide 0.15 g of the desired product.

MS (ESI(+)) m/z 371 (M+H)$^+$;

$^1$H NMR (DMSO-d$_6$) δ 11.96 (s, 1H), 8.00 (s, 1H), 7.52 (s, 1H), 7.48 (dd, J=0.7, 12.1 Hz, 1H), 6.69 (s, 2H), 6.66 (s, 1H), 5.70 (m, 1H), 4.38 (m, 1H), 3.78 (m, 1H), 3.76 (s, 6H), 3.65 (s, 3H);

Anal. calcd for C$_{20}$H$_{19}$N$_2$O$_4$F: C, 64.86; H, 5.17; N, 7.56. Found: C, 65.05; H, 5.20; N, 7.43.

EXAMPLE 64

2-(1-methyl-7-fluoro-5-indolyl)-5-(3,4,5-trimethoxyphenyl)-Δ2,3-oxazoline

Example 63 (0.100 g, 0.27 mmol) in DMF (3 mL) was treated with 60% NaH (92 mg, 2.31 mmol) at 0° C., stirred for 15 minutes, treated with methyl iodide (76 mg, 0.54 mmol) in DMF (1 mL), stirred for 1 hour, treated with water, and extracted with ethyl acetate. The extract was dried (MgSO$_4$), filtered, and concentrated. The concentrate was purified by flash column chromatography on silica gel to provide 101 mg of the desired product.

MS (ESI(+)) m/z 385 (M+H)$^+$;

$^1$H NMR (DMSO-d$_6$) δ 7.98 (s, 1H), 7.45 (m, 2H), 6.68 (s, 2H), 6.61 (m, 1H), 5.68 (m, 1H), 4.20 (m, 1H), 3.98 (s, 3H), 3.90 (m, 1H), 3.74 (s, 6H), 3.65 (s, 3H);

Anal. calcd for C$_{21}$H$_{21}$N$_2$O$_4$F: C, 65.61; H, 5.51; N, 7.29. Found: C, 65.55; H, 5.62; N, 7.24.

EXAMPLE 65

2-(7-chloro-5-indolyl)-5-(3,4,5-trimethoxyphenyl)-Δ2,3-oxazoline

EXAMPLE 65A 1-acetyl-5-bromo-7-chloro-indoline

A mixture of 1-acetyl-5-bromo-indoline (1.20 g, 5 mmol) and N-chlorosucinimide (0.734 g, 5.5 mmol) in acetonitrile (80 mL) was heated to reflux for 12 hours, cooled to room temperature, and concentrated. The concentrate was purified by flash column chromatography on silica gel to provide 0.548 g of the desired product.

MS (ESI(+)) m/z 275 (M+H)$^+$ and 292 (M+NH$_4$)$^+$;

$^1$H NMR (CDCl$_3$) δ 7.38 (m, 1H), 7.27 (m, 1H), 4.17 (t, J=7.7 Hz, 2H), 3.04 (t, J=7.7 Hz, 2H), 2.28 (s, 3H).

EXAMPLE 65B 5-bromo-7-chloro-indoline

Example 65A was hydrolyzed with excess LiOH in methanol/water to provide the desired product.

MS (ESI(+)) m/z 233 (M+H)$^+$ and 250 (M+NH$_4$)$^+$;

$^1$H NMR (CDCl$_3$) δ 7.13 (d, J=1.7 Hz, 1H), 7.07 (d, J=1.3 Hz, 1H), 3.97 (s, 1H), 3.62 (t, J=8.5 Hz, 2H), 3.09 (t, J=8.5 Hz, 2H).

EXAMPLE 65C 5-bromo-7-chloro-indole

A mixture of Example 65B (0.120 g, 0.55 mmol) and salcomine (0.022 g, 0.06 mmol) in methanol (30 mL) was treated with oxygen over 18 hours and concentrated. The concentrate was purified by flash column chromatography on silica gel to provide 0.112 g of the desired product. MS (ESI(+)) m/z 232 (M+2) and 248 (M+NH$_4$)$^+$;

$^1$H NMR (CDCl$_3$) δ 8.38 (s, 1H), 7.67 (dd, J=1.7, 0.6 Hz, 1H), 7.33 (d, J=1.7 Hz, 1H), 7.26 (m, 1H), 6.53 (dd, J=2.0, 3.1 Hz, 1H).

EXAMPLE 65D methyl-7-chloro-5-indole-carboxylate

5-Bromo-7-chloro-indole was processed as described in Example 63C to provide the desired product.

MS (ESI(+)) m/z 210 (M+H)$^+$ and 227 (M+NH$_4$)$^+$;

$^1$H NMR (CDCl$_3$) δ 8.58 (s, 1H), 8.33 (s, 1H), 7.92 (d, J=1.1 Hz, 1H), 7.33 (m, 1H), 6.70 (dd, J=2.2, 2.9 Hz, 1H), 3.94(s, 3H).

EXAMPLE 65E 2-(7-chloro-5-indolyl)-5-(3,4,5-trimethoxyphenyl)-Δ2,3-oxazoline Example 65D was processed as described in Examples 63D and 63E to provide the desired product.

MS (ESI(+)) m/z 387 (M+H)$^+$;

$^1$H NMR (DMSO-d$_6$) δ 11.85 (s, 1H), 8.13 (d, J=1.1 Hz, 1H), 7.72 (d, J=1.1 Hz, 1H), 7.52 (d, J=2.9 Hz, 1H), 6.69 (m, 3H), 5.70 (m, 1H), 4.78 (m, 1H), 3.78 (m, 1H), 3.76 (s, 6H),3.65 (s, 3H);

Anal. calcd for C$_{20}$H$_{19}$N$_2$OCl.0.22CH C(O)OCH2 CH3 C, 61.74; H, 5.15; N, 6.90. Found: C, 61.51; H, 4.97; N, 7.06.

EXAMPLE 66

2-(1-methyl-7-chloro-5-indolyl)-5-(3,4,5-trimethoxyphenyl)-Δ2,3-oxazoline

Example 65 was processed as described in Example 60 to provide the desired product.

MS (ESI(+)) m/z 401 (M+H)$^+$;

$^1$H NMR (DMSO-d$_6$) δ 8.10 (d, J=1.3 Hz, 1H), 7.68 (d, J=1.2 Hz, 1H), 7.52 (s, J=3 Hz, 1H), 6.68 (s, 2H), 6.63 (d, J=2.9 Hz, 1H), 5.65 (m, 1H), 4.37 (m, 1H), 4.13 (s, 3H), 3.88 (m, 1H), 3.76 (s, 6H), 3.66 (s, 3H);

Anal. calcd for C$_{21}$H$_{21}$N$_2$O$_4$Cl: C, 62.92; H, 5.28; N, 6.99. Found: C, 62.72; H, 5.43; N, 6.73.

EXAMPLE 67

2-(3-fluoro-5-indolyl)-5-(3,4,5-trimethoxyphenyl)-Δ2,3-oxazoline

EXAMPLE 67A methyl-3-fluoro-5-indole-carboxylate

A solution of methyl 5-indole carboxylate (1.75 g, 10 mmol) and N-fluoro-2,4,6-trimethylpyridinium triflate (3.75 g, 13 mmol) in methanol (100 mL) was heated at reflux for 18 hours and concentrated. The concentrate was purified by flash column chromatography on silica gel to provide 200 mg of the desired product.

MS (ESI(+)) m/z 194 (M+H)$^+$ and 211 (M+NH$_4$)$^+$;

$^1$H NMR (CDCl$_3$) δ 8.42 (s, 1H), 7.92 (dd, J=1.7, 8.9 Hz, 1H), 7.92 (d, J=1.1 Hz, 1H), 7.80 (s, 1H), 7.34 (dd, J=2.4, 8.9 Hz, 1H), 7.04 (d, J=2.8 Hz, 1H), 3.94 (s, 3H).

EXAMPLE 67B 3-fluoro-indole-5-carboxylic acid (N-(2-hydroxy-2-(3,4,5-trimethoxyphenyl) ethyl amide Methyl-3-fluoro-5-indole-carboxylate was processed as described in Example 63D to provide the desired product.

MS (ESI(+)) m/z 389 (M+H)$^+$ and 406 (M+NH$_4$);

$^1$H NMR (CDCl$_3$) δ 8.08 (s, 1H), 7.90 (s, 1H), 7.67 (dd, J=1.9, 8.8 Hz, 1H), 7.32 (dd, J=2.2, 8.5 Hz, 1H), 7.05 (m, 1H), 6.51 (s, 2H), 6.66 (s, 2H), 6.63 (m, 1H), 4.95 (m, 1H), 3.91 (m, 1H), 3.85 (s, 9H), 3.70 (m, 1H), 3.60 (m, 1H).

EXAMPLE 67C 2-(3-fluoro-5-indolyl)-5-(3,4,5-trimethoxyphenyl)-Δ2,3-oxazoline Example 67B was processed as described in Example 63E to provide the desired product.

MS (ESI(+)) m/z 370 (M+H)$^+$;

$^1$H NMR (DMSO-d$_6$) δ 11.18 (m, 1H), 8.07 (d, J=1.0 Hz, 1H), 7.78 (m, 1H), 7.47–7.52 (m, 1H), 6.69 (s, 2H), 5.68 (m, 1H), 4.38 (m, 1H), 3.86 (m, 1H), 3.76 (s, 6H), 3.66 (s, 3H);

HRMS: Calcd. (M+H)$^+$: 371.1407. Found: 371.1414.

EXAMPLE 68

(2-(1-methyl-3-fluoro-5-indolyl)-5-(3,4,5-trimethoxyphenyl)-Δ2,3-oxazoline

Example 67 was processed as described in Example 60 to provide the desired product.

MS (ESI(+)) m/z 370 (M+H)$^+$;

$^1$H NMR (DMSO-d$_6$) δ 8.08 (s, 1H), 7.83 (d, J=8.5 Hz, 1H), 7.58 (d, J=8.8 Hz, 1H), 6.69 (s, 2H), 5.69 (m, 1H), 4.38 (m, 1H), 3.86 (m, 1H), 3.75–3.77 (m, 9H), 3.65 (s, 3H);

Anal. calcd for C$_{21}$H$_2$IN$_2$O$_4$F: C, 65.61; H, 5.51; N, 7.29. Found: C, 65.56; H, 5.78; N, 7.00.

EXAMPLE 69

2-(1-hydroxymethylindol-5-yl)-5-(3,4,5-trimethoxyphenyl)-Δ2,3-oxazoline

A mixture of Example 11 (0.716 g, 0.500 mmol) in ethanol (3 mL) was treated sequentially with 37% aqueous formaldehyde (2.5 mL) and 1M NaOH (10 drops), stirred for 3.5 hours to form a thick, white precipitate, treated with water (60 mL) and brine (20 mL), and extracted sequentially with 1:1 dichloromethane/ethyl acetate (80 mL) and dichloromethane (20 mL). The combined extracts were washed with brine (25 mL), dried (MgSO$_4$), filtered, and concentrated to provide 146 mg of the desired product.

$^1$H NMR (DMSO-d6) δ 3.65 (s, 3H), 3.75 (s, 6H), 3.87 (dd, J=7.9, 14.5 Hz, 1H), 4.38 (dd, J=9.7, 14.5 Hz, 1H), 5.55 (d, J=7.2 Hz, 2H), 5.68 (dd, J=7.9, 9.7 Hz, 1H), 6.53 (t, J=7.2 Hz, 1H), 6.57 (d, J=3.0 Hz, 1H), 6.69 (s, 2H), 7.50 (d, J=3.0 Hz, 1H), 7.64 (d, J=8.6 Hz, 1H), 7.79 (dd, J=1.0, 8.6 Hz, 1H), 8.16 (d, J=1.0 Hz, 1H);

HRMS (FAB) Calc. (M+H)$^+$ for C$_{21}$H$_{23}$N$_2$O$_5$: 383.1607. Found:. 383.1611.

Anal. calcd for C$_{21}$H$_{22}$N$_2$O$_5$ 0.30 H$_2$O: C, 65.04; H, 5.87; N, 7.22. Found: C, 65.06; H, 5.88; N, 7.20.

EXAMPLE 70

2-(1-methoxymethyl-5-indolyl)-5-(3,4,5-trimethoxyphenyl)-Δ2,3-oxazoline

A slurry of NaH (0.120 g, 3.00 mmol) in DMF (1.5 mL) at 0° C. was treated in one portion with Example 11 (0.106 g, 0.300 mmol), stirred for 5 minutes, treated with methoxymethyl chloride (29.0 mg, 0.360 mmol), warmed to room temperature over 20 hours, cooled to 0° C., carefully quenched with methanol, added to water (20 mL), treated with 10% NaHCO$_3$ (10 mL) and brine (10 mL), and extracted with ethyl acetate (20 mL then 3×10 mL). The combined extracts were, dried (MgSO$_4$), filtered through a short plug of silica gel with ethyl acetate rinses, and concentrated. The concentrate was purified by radial chromatography with 98:2 dichloromethane/methanol to provid the 82.4 mg of the desired product.

$^1$H NMR (CDCl$_3$) δ 3.26 (s, 3H), 3.85 (app s, 9H), 4.01 (dd, J=8.2, 14.6 Hz, 1H), 4.48 (dd, J=10.0, 14.6 Hz, 1H), 5.48 (s, 2H), 5.60 (dd, J=8.2, 10.0 Hz, 1H), 6.60 (s, 2H), 6.60–6.61 (m, 1H), 7.23 (d, J=3.4 Hz, 1H), 7.53 (d, J=8.6 Hz, 1H), 7.96 (dd, J=1.4, 8.6 Hz, 1H), 8.32 (d, J=1.4 Hz, 1H);

HRMS (FAB) Calc. (M+H)$^+$ for C$_{22}$H$_{25}$N$_2$O$_5$: 397.1763. Found:. 397.1752.

Anal. calcd for C$_{22}$H$_{24}$N$_2$O$_5$ 1.6 H$_2$O: C, 66.65; H, 6.10; N, 7.07. Found: C, 62.12; H, 5.61; N, 6.25.

EXAMPLE 71

2-(1,2-dimethyl-5-indolyl)-4,5-trimethoxyphenyl)-Δ2,3-oxazoline

EXAMPLE 71A ethyl 2-methyl-3-thiomethoxy-5-indolecarboxylate

A solution of ethyl 4-aminobenzoate (2.53 g, 15.0 mmol) in dichloromethane (75 mL) at −70° C. was treated dropwise with trimethylacetyl chloride (1.62 g, 14.9 mmol) in dichloromethane (7.5 mL), stirred for1 hour, treated dropwise with a a solution of (methylthio)acetone (1.59 g, 15.0 mmol) in dichloromethane (7.5 mnL), stirred for 1.25 hours, treated with triethylamine (1.52 g, 15.0 mmol), stirred for 10 minutes, warmed to room temperature, stirred for 16 hours, washed with water (15 mL), dried (MgSO$_4$), filtered, and concentrated. The concentrate was purified by flash column chromatography with 1:4 hexane/dichloromethane to provide the desired product.

MS (ESI(+)) m/z 50 (M+H)$^+$;

$^1$H NMR (DMSO-d$_6$) δ 1.43 (t, J=7.0 Hz, 3H), 2.20 (s, 3H), 2.48 (s, 3H), 4.32 (q, J=7.0 Hz, 2H), 7.39 (d, J=8.5 Hz, 1H), 7.72 (dd, J=1.7, 8.5 Hz, 1H), 8.17 (d, J=1.7 Hz, 1H), 11.68–11.72 (br, 1H).

EXAMPLE 71B ethyl 2-methyl-5-indolecarboxylate

A solution of ethyl 2-methyl-3-thiomethoxy-5-indolecarboxylate (1.90 g, 7.62 mmol) in ethanol (60 mL) at room temperature was treated with Raney Ni (approximately 3 teaspoons), stirred for 17 hours, filtered, and concentrated to provide 1.51 g of the desired product.

MS (ESI(+)) m/z 204 (M+H)+;

$^1$H NMR (DMSO-d$_6$) δ 1.32 (t, J=7.0 Hz, 3H), 2.40 (s, 3H), 4.28 (q, J=7.0 Hz, 2H), 6.27 (s, 1H), 7.33 (d, J=2.4 Hz, 1H), 7.64 (dd, J=1.8, 8.4 Hz, 1H), 7.10 (d, J=1.8 Hz, 1H), 11.32 (s, 1H).

EXAMPLE 71C ethyl 1 2-dimethyl-5-indolecarboxylate

A 60% oil dispersion of NaH (1.51 g, 7.43 mmol) was rinsed with THF (2×10 mnL), slurried in DMF (35 mL), and cooled to 0° C. This slurry was treated dropwise with ethyl 1,2-dimethyl-5-indolecarboxylate (1.51 g, 7.43 mmol) in DMF (5 mL), stirred for 5 minutes, treated with methyl iodide (1.11 g, 7.80 mmol), warmed to room temperature, stirred for 4 hours, treated with ethyl acetate (25 nlL), cooled to 0° C., treated with ethanol (approximately 5 mL), treated with ethyl acetate (125 mL), washed sequentially with 2:1:1 water/saturated Na$_2$CO$_3$/brine (100 mL then 2×50 mL) and brine (50 mL), dried (MgSO$_4$), filtered, through silica gel with ethyl acetate rinses, and concentrated to provide 1.61 g of the desired product.

MS (ESI(+)) m/z 218 (M+H)+.

EXAMPLE 71D 2-(1,2-dimethyl-5-indolyl)-4,5-trimethoxyphenyl)-Δ2,3-oxazoline

Ethyl 1,2-dimethyl-5-indolecarboxylate was processed as described in Examples 63D and 63E to provide 155 mg of the desired product.

MS (ESI(+)) m/z 381 (M+1);

$^1$H NMR (DMSO-d$_6$) δ 2.42 (s, 3H), 3.65 (s, 3H), 3.70 (s, 3H), 3.75 (s, 6H), 3.85 (dd, J=8.0, 14.5 Hz, 1H), 4.36 (dd, J=9.9, 14.5 Hz, 1H), 5.65 (dd, J=8.0, 9.9 Hz, 1H), 6.33 (s, 1H), 6.68 (s, 2H), 7.46 (d, J=8.7 Hz, 1H), 7.69 (dd, J=1.4, 8.7 Hz, 1H), 8.03 (d, J=1.4 Hz,

Anal. calcd for C$_{22}$H$_{24}$N$_2$O$_4$ 0.55 H$_2$O: C, 67.69; H, 6.48; N, 7.18. Found: C, 67.75; H, 6.45;N, 7.13.

EXAMPLE 72

2-(7-methyl-5-indolyl)-5-(3,4,5-trimethoxyphenyl)-Δ2,3-oxazoline

EXAMPLE 72A 3-methyl-4-nitrophenyl trifluoromethanesulfonate

A solution of 3-methyl-4-nitrophenol, Example 72A, (5.00 g, 32.6 mmol) and triethylamine (9.90 g, 97.8 mmol) in dichloromethane (100 mL) at 0° C. was treated dropwise over 30 minutes with trifluoromethanesulfonic anhydride (18.4 g, 65.2 mmol), warmed to room temperature, stirred for 22 hours, and transferred to 10% NaHCO$_3$ (200 mL). The organic phase was separated, and the aqueous phase was extracted with dichloromethane (30 mL). The combined extracts were washed with brine (30 mL), dried (MgSO$_4$), filtered through silica gel with 1:1 hexane/dichloromethane rinses, and concentrated. The concentrate was purified by flash column chromatography eluting with 98:2 hexane/ethyl acetate to provide 9.56 g of the desired product.

MS (ESI(−)) m/z 284 (M−H)−; $^1$H NMR (CDCl$_3$) δ 2.67 (s, 3H), 7.26–7.31 (m, 2H), 8.08–8.12 (m, 1H).

EXAMPLE 72B 7-methyl-5-indolyl trifluoromethanesulfonate

A solution of 3-methyl-4-nitrophenyl trifluoromethanesulfonate (8.96 g, 31.4 mmol) in THF (200 mL) at 0° C. was treated dropwise with 1M allylmagnesium bromide in THF (110 mL 110 mmol), stirred for 2 hours, transferred into saturated NH$_4$Cl (200 mL), and extracted with ethyl acetate (200 mL). The extract was dried (MgSO$_4$), filtered, and concentrated. The concentrate was purified by flash column chromatography with 9:1 hexanes/ethyl acetate to provide 3.19 g of the desired product.

MS (ESI(−)) m/z 278 (M−H)−;

$^1$H NMR (CDCl$_3$) δ 2.51 (s, 3H), 6.60 (t, J=2.8 Hz, 1H), 6.91 (d, J=1.8 Hz, 1H), 7.30 (t, J=2.8 Hz, 1H), 7.39 (d, J=1.8 Hz, 1H), 8.28–8.14 (br, H).

EXAMPLE 72C 7-methyl-5-indolecarboxilic acid

A solution of 7-methyl-5-indolyl trifluoromethanesulfonate (3.19 g, 11.4 mmol), triethylamine, and 1,1′-bis (diphenylphosphino)ferrocene palladium (II) chloride (catalytic)in 9:1 THF/water was stirred under CO$_2$ (500 psi) until HPLC indicated complete conversion. The solution was treated with water (30 mL), adjusted to pH 4–5, and extracted sequentially with ethyl acetate (100 mL) and dichloromethane (3×40 mL). The combined extracts were dried (Na$_2$SO$_4$), filtered, and concentrated to provide the desired product which was used in the next step without further purification.

EXAMPLE 72D 2-(7-methyl-5-indolyl)-5-(3,4,5-trimethoxyphenyl)-Δ2,3-oxazoline Example 72C was processed as described in Example 63E to provide the desired product.

$^1$H NMR (DMSO-d$_6$) δ 2.44 (s, 3H), 3.59 (s, 3H), 3.68 (s, 6H), 3.78 (dd, J=7.8, 14.6 Hz, 1H), 4.29 (dd, J=10.0, 14.6 Hz, 1H), 5.58 (dd, J=7.8, 10.8 Hz, 1H), 6.47–6.49 (m, 1H), 6.61 (s, 2H), 7.34 (app t, J=2.8 Hz, 1H), 7.46 (s, 1H), 7.94 (s, 1H), 11.27 (s, 1H);

HRMS (FAB) Calc. (M+H) for C$_{21}$H$_{23}$N$_2$O$_4$: 367.1658. Found. 367.1668.

Anal. calcd for C$_{21}$H$_{22}$N$_2$O$_4$ 0.45 H$_2$O: C, 67.35; H, 6.16; N, 7.48. Found: C, 67.29; H, 6.21; N, 7.45.

EXAMPLE 73

2-(1,7-dimethyl-5-indolyl)-5-(3,4,5-trimethoxyphenyl)-Δ2,3-oxazoline

Example 72 (141 mg, 0.385 mmol) was processed as described Example 64 to provide 113 mg of the desired product. $^1$H NMR (DMSO-d$_6$) δ 2.76 (s, 3H), 3.64 (s, 3H), 3.74 (s, 6H), 3.85 (dd, J=7.8, 14.6 Hz, lH), 4.07 (s, 3H), 4.36 (dd, J=9.8, 14.6 Hz, 1H), 5.64 (dd, J=7.8, 9.8 Hz, 1H), 6.48 (d, J=3.0 Hz, 1H), 6.67 (s, 2H), 7.30 (d, J=3.0 Hz, 1H), 7.46 (s, 1H), 7.95 (d, J=1.3 Hz, 1H);

HRMS (FAB) Calc. (M+H)+for C$_{22}$H$_{25}$N$_2$O$_4$: 381.1814. Found: 381.1824.

Anal. calcd for C$_{22}$H$_{24}$N$_2$O$_4$: C, 69.46; H, 6.36; N, 7.36. Found: C, 69.20; H, 6.43; N, 7.12.

EXAMPLE 74

2-(1,2,7-trimethylindol-5-yl)-5-(3,4,5-trimethoxyphenyl)-Δ2,3-oxazoline

3-Methyl-4-aminobenzoate was processed as described in Examples 71A–D to provide the desired product.

¹H NMR (CDCl₃) δ 2.40 (s, 3H), 2.79 (s, 3H), 3.83 (s, 6H), 3.84 (s, 3H), 3.95 (s, 3H), 3.95–4.02 (m, 1H), 4.45 (dd, J=10.0, 14.6 Hz, 1H), 5.56 (dd, J=7.8, 10.0 Hz, 11H), 6.29 (d, 1J=.0 Hz, 1H), 6.59 (s, 2H), 7.55–7.57 (m, 1H), 8.00–8.01 (m, 1H);

HRMS (FAB) Calc. (M+H)+for $C_{23}H_{27}N_2O_4$: 395.1971. Found. 395.1962.

Anal. calcd for $C_{23}H_{26}N_2O_4$ 0.65 H20: C, 68.01; H, 6.77; N, 6.90. Found: C, 68.08; H, 6.40; N, 6.61.

EXAMPLE 75

2-(1,2-dimethylbenzimidazol-5-yl)-5-(3,4,5-trimethoxcyphenyl)-Δ2,3-oxazoline

EXAMPLE 75A methyl 3-amino-4-methylaminobenzoate

A solution of methyl 3,4-dinitrobenzoate (38.9 g, 172 mmol) in methanol (200 mL) at 0° C. was treated with 2M methylamine in methanol (350 mL 700 mmol) warmed to room temperature, stirred for 64 hours, and concentrated. The concentrate was slurried in methanol (100 mL), treated with 10% Pd/C (10 g, 9.4 mmol), stirred under hydrogen (1 atm) for 22 hours, diluted with ethyl acetate (1 L), filtered through silica gel, and concentrated to provide 27.0 g of the desired product.

MS (DCIINH₃) m/z 181 (M+H)⁺;

¹H NMR (DMSO-d₆) δ 2.77 (d, J=5.1 Hz, 3H), 3.72 (s, 3H), 4.67 (s, 2H), 5.39 (q, J=5.1 Hz, 1H), 6.39 (d, J=8.4 Hz, 1H), 7.18 (d, J=2.1 Hz, 1H), 7.25 (dd, J=2.1, 8.4 Hz, 1H).

EXAMPLE 75B methyl 3-acetylamino-4-methylaminobenzoate

A solution of Example 75A (1.80 g, 10.0 mmol) in dichloromethane (100 mL) was treated sequentially with acetic anhydride (3.06 g, 30.0 mmol) and 10% NaHCO₃ (100 mL) and stirred for 30 minutes. The organic layer was separated, washed with brine (30 mL), dried (MgSO₄), filtered, concentrated until solid precipitated, treated with diethyl ether, and filtered to provide 1.66 g of desired product.

MS (ESI(+)) m/z 223 (M+H)⁺;

¹H NMR (DMSO-d₆) δ 2.04 (s, 3H), 2.78 (d, J=5.4 Hz, 3H), 3.75 (s, 3H), 5.93 (q, J=5.4 Hz, 1H), 6.60 (d, J=8.5 Hz, 1H), 7.67 (dd, J=1.7, 8.5 Hz, 1H), 7.70 (d, J=1.7 Hz, 1H), 9.07 (s, 1H).

EXAMPLE 75C methyl 1,2-dimethylbenzimidazole-5-carboxylate

A solution of Eaton's reagent (1:10 P2O5/methane sulfonic acid) (30 mL) was treated portionwise with Example 75B (1.66 g, 7.47 mmol), heated to 110° C. for 1 hour, transferred to 10% NaHCO₃ (300 mL), and extracted with ethyl acetate (300 mL then 2×100 mL). The combined extracts were washed with brine (100 imL), dried (MgSO₄), filtered, and concentrated to provide 987 mg of the desired product as a solid.

MS (ESI(−)) m/z 383 (M−H)⁻;

¹H NMR (DMSO-d₆) δ 3.71 (s, 3H), 3.83–3.86 (m, 9H), 7.01 (s, 2H), 7.48–7.64 (m, 2H), 7.70 (dd, J=1.7, 8.5 Hz, 1H), 8.41 (s, 1H), 11.17 (s, 1H), 11.80 (s, 1H).

EXAMPLE 75D 2-(1,2-dimethylbenzimidazol-5-yl)-5-(3,4,5-trimethoxyphenyl)-Δ2,3-oxazoline Example 75C was processed as described in Examples 63D and 63E to provide the desired product.

¹H NMR (DMSO-d₆) δ 2.56 (s, 3H), 3.65 (s, 3H), 3.75 (s, 6H), 3.77 (s, 3H), 3.88 (dd, J=8.1, 14.7 Hz, 1H), 4.39 (dd, J=10.0, 14.7 Hz, 1H), 5.69 (dd, J=8.1, 10.0 Hz, 1H), 6.70 (s, 2H), 7.58 (d, J=8.8 Hz, 1H), 7.83 (dd, J=1.5, 8.8 Hz, 1H), 9.05 (d, J=1.5 Hz, 1H).

HRMS (FAB) Calc. (M+H) for $C_{21}H_{24}N_3O_4$: 382.1767. Found:. 382.1750.

EXAMPLE 76

2-(3-trifluoroacetyl-5-indolyl)-5-(3,4,5-trimethoxyphenl)-Δ2,3-oxazoline

EXAMPLE 76A methyl 3-trifluoroacetyl-5-indolecarboxylate

A solution of trifluoroacetic anhydride (5.25 g, 25.0 mmol) in dichloroethane (50 mL) at 0° C. was treated with methyl 5-indolecarboxylate (0.876 g, 5.0 mmol), warmed gradually to room temperature, stirred for 24 hours, and treated with pentane to provide 1.06 g of the desired product MS (ESI(+)) m/z 272 (M+H)⁺.

EXAMPLE 76B 2-(3-trifluoroaceiyl-5-indolyl)-5-(3,4,5-trimethoxyphenyl)-Δ2,3-oxazoline Example 76A was processed as described in Examples 63D and 63E to provide 279 mg of the desired product.

¹H NMR (CDCl₃) δ 3.86 (s, 6H), 3.87 (s, 3H), 4.03–4.05 (m, 1H), 4.53 (dd, J=10.0, 14.6 Hz, 1H), 5.70 (dd, J=8.2, 10.0 Hz, 1H), 6.62 (s, 2H), 7.44 (d, J=8.5 Hz, 1H), 8.00 (dd, J=1.3, 8.5 Hz, 1H), 9.08 (d, J=1.3 Hz, 1H), 9.00 (s, 1H), 10.60 (s, 1H).

HRMS (FAB) Calc. (M+H) for $C_{22}H_{20}F_3N_2O_5$: 449.1324. Found 449.1330.

EXAMPLE 77

2-(1-methyl-3-trifluoroacetylindol-5-yl)-5-(3,4,5-trimethoxyphenyl)-Δ2,3-oxazoline Methyl 1-methyl-5-indolecarboxylate was processed as described in Example 76A to provide 325 mg of the desired product.

¹H NMR (DMSO-d₆) δ 3.66 (s, 3H), 3.76 (s, 6H), 3.94 (dd, J=7.9, 14.9 Hz, 1H), 4.00 (s, 3H), 4.42 (dd, J=9.9, 14.7 Hz, 1H), 5.70 (dd, J=7.9, 9.9 Hz, 1H), 6.71 (s, 2H), 7.80 (d, J=8.7, 1H), 8.02 (dd, J=1.6, 8.7 Hz, 1H), 8.69 (d, J=1.6 Hz, 1H), 8.77–8.78 (m, 1H); HRMS (FAB) Calc. (M+H)+for $C_{23}H_{22}F_3N_2O_5$: 463.1481. Found: 463.1470.

Anal. calcd for $C_{23}H_{21}F_3N_2O_5$: C, 59.74; H, 4.58; N, 6.06. Found: C, 59.50; H, 4.76; N, 6.00.

EXAMPLE 78

2-(1-(2,22-trifluoroethyl)indol-5-yl)-5-(3,4,5-trimethoxyphenyl)-Δ2,3-oxazoline

EXAMPLE 78A 5-benzyloxy-1-trifluoroacetylindole

A solution of trifluoroacetic anhydride (12.7 g, 60.0 mmol) in dichloroethane (80 mL) at 0° C. was treated dropwise with a solution of 5-benzyloxyindole (3.34 g, 15.0 mmol) in dichloroethane (40 mL), stirred for 18 hours, diluted with ethyl acetate (200 m]L), washed sequentially with 10% NaHCO₃ (300 mnL), 2:1:1 water/10% NaHCO3/brine (2×100 mL), and brine (50 mL), dried (MgSO4), filtered, and concentrated to provide 2.33 g of the desired product.

MS (ESI(−)) rn/z 318 (M−H)⁻;

¹H NMR (DMSO-d₆) δ 5.18 (s, 2H), 6.93 (d, J=4.1 Hz, 1H), 7.13 (dd, J=2.6, 8.8 Hz, 1H), 7.32–7.36 (m, 2H), 7.37–7.43 (m, 2H), 7.45–7.50 (m, 2H), 7.71–7.75 (m, 1H), 8.21 (d, J=8.8 Hz, 1H).

EXAMPLE 78B 5-benzyloxy-1-(2,2,2-trifluoroethyl)indole

A solution of Example 78A (1.98 g, 6.20 mmol) in THF (20 mL) at 0° C. was treated dropwise with 1M BH₃ THF in THF (11.2 mL, 11.2 mmol), heated at reflux for 16 hours, cooled to 0° C., treated 6M HCl (approximately 1 mL), diluted with ethyl acetate (60 mL), washed with 10% NaHCO₃ (30 mL) and brine (30 mL), dried (MgSO₄), filtered, and concentrated to provide 1.56 g of the desired compound.

MS (ESI(+)) m/z 306 (M+H)⁺;

¹H NMR (DMSO-d₆) δ 5.10 (s, 2H), 5.18 (q, J=9.4 Hz, 2H), 6.44 (d, J=3.3 Hz, 1H), 6.92 (dd, J=2.2, 9.0 Hz, 1H), 7.16 (d, J=2.2 Hz, 1H), 7.29–7.38 (m, 2H), 7.38–7.42 (m, 2H), 7.44–7.52 (m, 3H).

EXAMPLE 78C 5-hydroxy-1-(2,2,2-trifluoroethyl)indole

A solution of 5-benzyloxy-1-(2,2,2-trifluoroethyl)indole (1.56 g, 4.09 mmol) in dichloromethane (10 mL) at 0° C. was treated dropwise with 1M BBr3 in dichloromethane (5.73 mL, 5.73 mmol), stirred for 2 hours, transferred to 2:1:1 water/10% NaHCO₃/brine (100 mL), and extracted with ethyl acetate (100 mL). The extract was washed with brine (40 mL), dried (MgSO₄), filtered, and concentrated. The concentrate was purified by flash column chromatography with 9:1 hexane/ethyl acetate to provide 118 mg of the desired product.

MS (ESI(+)) m/z 218 (M+H)⁺;

¹H NMR (CDCl₃) δ 4.59 (q, J=6.2 Hz, 2H), 6.47 (d, J=3.0 Hz, 1H), 6.84 (dd, J=2.4, 8.8 Hz, 1H), 7.04 (d, J=2.4 Hz, 1H), 7.07 (d, J=3.0 Hz, 1H), 7.21 (d, J=8.8 Hz, 1H).

EXAMPLE 78D 1-(2,2,2-trifluoroethyl)-5-indolyl trifluoromethanesulfonate

5-Hydroxy-1-(2,2,2-trifluoroethyl)indole (114 mg, 0.53 mmol) was processed as described in Example 76A to provide 84.3 mg of the desired product.

MS (ESI(+)) m/z 349 (M+H)⁺;

¹H NMR (CDCl ) δ 4.66 (q, J=8.5 Hz, 2H), 6.66 (d, J=3.4 Hz, 1H), 7.17 (dd, J=2.4, 8.8 Hz, 1H), 7.22 (d, J=3.4 Hz, 1H), 7.37 (d, J=8.8 Hz, 1H), 7.55 (d, J=2.4 Hz, 1H).

EXAMPLE 78E 1-(2,2,2-trifluoroethyl)-5-indolecarboxylic acid

A solution of 1-(2,2,2-trifluoroethyl)-5-indolyl trifluoromethanesulfonate (84.3 mg, 0.243 mmol) and 1,1'-bis(diphenylphosphino)ferrocene palladium (II) (catalytic) in methanol was stirred under carbon dioxide (500 psi), until HPLC indicated complete conversion, and concentrated. The concentrate was hydrolyzed as described previously to provide 59.1 mg of the desired product.

¹H NMR (CDCl₃) δ 4.70 (q, J=8.5 Hz, 2H), 6.74 (d, J=3.3 Hz, 1H), 7.20 (d, J=3.3 Hz, 1H), 7.28 (d, J=8.5 Hz, 1H), 7.40 (d, J=8.5 Hz, H), 8.04 (dd, J=0.9, 8.5 Hz, 1H), 8.49 (s, 1H).

EXAMPLE 78F 2-(1-(2,2,2-trifluoroethyl)indol-5-yl)-5-(3,4,5-trimethoxyphenyl)-Δ2,3-oxazoline 1-(2,2,2-Trifluoroethyl)-5-indolecarboxylic acid (71.5 mg, 0.294 mmol) was processed as described in Example 4 to provide 20.4 mg of the desired product.

¹H NMR (DMSO-d₆) δ 3.65 (s, 3H), 3.75 (s, 6H), 3.87 (dd, J=7.6, 14.8 Hz, 1H), 4.39 (dd, J=10.0, 14.8 Hz, 1H), 5.25 (q, J=9.5 Hz, 2H), 5.66 (dd, J=7.6, 10.0 H, 1H), 6.67–6.70 (m, 3H), 7.49 (d, J=3.4 Hz, 1H), 7.70 (d, J=8.8 Hz, 1H), 7.82 (dd, J=1.4, 8.8 Hz, 1H), 8.19 (d, J=1.4 Hz, 1H).

HRMS (FAB) Calc. (M+H) for C₂₂H₂₂F₃N₂O₄: 435.1532. Found: 435.1537. H

EXAMPLE 79

2-(1-cyclopropyl-5-indolyl)-5-(3,4,5-trimethoxyphenyl)-Δ2,3-oxazoline

EXAMPLE 79A 3-bromo-4-cyclopropylaminobenzonitrile

A solution of 3-bromo-4-fluorobenzonitrile (9.33 mmol) and cyclopropylamine (7.90 g, 136 mmol) in methanol (60 mL) was heated to 60° C. for 20 hours and concentrated. The concentrate was purified by flash column chromatography with 96:4 hexane/ethyl acetate to provide 2.63 g of the desired product. MS (ESI(+)) m/z 239 (M+H)⁺;

¹HNMR (CDCl₃) δ 0.59–0.64 (m, 2H), 0.85–0.91 (m, 2H), 2.46–2.54 (m, 1H), 5.16–5.22 (br s, 1H), 7.03 (d, J=8.6 Hz, 1H), 7.47 (dd, J=1.9, 8.6 Hz, 1H), 7.66 (d, J=1.9 Hz, 1H).

EXAMPLE 79B 1-cyclopropyl-5-cyanoindole

A solution of 40% by weight ethyl ethynyl ether (5.00 g, 28.5 mmol) in hexanes at 0° C. was treated dropwise with 1M catecholborane in THF (27.4 mL, 27.4 mmol), warmed to room temperature for 2 hours, heated at 70° C. for 2 hours, treated sequentially with a solution of 79A (1.35 g, 5.70 mmol) in THF (25 mL), 1,1'-bis(diphenylphosphino) ferrocene palladium (II) chloride (0.233 g, 0.285 mmol), and CsF (3.04 g, 20.0 mmol), stirred for 22 hours, treated with double the amount of catalyst and base, stirred for 20 hours, cooled to room temperature, treated with diethyl ether to double the reaction volume, filtered through silica gel, and concentrated. The concentrate was dissolved in THF (10 mL), treated with 2M HCl (10 mL), stirred for 2 days, transferred to 10% NaHCO₃ (100 mL), and extracted with ethyl acetate (100 mL then 3×30 mL). The combined extracts were washed with brine (50 mL), dried (MgSO₄), filtered through silica gel with ethyl acetate rinses, and concentrated. The concentrate was purified by radial chromatography with 9:1 hexane/ethyl acetate to provide 291 mg of the desired product.

MS (ESI(+)) m/z 183 (M+H)+;

¹H NMR (CDCl₃) δ 0.98–1.06 (m, 2H), 1.09–1.17 (m, 2H), 3.34–3.42 (m, 1H), 6.50 (d, J=3.3 Hz, 1H), 7.24 (d, J=3.3 Hz, 1H), 7.44 (dd, J=0.9, 8.1 Hz, 1H), 7.61 (dd, J=0.9, 8.1 Hz, 1H), 7.94 (app t, J=0.9 Hz, 1H).

EXAMPLE 79C 2-(1-cyclopropyl-5-indolyl)-5-(3,4,5-trimethoxyphenyl)-Δ2,3-oxazoline Example 79B (291 mg, 1.60 mmol) was processed as described in Example 23F to provide 23 mg of the desired product.

¹H NMR (CDCl₃) δ 1.00–1.06 (m, 2H), 1.07–1.14 (m, 2H), 3.34–3.41 (m, 1H), 3.84 (s, 6H), 3.85 (s, 3H), 4.00 (dd, J=7.6, 14.6 Hz, 1H), 4.48 (dd, J=10.2, 14.6 Hz, 1H), 5.59 (dd, J=7.6, 10.2 Hz, 1H), 6.49 (dd, J=0.7, 3.4 Hz, 1H), 6.59 (s, 2H), 7.17 (d, J=3.4 Hz, 1H), 7.59 (d, J=8.8 Hz, 1H), 7.93 (dd, J=1.4, 8.8 Hz, 1H), 8.29 (d, J=1.4 Hz, 1H);

HRMS (FAB) Calc. (M+H) for $C_{23}H_{25}N_2O_4$: 393.1814. Found: 393.1820.

Anal. calcd for $C_{23}H_{24}N_2O_4 \cdot 0.30H_2O$: C, 65.04; H, 5.87; N, 7.22. Found: C, 65.06; H, 5.88; N, 7.20.

What is claimed is:

1. A compound having Formula I

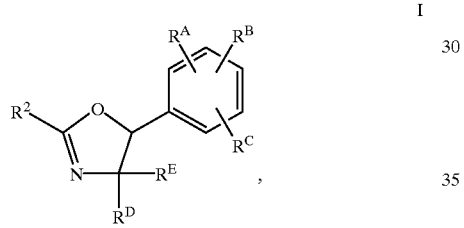

or a pharmaceutically acceptable salt or prodrug thereof, wherein $R^A$, $R^B$, and $R^C$ are independently selected from the group consisting of
 (1) alkyl,
 (2) alkoxy, and
 (3) thioalkoxy;

$R^D$ and $R^E$ are independently selected from the group consisting of
 (1) hydrogen and
 (2) alkyl;

$R^2$ is selected from the group consisting of
 (1) aryl and
 (2) heterocycle, wherein the heterocycle is selected from the group consisting of oxazole, isoxazole, thiazole, isothiazole, pyridine, pyridizine, pyrimidine, pyrazine, indole, isoindole, indolizine, indoline, benzo(b)thiene, 2,3-dihydrobenzothiene, benzo(b)furan, 2,3-dihydrobenzofuran, quinoline, isoquinoline, tetrahydroquinoline, 4H-quinolizine, and imidazo(1,5-a)pyridine, wherein (1) and (2) can be optionally substituted with one, two, three, four, or five substituents independently selected from $-L^1R^6$ wherein $L^1$ is selected from the group consisting of (a) a covalent bond,
(b) —C(X)—, wherein X is O or S,
(c) —S(O)$_t$—, wherein t is 0, 1, or 2,
(d) —NR3—, wherein $R^3$ is selected from the group consisting of
 (i) hydrogen,
 (ii) carboxaldehyde,
 (iii) alkanoyl,
 (iv) —C(O)OR¹¹, wherein $R^{11}$ is alkyl which can be optionally substituted with one or two aryl substituents,
 (v) cycloalkyl,
 (vi) alkyl, wherein the alkyl can be optionally substituted with one substituent selected from the group consisting of
  (1') alkoxy,
  (2') cycloalkyl, and
  (3') aryl,
 and
 (vii) —C(O)R¹³, wherein $R^{13}$ is perfluoroalkyl,
(e) —O—,
(f) —X'C(X)—, wherein X is defined previously and X' is O or S,
(g) —C(X)X—,
(h) —N(R³')C(O)N(R⁴')— wherein $R^{3'}$ and $R^{4'}$ are independently selected from the group consisting of
 (i) hydrogen and
 (ii) alkyl,
(i) —N(R )C(X)—, wherein $R^{3'}$ is defined above,
(j) —C(X)N(R³')—, wherein $R^{3'}$ is defined above,
(k) —NR³'S(O)$_t$—, wherein $R^{3'}$ is defined above, and
(l) —S(O)$_t$NR³'— wherein t and $R^{3'}$ are defined above, wherein (f)–(g) and (i)–(l) are drawn with their left ends attached to —R²— and their right ends attached to $R^6$, and $R^6$ is selected from the group consisting of (a) cyano,
(b) nitro,
(c) —XH,
(d) halo,
(e) —S(O)$_t$NR³R⁴, wherein $R^3$ is defined above, t' is one or two, and $R^4$ is selected from the group consisting of
 (i) hydrogen,
 (ii) cycloalkyl, and
 (iii) alkyl, wherein the alkyl can be optionally substituted with one substituent selected from the group consisting of
  (1') cycloalkyl and
  (2) aryl,
(f) —NR³R⁴, wherein $R^3$ and $R^4$ are hydrogen,
with the proviso that when $R^6$ is (a)–(f), —L¹— is a covalent bond,
(g) perfluoroalkyl,
with the proviso that when $R^6$ is perfluoroalkyl, —L¹— is a covalent bond or —C(X)—, wherein X is O,
(h) alkenyl,
(i) alkynyl,
(j) alkyl, and
(k) cycloalkyl, wherein (h)–(k) can be optionally substituted with one, two, three, four, or five substituents independently selected from the group consisting of (i) hydroxyl,
(ii) halo,
(iii) —OR$^{10}$, wherein R$^{10}$ is defined above,
(iv) —SR$^{10}$, wherein R$^{10}$ is defined above,
(v) —CO$_2$R$^5$, wherein R$^5$ is defined above,
(vi) —CHO,
(vii) =X, wherein X is defined above,
(viii) —N$_3$,
(ix) =C(H)NR$^3$R$^4$, wherein R$^3$ and R$^4$ are defined above,
(x) cyano,
(xi) —NOR$^3$, wherein R$^3$ is defined above,
(xii) —NR$^3$R$^4$, wherein R$^3$ and R$^4$ are defined above,
(xiii) —S(O)$_r$NR$^3$R$^4$, wherein R$^3$ and R$^4$ are defined above,
and
(xiv) nitro,
with the proviso that when R$^A$, R$^B$, and R$^C$ are alkoxy R$^2$ is not dialkoxyphenyl or trialkoxyphenyl.

2. A compound according to claim 1 wherein R is aryl and the aryl is optionally substituted.

3. A compound according to claim 2 selected from the group consisting of 2-(4-dimethylaminophenyl)-5-(3,4,5-trimethoxyphenyl)-Δ2,3-oxazoline,
2-(3-hydroxy-4-methoxyphenyl)-5-(3,4,5-trimethoxyphenyl)-Δ2,3-oxazoline,
2-(4-methoxyphenyl)-5-(3,4,5-trimethoxyphenyl)-Δ2,3-oxazoline,
2-(3,5-dimethoxyphenyl)-5-(3,4,5-trimethoxyphenyl)-Δ2,3-oxazoline,
2-(4-amino-3-methoxyphenyl)-5-(3,4,5-trimethoxyphenyl)-Δ2,3-oxazoline,
2-(4-amino-3-methylphenyl)-5-(3,4,5-trimethoxyphenyl)-Δ2,3-oxazoline,
2-(3-hydroxy-4-methoxyphenyl)-4-dimethyl-5-(3,4,5-trimethoxyphenyl)-Δ2,3-oxazoline,
2-(4-ethoxyphenyl)-5-(3,4,5-trimethoxyphenyl)-Δ2,3-oxazoline,
2-(4-benzyloxy-3-methoxyphenyl)-5-(3,4,5-t ethoxyphenyl)-Δ2,3-oxazoline,
2-(3-acetoxy-4-methoxyphenyl)-5-(3,4,5-trimethoxyphenyl)-Δ2,3-oxazoline,
2-(3-amino-4-methoxyphenyl)-5-(3,4,5-trimethoxyphenyl)-Δ2,3-oxazoline,
2-(3-amino-4-methyphenyl)-5-(3,4,5-trimethoxyphenyl)-Δ2,3-oxazoline,
2-(3-(Ala-Ala-amino-4-methoxyphenyl)-5-(3,4,5-trimethoxyphenyl)-Δ2,3-oxazoline,
2-(3-(Ala-amino-4-methoxyphenyl)-5-(3,4,5-trimethoxyphenyl)-Δ2,3-oxazoline,
2-(3-((3-aminopropionoyl)amino-4-methoxyphenyl)-5-(3,4,5-trimethoxyphenyl)-Δ2,3-oxazoline,
2-(3-(Ser-amino-4-methoxyphenyl)-5-(3,4,5-trimethoxyphenyl)-Δ2,3-oxazoline,
2-(3-(Gly-amino-4-methoxyphenyl)-5-(3,4,5-trimethoxyphenyl)-Δ2,3-oxazoline,
2-(3-fluoro-4-methoxyphenyl)-5-(3,4,5-trimethoxyphenyl)-Δ2,3-oxazoline,
2-(2-chloro-4-nitrophenyl)-5-(3,4,5-trimethoxyphenyl)-Δ2,3-oxazoline, and
2-(2-fluoro-4-nitrophenyl)-5-(3,4,5-trimethoxyphenyl)-Δ2,3-oxazoline.

4. A compound according to claim 1 wherein R$^2$ is heterocycle and the heterocycle is optionally substituted.

5. A compound according to claim 4 selected from the group consisting of 2-(3-acetylindol-5-yl)-5-(3,4,5-trimethoxyphenyl)-Δ2,3-oxazoline,
2-(1-methylindol-5-yl)-5-(3,4,5-trimethoxyphenyl)-Δ2,3-oxazoline,
2-(indol-3-yl)-5-(3,4,5-trimethoxyphenyl)-Δ2,3-oxazoline,
2-(indol-2-yl)-5-(3,4,5-trimethoxyphenyl)-Δ2,3-oxazoline,
2-(1-methoxymethylindol-5-yl)-5-(3,4,5-trimethoxyphenyl)-Δ2,3-oxazoline,
2-(indol-5-yl)-5-(3,4,5-trimethoxyphenyl)-Δ2,3-oxazoline,
2-(N-methyl-tetrahydroquinol-6-yl)-5-(3,4,5-trimethoxyphenyl)-Δ2,3-oxazoline,
2-(2,3-dihydro-5-bromo-7-benzofuranyl)-5-(3,4,5-trimethoxyphenyl)-Δ2,3-oxazoline,
2-(1-methyl-2,3-dihydro-indol-5-yl)-5-(3,4,5-trimethoxyphenyl)Δ2,3-oxazoline,
2-(1-methylindol-5-yl)-5-(3,4,5-trimethoxyphenyl)-Δ2,3-oxazoline, hydrochloride,
(5S)-2-(1-methylindol-5-yl)-5-(3,4,5-trimethoxyphenyl)-Δ2,3-oxazoline,
(5R)-2-(1-methylindol-5-yl)-5-(3,4,5-trimethoxyphenyl)-Δ2,3-oxazoline,
2-(1-ethylindol-5-yl)-5-(3,4,5-trimethoxyphenyl)-Δ2,3-oxazoline,
2-(6-indolyl)-5-(3,4,5-trimethoxyphenyl)-Δ2,3-oxazoline,
2-(1-methylindol-6-yl)-5-(3,4,5-trimethoxyphenyl)-Δ2,3-oxazoline,
2-(4-indolyl)-5-(3,4,5-trimethoxyphenyl)-Δ2,3-oxazoline,
2-(1-methylindol -4-yl )-5-(3,4,5-trimethoxyphenyl)-Δ2,3-oxazoline,
2-(7-indolyl)-5-(3,4,5-trimethoxyphenyl)-Δ2,3-oxazoline,
2-(1-methylindol -7-yl )-5-(3,4,5-trimethoxyphenyl)-Δ2,3-oxazoline,
2-(1-methylindol-3-yl)-5-(3,4,5-trimethoxyphenyl)-Δ2,3-oxazoline,
2-(1-methyl-indol-2-yl)-5-(3,4,5-trimethoxyphenyl)-Δ2,3-oxazoline,
2-(6-quinolinyl)-5-(3,4,5-trimothoxyphenyl)-Δ2,3-oxazoline,
2-(3-quinolinyl)-5-(3,4,5-trimethoxyphenyl)-Δ2,3-oxazoline,
2-(4-quinolinyl)-5-(3,4,5-trimethoxyphenyl)-Δ2,3-oxazoline,
2-(1-isoquinolinyl)-5-(3,4,5-trimethoxyphenyl)-Δ2,3-oxazoline,
2-(1-methyl-1H-pyridin-2-on-4-yl)-5-(3,4,5-trimethoxyphenyl)-Δ2,3-oxazoline,
2-(2-(2-hydroxyethyloxy)-4-pyridinyl)-5-(3,4,5-trimethoxyphenyl)-Δ2,3-oxazoline,
2-(imidazo[1,2-α]pyridin-6-yl)-5-(3,4,5-trimethoxyphenyl)-Δ2,3-oxazoline, 2-(imidazo[1,5-α]pyridin-6-yl)-5-(3,4,5-trimethoxyphenyl)-Δ2,3-oxazoline,
2-(2-methyl-6-indolizinyl)-5-(3,4,5-trimethoxyphenyl)-Δ2,3-oxazoline,
2-((2S)-indolin-2-yl)-5-(3,4,5-trimethoxyphenyl)-Δ2,3-oxazoline,
2-(1,4-dimethylindol-5-yl)-5-(3,4,5-trimethoxyphenyl)-Δ2,3-oxazoline,
(2-(1-methylthiothiocarbonylindol-5-yl)-5-(3,4,5-trimethoxyphenyl)-Δ2,3-oxazoline,
2-(1,3-dimethylindol-5-yl)-5-(3,4,5-trimethoxyphenyl)-Δ2,3-oxazoline,
2-(6-chloroindol-5-yl)-5-(3,4,5-trimethoxyphenyl)-Δ2,3-oxazoline,
2-(1-methyloxindol-5-yl)-5-(3,4,5-trimethoxyphenyl)-Δ2,3-oxazoline,
2-(1-methyl-6-chloroindol-5-yl)-5-(3,4,5-trimethoxyphenyl)-Δ2,3-oxazoline,
2-(1-difluoromethylindol-5-yl)-5-(3,4,5-trimethoxyphenyl)-Δ2,3-oxazoline,
2-(3-chloro-1-methylindol-5-yl)-5-(3,4,5-trimethoxyphenyl)-Δ2,3-oxazoline,
2-(7-fluoro-5-indolyl)-5-(3,4,5-trimethoxyphenyl)-Δ2,3-oxazoline,
2-(1-methyl-7-fluoro-5-indolyl)-5-(3,4,5-trimethoxyphenyl)-Δ2,3-oxazoline,
2-(7-chloro-5-indolyl)-5-(3,4,5-trimethoxyphenyl)-Δ2,3-oxazoline,
2-(1-methyl-7-chloro-5-indolyl)-5-(3,4,5-trimethoxyphenyl)-Δ2,3-oxazoline,
2-(3-fluoro-5-indolyl)-5-(3,4,5-trimethoxyphenyl)-Δ2,3-oxazoline,
2-(1-methyl-3-fluoro-5-indolyl)-5-(3,4,5-trimethoxyphenyl)-Δ2,3-oxazoline,
2-(1-hydroxymethylindol-5-yl)-5-(3,4,5-trimethoxyphenyl)-Δ2,3-oxazoline,
2-(1-methoxymethyl-5-indolyl)-5-(3,4,5-trimethoxyphenyl)-Δ2,3-oxazoline,
2-(1,2-diethyl-5-indolyl)-4,5-trimethoxyphenyl)-Δ2,3-oxazoline,
2-(7-methyl-5-indolyl)-5-(3,4,5-trimethoxyphenyl)-Δ2,3-oxazoline,
2-(1,7-dimethyl-5-indolyl)-5-(3,4,5-trimethoxyphenyl)-Δ2,3-oxazoline,
2-(1,2,7-rimethylindol-5-yl)-5-(3,4,5-trimethoxyphenyl)-Δ2,3-oxazoline,
2-(1,2-dimethylbenzimidazol-5-yl)-5-(3,4,5-trimethoxyphenyl)-Δ2,3-oxazoline,
2-(3-trifluoroacetyl-5-indolyl)-5-(3,4,5-t ethoxyphenyl)-Δ2,3-oxazoline,
(2-(1-methyl-3-trifluoroacetylindol-5-yl)-5-(3,4,5-trimethoxyphenyl)-Δ2,3-oxazoline,
2-(1-(2,2,2-trifluoroethyl)indol-5-yl)-5-(3,4,5-trimethoxyphenyl)-Δ2,3-oxazoline, and
2-(1-cyclopropyl-5-indolyl)-5-(3,4,5-trimethoxyphenyl)-Δ2,3-oxazoline.

6. A method for treating colon adenocarcinoma or lung carcinoma inhibiting cell proliferation in a mammal comprising administering to the mammal in need thereof an effective amount of a compound of claim 1.

7. A compound selected from the group consisting of
2-(4-dimethylaminophenyl)-5-(3,4,5-trimethoxyphenyl)-Δ2,3-oxazoline,
2-(3-hydroxy-4-methoxyphenyl)-5-(3,4,5-tethoxyphenyl)-Δ2,3-oxazoline,
2-(4-methoxyphenyl)-5-(3,4,5-trimethoxyphenyl)-Δ2,3-oxazoline,
2-(3,5-dimethoxyphenyl)-5-(3,4,5-trimethoxyphenyl)-Δ2,3-oxazoline,
2-(3-acetylindol-5-yl)-5-(3,4,5-trimethoxyphenyl)-Δ2,3-oxazoline,
2-(1-methylindol-5-yl)-5-(3,4,5-trimethoxyphenyl)-Δ2,3-oxazoline,
2-(indol-3-yl)-5-(3,4,5-trimethoxyphenyl)-Δ2,3-oxazoline,
2-(indol-2-yl)-5-(3,4,5-trimethoxyphenyl)-Δ2,3-oxazoline,
2-(1-methoxymethylindol-5-yl)-5-(3,4,5-trimethoxyphenyl)-Δ2,3-oxazoline,
2-(4-amino-3-methoxyphenyl)-5-(3,4,5-trimethoxyphenyl)-Δ2,3-oxazoline,
2-(indol-5-yl)-5-(3,4,5-trimethoxyphenyl)-Δ2,3-oxazoline,
2-(4-amino-3-methylphenyl)-5-(3,4,5-trimethoxyphenyl)-Δ2,3-oxazoline,
2-(3-hydroxy-4-methoxyphenyl)-4-dimethyl-5-(3,4,5-trimethoxyphenyl)-Δ2,3-oxazoline,
2-(N-methyl-tetrahydroquinol-6-yl)-5-(3,4,5-trimethoxyphenyl)-Δ2,3-oxazoline,
2-(4-ethoxyphenyl)-5-(3,4,5-trimethoxyphenyl)-Δ2,3-oxazoline,
2-(4-benzyloxy-3-methoxyphenyl)-5-(3,4,5-trimethoxyphenyl)-Δ2,3-oxazoline,
2-(2,3-dihydro-5-bromo-7-benzofuranyl)-5-(3,4,5-trimethoxyphenyl)-Δ2,3-oxazoline,
2-(3-acetoxy-4-methoxyphenyl)-5-(3,4,5-trimethoxyphenyl)-Δ2,3-oxazoline,
2-(1-methyl-2,3-dihydro-indol-5-yl)-5-(3,4,5-trimethoxyphenyl)-Δ2,3-oxazoline,
2-(1-methylindol-5-yl)-5-(3,4,5-trimethoxyphenyl)-Δ2,3-oxazoline, hydrochloride,
(5S)-2-(1-methylindol-5-yl)-5-(3,4,5-trimethoxyphenyl)-Δ2,3-oxazoline,
(5R)-2-(1-methylindol-5-yl)-5-(3,4,5-trimethoxyphenyl)-Δ2,3-oxazoline,
2-(1-ethylindol-5-yl)-5-(3,4,5-trimethoxyphenyl)-Δ2,3-oxazoline,
2-(6-indolyl)-5-(3,4,5-trimethoxyphenyl)-Δ2,3-oxazoline,
2-(1-methylindol-6-yl)-5-(3,4,5-trimethoxyphenyl)-Δ2,3-oxazoline,
2-(4-indolyl)-5-(3,4,5-trimethoxyphenyl)-Δ2,3-oxazoline,
2-(1-methylindol-4-yl)-5-(3,4,5-trimethoxyphenyl)-Δ2,3-oxazoline,
2-(7-indolyl)-5-(3,4,5-trimethoxyphenyl)-Δ2,3-oxazoline,
2-(1-methylindol-7-yl)-5-(3,4,5-trimethoxyphenyl)-Δ2,3-oxazoline,
2-(1-methylindol-3-yl)-5-(3,4,5-trimethoxyphenyl)-Δ2,3-oxazoline,
2-(1-methyl-indol-2-yl)-5-(3,4,5-trimethoxyphenyl)-Δ2,3-oxazoline,
2-(6-quinolinyl)-5-(3,4,5-trimethoxyphenyl)-Δ2,3-oxazoline, 2-(3-quinolinyl)-5-(3,4,5-trimethoxyphenyl)-Δ2,3-oxazoline,
2-(4-quinolinyl)-5-(3,4,5-trimethoxyphenyl)-Δ2,3-oxazoline,
2-(1-isoquinolinyl)-5-(3,4,5-trimethoxyphenyl)-Δ2,3-oxazoline,
2-(3-amino-4-methoxyphenyl)-5-(3,4,5-trimethoxyphenyl)-Δ2,3-oxazoline,
2-(3-amino-4-methyphenyl)-5-(3,4,5-trimethoxyphenyl)-Δ2,3-oxazoline,
2-(3-(Ala-Ala-amino-4-methoxyphenyl)-5-(3,4,5-trimethoxyphenyl)-Δ2,3-oxazoline,
2-(3-(Ala-airino-4-methoxyphenyl)-5-(3,4,5-trimethoxyphenyl)-Δ2,3-oxazoline,
2-(3-((3-aminopropionoyl)amino-4-methoxyphenyl)-5-(3,4,5-trimethoxyphenyl)-Δ2,3-oxazoline,
2-(3-(Ser-amino-4-methoxyphenyl)-5-(3,4,5-trimethoxyphenyl)-Δ2,3-oxazoline,
2-(3-(Gly-amino-4-methoxyphenyl)-5-(3,4,5-triethoxyphenyl)-Δ2,3-oxazoline,
2-(1-methyl-1H-pyridin-2-on-4-yl)-5-(3,4,5-trimethoxyphenyl)-Δ2,3-oxazoline,
2-(2-(2-hydroxyethyloxy)-4-pyridinyl)-5-(3,4,5-trimethoxyphenyl)-Δ2,3-oxazoline,
2-(imidazo[1,2-α]pyridin-6-yl)-5-(3,4,5-trimethoxyphenyl)-Δ2,3-oxazoline,
2-(imidazo[1,5-α]pyridin-6-yl)-5-(3,4,5-trimethoxyphenyl)-Δ2,3-oxazoline,
2-(2-methyl-6-indolizinyl)-5-(3,4,5-trimethoxyphenyl)-Δ2,3-oxazoline,
2-(3-fluoro-4-methoxyphenyl)-5-(3,4,5-trimethoxyphenyl)-Δ2,3-oxazoline,
2-((2S)-indolin-2-yl)-5-(3,4,5-trimethoxyphenyl)-Δ2,3-oxazoline,
2-(2-chloro-4-nitrophenyl)-5-(3,4,5-trimethoxyphenyl)-Δ2,3-oxazoline,
2-(2-fluoro-4-nitrophenyl)-5-(3,4,5-trimethoxyphenyl)-Δ2,3-oxazoline.
2-(1,4-dimethylindol-5-yl)-5-(3,4,5-trimethoxyphenyl)-Δ2,3-oxazoline,
(2-(1-methylthiothiocarbonylindol-5-yl)-5-(3,4,5-trimethoxyphenyl)-Δ2,3-oxazoline,
2-(1,3-dimethylindol-5-yl)-5-(3,4,5-trimethoxyphenyl)-Δ2,3-oxazoline,
2-(6-chloroindol-5-yl)-5-(3,4,5-trimethoxyphenyl)-Δ2,3-oxazoline,
2-(1-methyloxindol-5-yl)-5-(3,4,5-trimethoxyphenyl)-Δ2,3-oxazoline,
2-(1-methyl-6-chloroindol-5-yl)-5-(3,4,5-trimethoxyphenyl)-Δ2,3-oxazoline,
2-(1-difluoromethylindol-5-yl)-5-(3,4,5-trimethoxyphenyl)-Δ2,3-oxazoline,
2-(3-chloro-1-methylindol-5-yl)-5-(3,4,5-trimethoxyphenyl)-Δ2,3-oxazoline,
2-(7-fluoro-5-indolyl)-5-(3,4,5-trimethoxyphenyl)-Δ2,3-oxazoline,
2-(1-methyl-7-fluoro-5-indolyl)-5-(3,4,5-trimethoxyphenyl)-Δ2,3-oxazoline,
2-(7-chloro-5-indolyl)-5-(3,4,5-trimethoxyphenyl)-Δ2,3-oxazoline,
2-(1-methyl-7-chloro-5-indolyl)-5-(3,4,5-trimethoxyphenyl)-Δ2,3-oxazoline,
2-(3-fluoro-5-indolyl)-5-(3,4,5-trimethoxyphenyl)-Δ2,3-oxazoline,
(2-(1-methyl-3-fluoro-5-indolyl)-5-(3,4,5-trimethoxyphenyl)-Δ2,3-oxazoline,
2-(1-hydroxymethylindol-5-yl)-5-(3,4,5-trimethoxyphenyl)-Δ2,3-oxazoline,
2-(1-methoxymethyl-5-indolyl)-5-(3,4,5-trimethoxyphenyl)-Δ2,3-oxazoline,
2-(1,2-dimethyl-5-indolyl)-4,5-trimethoxyphenyl)-Δ2,3-oxazoline,
2-(7-methyl-5-indolyl)-5-(3,4,5-trimethoxyphenyl)-Δ2,3-oxazoline,
2-(1,7-dimethyl-5-indolyl)-5-(3,4,5-trimethoxyphenyl)-Δ2,3-oxazoline,
2-(1,2,7-trimethylindol-5-yl)-5-(3,4,5-trimethoxyphenyl)-Δ2,3-oxazoline,
2-(1,2-dimethylbenzimidazol-5-yl)-5-(3,4,5-trimethoxyphenyl)-Δ2,3-oxazoline,
2-(3-trifluoroacetyl-5-indolyl)-5-(3,4,5-trimethoxyphenyl)-Δ2,3-oxazoline,
(2-(1-methyl-3-trifluoroacetylindol-5-yl)-5-(3,4,5-trimethoxyphenyl)-Δ2,3-oxazoline,
2-(1-(2,2,2-trifluoroethyl)indol-5-yl)-5-(3,4,5-trimethoxyphenyl)-Δ2,3-oxazoline, and
2-(1-cyclopropyl-5-indolyl)-5-(3,4,5-trimethoxyphenyl)-Δ2,3-oxazoline.

\* \* \* \* \*

UNITED STATES PATENT AND TRADEMARK OFFICE
CERTIFICATE OF CORRECTION

PATENT NO. : 6,228,868 B1
DATED : May 8, 2001
INVENTOR(S) : Stephen L Gwaltney, II et al.

It is certified that error appears in the above-identified patent and that said Letters Patent is hereby corrected as shown below:

Column 55,
Line 61, replace "quinoline, isoguinoline," with -- quinoline, isoquinoline, --.
Line 62, replace "tetrahydrocuinoline, 4H-quinolizine, and" with -- tetrahydroquinoline, 4H-quinolizine, and --.

Column 56,
Line 30, replace "-N(R)C(X)-, where $R^{3'}$ is" with -- N($R^{3'}$)C(X)-, wherein $R^{3'}$ is --.

Column 57,
Line 44, replace "-methoxypheny D-5-(3,4,5-t ethoxyphenyl)-Δ2,3-oxazoline" with -- methoxyphenyl)-5-(3,4,5-trimethoxy-phenyl)-Δ2,3-oxazoline --.

Column 59,
Line 44, replace "(7-methyl-5-indo lyl)-5-(3,4,5-" with -- (7-methyl-5-indolyl)-5(3,4,5- --.
Line 48, replace "(1,2,7-rimethylindol-5-yl)-5-" with -- (1,2,7-trimethylindol-5-yl)-5- --.
Line 52, replace "-5(3,4,5-t ethoxyphenyl)-" with -- -5-(3,4,5-trimethoxyphenyl)- --.
Line 62, replace "carcinoma inhibiting cell proliferation in a mammal" with -- carcinoma in a mammal --.

Column 60,
Line 2, replace "tethoxyphenyl)- Δ 2,3-oxazoline," with -- trimethoxyphenyl)- Δ 2,3-oxazoline, --.

Column 61,
Line 14, replace "2-(3-(Ala-airino-4methoxyphenyl)" with -- 2-(3-(Ala-amino-4methoxyphenyl) --.
Line 22, replace "triethoxyphenyl)- Δ 2,3-oxazoline," with -- trimethoxyphenyl)- Δ 2, 3-oxazoline, --.

Signed and Sealed this

Ninth Day of April, 2002

JAMES E. ROGAN
Director of the United States Patent and Trademark Office